(12) United States Patent
Lopez

(10) Patent No.: US 9,883,951 B2
(45) Date of Patent: Feb. 6, 2018

(54) ARTIFICIAL DISC

(71) Applicant: Interventional Spine, Inc., Irvine, CA (US)

(72) Inventor: Rudolf Morgenstern Lopez, Barcelona (ES)

(73) Assignee: Interventional Spine, Inc., Irvine, CA (US)

( * ) Notice: Subject to any disclaimer, the term of this patent is extended or adjusted under 35 U.S.C. 154(b) by 507 days.

(21) Appl. No.: 14/424,412

(22) PCT Filed: Aug. 28, 2013

(86) PCT No.: PCT/US2013/057144
§ 371 (c)(1),
(2) Date: Feb. 26, 2015

(87) PCT Pub. No.: WO2014/036178
PCT Pub. Date: Mar. 6, 2014

(65) Prior Publication Data
US 2015/0223948 A1 Aug. 13, 2015

Related U.S. Application Data

(63) Continuation-in-part of application No. 13/794,067, filed on Mar. 11, 2013, now abandoned.
(Continued)

(51) Int. Cl.
*A61F 2/44* (2006.01)
*A61F 2/46* (2006.01)
(Continued)

(52) U.S. Cl.
CPC ........ *A61F 2/4425* (2013.01); *A61B 17/3417* (2013.01); *A61F 2/447* (2013.01);
(Continued)

(58) Field of Classification Search
None
See application file for complete search history.

(56) References Cited

U.S. PATENT DOCUMENTS

| 1,802,560 A | 4/1923 | Kerwin |
| 2,077,804 A | 4/1937 | Morrison |

(Continued)

FOREIGN PATENT DOCUMENTS

| DE | 3 023 353 | 4/1981 |
| DE | 197 00 474 A1 | 7/1998 |

(Continued)

OTHER PUBLICATIONS

Mar. 17, 2016 European Extended Search Report for Application No. 13832602.0, the European counterpart of the present application.
(Continued)

*Primary Examiner* — Sameh Boles
(74) *Attorney, Agent, or Firm* — Baker & Hostetler LLP

(57) ABSTRACT

Intervertebral implants and methods of delivering the intervertebral implants include delivering an implant through the Kambin's triangle from a posterolateral approach. The intervertebral implants can include a first body portion having an open configuration and a closed configuration. The intervertebral implants can also include a second body portion having an open configuration and a closed configuration. The first body portion removably connects to the second body portion.

16 Claims, 54 Drawing Sheets

Related U.S. Application Data

(60) Provisional application No. 61/694,947, filed on Aug. 30, 2012.

(51) Int. Cl.
    *A61B 17/34*     (2006.01)
    *A61F 2/30*     (2006.01)
    *A61B 17/00*     (2006.01)
    *A61B 17/32*     (2006.01)
    *A61B 17/16*     (2006.01)

(52) U.S. Cl.
    CPC .......... *A61F 2/4455* (2013.01); *A61F 2/4611* (2013.01); *A61B 17/1659* (2013.01); *A61B 17/1671* (2013.01); *A61B 2017/00261* (2013.01); *A61B 2017/320004* (2013.01); *A61B 2017/320008* (2013.01); *A61B 2017/3443* (2013.01); *A61B 2017/3445* (2013.01); *A61F 2002/30179* (2013.01); *A61F 2002/30365* (2013.01); *A61F 2002/30565* (2013.01); *A61F 2002/30579* (2013.01); *A61F 2002/30617* (2013.01); *A61F 2002/30784* (2013.01); *A61F 2002/30827* (2013.01); *A61F 2002/30879* (2013.01); *A61F 2002/443* (2013.01); *A61F 2002/4627* (2013.01); *A61F 2220/0016* (2013.01); *A61F 2220/0033* (2013.01)

(56) References Cited

U.S. PATENT DOCUMENTS

| | | |
|---|---|---|
| 2,121,193 A | 6/1938 | Hanicke |
| 2,243,717 A | 5/1941 | Moreira |
| 2,388,056 A | 7/1943 | Hendricks |
| 2,381,050 A | 8/1945 | Hardinge |
| 2,485,531 A | 10/1949 | Dzus et al. |
| 2,489,870 A | 11/1949 | Dzus |
| 2,570,465 A | 10/1951 | Lundholm |
| 2,677,369 A | 5/1954 | Knowles |
| 3,115,804 A | 12/1963 | Johnson |
| 3,312,139 A | 4/1967 | Di Cristina |
| 3,486,505 A | 12/1969 | Morrison |
| 3,489,143 A | 1/1970 | Holloran |
| 3,698,391 A | 10/1972 | Mahony |
| 3,760,802 A | 9/1973 | Fischer et al. |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,175,555 A | 11/1979 | Herbert |
| 4,236,512 A | 12/1980 | Aginsky |
| 4,262,665 A | 4/1981 | Roalstad et al. |
| 4,275,717 A | 6/1981 | Bolesky |
| 4,312,353 A | 1/1982 | Shahbabian |
| 4,341,206 A | 7/1982 | Perrett et al. |
| 4,350,151 A | 9/1982 | Scott |
| 4,369,790 A | 1/1983 | McCarthy |
| 4,401,112 A | 8/1983 | Rezaian |
| 4,401,433 A | 8/1983 | Luther |
| 4,409,974 A | 10/1983 | Freedland |
| 4,449,532 A | 5/1984 | Storz |
| 4,451,256 A | 5/1984 | Weikl et al. |
| 4,456,005 A | 6/1984 | Lichty |
| 4,463,753 A | 8/1984 | Gustilo |
| 4,488,543 A | 12/1984 | Tornier |
| 4,494,535 A | 1/1985 | Haig |
| 4,532,660 A | 8/1985 | Field |
| 4,537,185 A | 8/1985 | Stednitz |
| 4,545,374 A | 10/1985 | Jacobson |
| 4,573,448 A | 3/1986 | Kambin |
| 4,601,710 A | 7/1986 | Moll |
| 2,173,655 A | 10/1986 | Himoud |
| 4,625,725 A | 12/1986 | Davison et al. |
| 4,629,450 A | 12/1986 | Suzuki et al. |
| 4,632,101 A | 12/1986 | Freedland |
| 4,641,640 A | 2/1987 | Griggs |
| 4,640,271 A | 3/1987 | Lower |
| 4,653,489 A | 3/1987 | Tronzo |
| 4,667,663 A | 5/1987 | Miyata |
| 4,686,984 A | 8/1987 | Bonnet |
| 4,688,561 A | 8/1987 | Reese |
| 4,721,103 A | 1/1988 | Freedland |
| 4,723,544 A | 2/1988 | Moore et al. |
| 4,743,257 A | 5/1988 | Tormala et al. |
| 4,760,843 A | 8/1988 | Fischer et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,858,601 A | 8/1989 | Glisson |
| 4,862,891 A | 9/1989 | Smith |
| 4,863,476 A | 9/1989 | Shepperd |
| 4,873,976 A | 10/1989 | Schreiber |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,959,064 A | 9/1990 | Engelhardt |
| 4,963,144 A | 10/1990 | Huene |
| 4,966,587 A | 10/1990 | Baumgart |
| 4,968,317 A | 11/1990 | Tormala et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrel |
| 5,002,557 A | 3/1991 | Hasson |
| 5,011,484 A | 4/1991 | Breard |
| 5,013,315 A | 5/1991 | Barrows |
| 5,013,316 A | 5/1991 | Goble et al. |
| 5,059,193 A | 10/1991 | Kuslich |
| 5,062,849 A | 11/1991 | Schelhas |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,114,407 A | 5/1992 | Burbank |
| 5,116,336 A | 5/1992 | Frigg |
| 5,120,171 A | 6/1992 | Lasner |
| 5,122,133 A | 6/1992 | Evans |
| 5,122,141 A | 6/1992 | Simpson et al. |
| 5,139,486 A | 8/1992 | Moss |
| 5,158,543 A | 10/1992 | Lazarus |
| 5,167,663 A | 12/1992 | Brumfield |
| 5,167,664 A | 12/1992 | Hodorek |
| 5,169,400 A | 12/1992 | Muhling et al. |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,697 A | 1/1993 | Hasson et al. |
| 5,178,501 A | 1/1993 | Carstairs |
| 5,183,464 A | 2/1993 | Dubrul et al. |
| 5,188,118 A | 2/1993 | Terwilliger |
| 5,195,506 A | 3/1993 | Hulfish |
| 5,201,742 A | 4/1993 | Hasson |
| 5,217,462 A | 6/1993 | Asnis et al. |
| 5,217,486 A | 6/1993 | Rice et al. |
| 5,224,952 A | 7/1993 | Deniega et al. |
| 5,234,431 A | 8/1993 | Keller |
| 5,241,972 A | 9/1993 | Bonati |
| 5,242,410 A | 9/1993 | Melker |
| 5,242,427 A | 9/1993 | Bilweis |
| 5,242,447 A | 9/1993 | Borzone |

(56) References Cited

U.S. PATENT DOCUMENTS

| | | |
|---|---|---|
| 5,246,441 A | 9/1993 | Ross et al. |
| 5,250,049 A | 10/1993 | Michael |
| 5,269,797 A | 12/1993 | Bonati et al. |
| 5,280,782 A | 1/1994 | Wilk |
| 5,286,001 A | 2/1994 | Rafeld |
| 5,290,243 A | 3/1994 | Chodorow et al. |
| 5,300,074 A | 4/1994 | Frigg |
| 5,304,142 A | 4/1994 | Liebl et al. |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,324,261 A | 6/1994 | Amundson et al. |
| 5,334,184 A | 8/1994 | Bimman |
| 5,334,204 A | 8/1994 | Clewett et al. |
| 5,342,382 A | 8/1994 | Brinkerhoff et al. |
| 5,342,365 A | 9/1994 | Waldman |
| 5,344,252 A | 9/1994 | Kakimoto |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,382,248 A | 1/1995 | Jacobson et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,407,430 A | 4/1995 | Peters |
| 5,415,661 A | 5/1995 | Holmes |
| 5,424,773 A | 6/1995 | Saito |
| 5,449,359 A | 9/1995 | Groiso |
| 5,449,361 A | 9/1995 | Preissman |
| 5,452,748 A | 9/1995 | Simmons et al. |
| 5,454,790 A | 10/1995 | Dubrul et al. |
| 5,464,427 A | 11/1995 | Curtis et al. |
| 5,470,333 A | 11/1995 | Ray |
| 5,472,426 A | 12/1995 | Bonati et al. |
| 5,474,539 A | 12/1995 | Costa et al. |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach, Jr. et al. |
| 5,505,710 A | 4/1996 | Dorsey, III |
| 5,512,037 A | 4/1996 | Russell et al. |
| 5,514,180 A | 5/1996 | Heggeness et al. |
| 5,520,690 A | 5/1996 | Errico et al. |
| 5,520,896 A | 5/1996 | De Graaf et al. |
| 5,527,312 A | 6/1996 | Ray |
| 5,536,127 A | 7/1996 | Pennig |
| 5,540,688 A | 7/1996 | Navas |
| 5,540,693 A | 7/1996 | Fisher |
| 5,545,164 A | 8/1996 | Howland |
| 5,549,610 A | 8/1996 | Russell et al. |
| 5,554,191 A | 9/1996 | Lahille et al. |
| 5,558,674 A | 9/1996 | Heggeness et al. |
| D374,287 S | 10/1996 | Goble et al. |
| 5,564,926 A | 10/1996 | Branemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,591,168 A | 1/1997 | Judet et al. |
| 5,609,634 A | 3/1997 | Voydeville |
| 5,613,950 A | 3/1997 | Yoon |
| 5,618,142 A | 4/1997 | Sonden et al. |
| 5,618,314 A | 4/1997 | Harwin et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,639,276 A | 6/1997 | Weinstock et al. |
| 5,643,320 A | 7/1997 | Lower et al. |
| 5,645,589 A | 7/1997 | Li |
| 5,645,599 A | 7/1997 | Samani |
| 5,647,857 A | 7/1997 | Anderson et al. |
| 5,649,931 A | 7/1997 | Bryant et al. |
| 5,653,763 A | 8/1997 | Errico et al. |
| 5,658,335 A | 8/1997 | Allen |
| 5,662,683 A | 9/1997 | Kay |
| 5,665,095 A | 9/1997 | Jacobson |
| 5,665,122 A | 9/1997 | Kambin |
| 5,667,508 A | 9/1997 | Errico et al. |
| 5,669,915 A | 9/1997 | Caspar et al. |
| 5,693,100 A | 12/1997 | Pisharodi |
| 5,702,391 A | 12/1997 | Lin |
| 5,707,359 A | 1/1998 | Bufalinia |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,541 A | 3/1998 | Anspach, III et al. |
| 5,725,588 A | 3/1998 | Errico et al. |
| 5,728,097 A | 3/1998 | Mathews |
| 5,728,116 A | 3/1998 | Rosenman |
| 5,730,754 A | 3/1998 | Obenchain |
| 5,735,853 A | 4/1998 | Olerud |
| 5,741,282 A | 4/1998 | Anspach, III et al. |
| 5,743,881 A | 4/1998 | Demco |
| 5,743,912 A | 4/1998 | Lahille et al. |
| 5,743,914 A | 4/1998 | Skiba |
| 5,749,889 A | 5/1998 | Bacich et al. |
| 5,752,969 A | 5/1998 | Cunci et al. |
| 5,762,500 A | 6/1998 | Lazarof |
| 5,762,629 A | 6/1998 | Kambin |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,865 A | 7/1998 | Grptz |
| 5,792,044 A | 8/1998 | Foley et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,836,948 A | 11/1998 | Zucherman et al. |
| 5,846,259 A | 12/1998 | Berthiaume |
| 5,849,004 A | 12/1998 | Bramlet |
| 5,851,216 A | 12/1998 | Allen |
| 5,860,977 A | 1/1999 | Zucherman et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,228 A | 3/1999 | Knothe et al. |
| 5,893,850 A | 4/1999 | Cachia |
| 5,893,889 A | 4/1999 | Harrington |
| 5,895,428 A | 4/1999 | Berry |
| 5,902,231 A | 5/1999 | Foley et al. |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,671 A | 9/1999 | O'Neill |
| 5,954,722 A | 9/1999 | Bono |
| 5,954,747 A | 9/1999 | Clark |
| 5,957,902 A | 9/1999 | Teves |
| 5,957,924 A | 9/1999 | Tormala et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,976,139 A | 11/1999 | Bramlet |
| 5,976,146 A | 11/1999 | Ogawa et al. |
| 5,976,186 A | 11/1999 | Boa et al. |
| 5,980,522 A | 11/1999 | Koros et al. |
| 5,984,926 A | 11/1999 | Jones |

(56) References Cited

U.S. PATENT DOCUMENTS

| | | |
|---|---|---|
| 5,984,927 A | 11/1999 | Wenstrom, Jr. et al. |
| 5,984,966 A | 11/1999 | Kiena et al. |
| 5,989,255 A | 11/1999 | Pepper et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,519 A | 12/1999 | Rosselli |
| 6,007,566 A | 12/1999 | Wenstrom, Jr. |
| 6,007,580 A | 12/1999 | Lehto et al. |
| 6,010,513 A | 1/2000 | Tormala et al. |
| 6,015,410 A | 1/2000 | Tormala et al. |
| 6,019,762 A | 2/2000 | Cole |
| 6,022,352 A | 2/2000 | Vandewalle |
| 6,030,162 A | 2/2000 | Huebner |
| 6,030,364 A | 2/2000 | Durgin et al. |
| 6,033,406 A | 3/2000 | Mathews |
| 6,036,701 A | 3/2000 | Rosenman |
| 6,048,309 A | 4/2000 | Flom et al. |
| 6,048,342 A | 4/2000 | Zucherman et al. |
| 6,053,935 A | 4/2000 | Brenneman et al. |
| 6,066,142 A | 5/2000 | Serbousek et al. |
| 6,068,630 A | 5/2000 | Zucherman et al. |
| 6,068,648 A | 5/2000 | Cole et al. |
| 6,080,193 A | 6/2000 | Hochshuler et al. |
| 6,074,390 A | 7/2000 | Zucherman et al. |
| 6,083,244 A | 7/2000 | Lubbers et al. |
| 6,090,112 A | 7/2000 | Zucherman et al. |
| 6,102,914 A | 8/2000 | Bulstra et al. |
| 6,102,950 A | 8/2000 | Vaccaro |
| 6,117,174 A | 9/2000 | Nolan |
| 6,123,711 A | 9/2000 | Winters |
| 6,126,661 A | 10/2000 | Faccioli et al. |
| 6,126,663 A | 10/2000 | Hair |
| 6,129,762 A | 10/2000 | Li |
| 6,129,763 A | 10/2000 | Chauvin et al. |
| 6,146,384 A | 11/2000 | Lee et al. |
| 6,149,652 A | 11/2000 | Zucherman et al. |
| 6,149,669 A | 11/2000 | Li |
| 6,152,926 A | 11/2000 | Zucherman et al. |
| 6,156,038 A | 12/2000 | Zucherman et al. |
| 6,156,070 A | 12/2000 | Incavo et al. |
| 6,159,179 A | 12/2000 | Simonson |
| 6,161,350 A | 12/2000 | Espinosa |
| 6,162,234 A | 12/2000 | Freedland et al. |
| 6,162,236 A | 12/2000 | Osada |
| 6,168,595 B1 | 1/2001 | Durham et al. |
| 6,168,597 B1 | 1/2001 | Biedermann et al. |
| 6,175,758 B1 | 1/2001 | Kambin |
| 6,176,882 B1 | 1/2001 | Biedermann et al. |
| 6,183,471 B1 | 2/2001 | Zucherman et al. |
| 6,183,472 B1 | 2/2001 | Lutz |
| 6,183,474 B1 | 2/2001 | Bramlet et al. |
| 6,190,387 B1 | 2/2001 | Zucherman et al. |
| 6,197,041 B1 | 3/2001 | Shichman et al. |
| 6,200,322 B1 | 3/2001 | Branch et al. |
| 6,206,826 B1 | 3/2001 | Mathews et al. |
| 6,206,922 B1 | 3/2001 | Zdeblick et al. |
| 6,213,957 B1 | 4/2001 | Milliman et al. |
| 6,217,509 B1 | 4/2001 | Foley et al. |
| 6,221,082 B1 | 4/2001 | Marino et al. |
| 6,224,603 B1 | 5/2001 | Marino |
| 6,224,607 B1 | 5/2001 | Michaelson |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,238,397 B1 | 5/2001 | Zucherman et al. |
| 6,245,107 B1 | 6/2001 | Ferree |
| 6,248,108 B1 | 6/2001 | Tormala et al. |
| 6,251,111 B1 | 6/2001 | Barker et al. |
| 6,251,140 B1 | 6/2001 | Marino et al. |
| 6,264,676 B1 | 7/2001 | Gellman et al. |
| 6,267,765 B1 | 7/2001 | Taylor et al. |
| 6,267,767 B1 | 7/2001 | Strobel et al. |
| 6,280,444 B1 | 8/2001 | Zucherman et al. |
| 6,287,313 B1 | 9/2001 | Sasso |
| 6,290,701 B1 | 9/2001 | Enayate |
| 6,290,724 B1 | 9/2001 | Marino |
| 6,293,909 B1 | 9/2001 | Chu et al. |
| 6,293,952 B1 | 9/2001 | Brosens et al. |
| 6,306,136 B1 | 10/2001 | Baccelli |
| 6,319,254 B1 | 11/2001 | Giet et al. |
| 6,319,272 B1 | 11/2001 | Brenneman et al. |
| 6,332,882 B1 | 12/2001 | Zucherman et al. |
| 6,332,883 B1 | 12/2001 | Zucherman et al. |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Houser et al. |
| 6,364,897 B1 | 4/2002 | Bonutti |
| 6,368,325 B1 | 4/2002 | McKinley et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,682 B1 | 4/2002 | Fleishmann et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,395,007 B1 | 5/2002 | Bhatnagar et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,423,061 B1 | 7/2002 | Bryant |
| 6,423,067 B1 | 7/2002 | Eisermann |
| 6,425,919 B1 | 7/2002 | Lambrecht |
| 6,428,541 B1 | 8/2002 | Boyd et al. |
| 6,428,556 B1 | 8/2002 | Chin |
| 6,436,143 B1 | 8/2002 | Ross et al. |
| 6,440,154 B2 | 8/2002 | Gellman |
| 6,440,169 B1 | 8/2002 | Elberg et al. |
| 6,443,989 B1 | 9/2002 | Jackson |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,807 B1 | 9/2002 | Jackson |
| 6,458,134 B1 | 10/2002 | Songer et al. |
| 6,468,277 B1 | 10/2002 | Justin et al. |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Boyd et al. |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,491,714 B1 | 12/2002 | Bennett |
| 6,494,860 B2 | 12/2002 | Rocamora et al. |
| 6,494,893 B2 | 12/2002 | Dubrul et al. |
| 6,500,178 B2 | 12/2002 | Zucherman et al. |
| 6,506,192 B1 | 1/2003 | Gertzman et al. |
| 6,511,481 B2 | 1/2003 | von Hoffmann et al. |
| 6,514,256 B2 | 2/2003 | Zucherman et al. |
| 6,517,543 B1 | 2/2003 | Berrevoets et al. |
| 6,520,907 B1 | 2/2003 | Foley et al. |
| 6,527,774 B2 | 3/2003 | Lieberman |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,554,831 B1 | 4/2003 | Rivard et al. |
| 6,554,852 B1 | 4/2003 | Oberlander |
| 6,558,389 B2 | 5/2003 | Clark et al. |
| 6,562,046 B2 | 5/2003 | Sasso |

(56) References Cited

U.S. PATENT DOCUMENTS

| | | |
|---|---|---|
| 6,562,049 B1 | 5/2003 | Norlander et al. |
| 6,562,074 B2 | 5/2003 | Gerbec et al. |
| 6,575,979 B1 | 6/2003 | Cragg |
| 6,576,016 B1 | 6/2003 | Hochshuler et al. |
| 6,579,293 B1 | 6/2003 | Chandran |
| 6,582,390 B1 | 6/2003 | Sanderson |
| 6,582,431 B1 | 6/2003 | Ray |
| 6,582,433 B2 | 6/2003 | Yun |
| 6,582,441 B1 | 6/2003 | He et al. |
| 6,582,453 B1 | 6/2003 | Tran et al. |
| 6,582,437 B2 | 7/2003 | Dorchak et al. |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,595,998 B2 | 7/2003 | Johnson et al. |
| 6,596,008 B1 | 7/2003 | Kambin |
| 6,599,297 B1 | 7/2003 | Carlsson et al. |
| 6,607,530 B1 | 8/2003 | Carl et al. |
| 6,610,091 B1 | 8/2003 | Reiley |
| 6,613,050 B1 | 9/2003 | Wagner et al. |
| 6,616,678 B2 | 9/2003 | Nishtala et al. |
| 6,620,196 B1 | 9/2003 | Trieu |
| 6,626,944 B1 | 9/2003 | Taylor |
| 6,632,224 B2 | 10/2003 | Cachia et al. |
| 6,635,059 B2 | 10/2003 | Randall et al. |
| 6,635,362 B2 | 10/2003 | Ray, III et al. |
| 6,648,890 B2 | 11/2003 | Culbert et al. |
| 6,648,893 B2 | 11/2003 | Dudasik |
| 6,652,527 B2 | 11/2003 | Zucherman et al. |
| 6,655,962 B1 | 12/2003 | Kennard |
| 6,666,891 B2 | 12/2003 | Boehm, Jr. et al. |
| 6,669,698 B1 | 12/2003 | Tromanhauser et al. |
| 6,669,729 B2 | 12/2003 | Chin |
| 6,673,074 B2 | 1/2004 | Shluzas |
| 6,676,664 B1 | 1/2004 | Al-Assir |
| 6,679,833 B2 | 1/2004 | Smith et al. |
| 6,682,535 B2 | 1/2004 | Hoogland |
| 6,685,706 B2 | 2/2004 | Padget et al. |
| 6,685,742 B1 | 2/2004 | Jackson |
| 6,689,152 B2 | 2/2004 | Balceta et al. |
| 6,692,499 B2 | 2/2004 | Tormalaet et al. |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,716,247 B2 | 4/2004 | Michelson |
| 6,719,760 B2 | 4/2004 | Dorchak et al. |
| 6,723,096 B1 | 4/2004 | Dorchak et al. |
| 6,723,126 B1 | 4/2004 | Berry |
| 6,730,126 B2 | 5/2004 | Boehm, Jr. et al. |
| 6,733,496 B2 | 5/2004 | Sharkey et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hoschchuler et al. |
| 6,743,166 B2 | 6/2004 | Berci et al. |
| 6,746,451 B2 | 6/2004 | Middleton et al. |
| 6,752,831 B2 | 6/2004 | Sybert et al. |
| 6,761,720 B1 | 7/2004 | Senegas |
| 6,764,491 B2 | 7/2004 | Frey et al. |
| 6,770,075 B2 | 8/2004 | Howland |
| 6,773,460 B2 | 8/2004 | Jackson |
| 6,790,210 B1 | 9/2004 | Cragg et al. |
| 6,793,656 B1 | 9/2004 | Mathews |
| 6,796,983 B1 | 9/2004 | Zucherman et al. |
| 6,805,695 B2 | 10/2004 | Keith |
| 6,808,526 B1 | 10/2004 | Magerl et al. |
| 6,808,537 B2 | 10/2004 | Michelson |
| 6,821,298 B1 | 11/2004 | Jackson |
| 6,830,570 B1 | 12/2004 | Frey et al. |
| 6,830,589 B2 | 12/2004 | Erikson |
| 6,835,205 B2 | 12/2004 | Atkinson et al. |
| 6,835,206 B2 | 12/2004 | Jackson |
| 6,843,804 B2 | 1/2005 | Bryan |
| 6,852,126 B2 | 2/2005 | Ahlgren |
| 6,875,215 B2 | 4/2005 | Taras et al. |
| 6,887,243 B2 | 5/2005 | Culbert et al. |
| 6,890,333 B2 | 5/2005 | von Hoffmann et al. |
| 6,893,466 B2 | 5/2005 | Trieu |
| 6,902,566 B2 | 6/2005 | Zucherman et al. |
| 6,908,465 B2 | 6/2005 | von Hoffmann et al. |
| 6,916,323 B2 | 6/2005 | Kitchens et al. |
| 6,921,403 B2 | 6/2005 | Cragg et al. |
| 6,923,811 B1 | 8/2005 | Carl et al. |
| 6,929,606 B2 | 8/2005 | Ritland |
| 6,932,820 B2 | 8/2005 | Osman |
| 6,936,072 B2 | 8/2005 | Lambrecht et al. |
| 6,942,668 B2 | 9/2005 | Padget et al. |
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,972,035 B2 | 12/2005 | Michelson |
| 6,974,478 B2 | 12/2005 | Reiley et al. |
| 6,997,929 B2 | 2/2006 | Manzi et al. |
| 7,004,945 B2 | 2/2006 | Boyd et al. |
| 7,018,415 B1 | 3/2006 | McKay |
| 7,025,746 B2 | 4/2006 | Tal |
| 7,029,473 B2 | 4/2006 | Zucherman et al. |
| 7,041,107 B2 | 5/2006 | Pohjonen et al. |
| 7,048,736 B2 | 5/2006 | Zucherman et al. |
| 7,109,977 B2 | 5/2006 | Pohjonen et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,066,960 B1 | 6/2006 | Zucherman et al. |
| 7,066,961 B2 | 6/2006 | Michelson |
| 7,070,601 B2 | 7/2006 | Culbert et al. |
| 7,074,203 B1 | 7/2006 | Johanson et al. |
| 7,087,083 B2 | 8/2006 | Zucherman et al. |
| 7,087,087 B2 | 8/2006 | Boyer, II et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,118,572 B2 | 10/2006 | Bramlet et al. |
| 7,118,579 B2 | 10/2006 | Michelson |
| 7,118,598 B2 | 10/2006 | Michelson |
| 7,128,760 B2 | 10/2006 | Michelson |
| 7,153,305 B2 | 12/2006 | Johnson et al. |
| D536,096 S | 1/2007 | Hoogland et al. |
| 7,163,558 B2 | 1/2007 | Senegas et al. |
| 7,172,612 B2 | 2/2007 | Ishikawa |
| 7,179,294 B2 | 2/2007 | Eisermann et al. |
| 7,201,751 B2 | 4/2007 | Zucherman et al. |
| 7,226,481 B2 | 6/2007 | Kuslich |
| 7,261,738 B2 | 6/2007 | Casey |
| 7,238,204 B2 | 7/2007 | Couedic et al. |
| 7,267,683 B2 | 9/2007 | Sharkey et al. |
| 7,282,061 B2 | 10/2007 | Sharkey et al. |
| 7,306,628 B2 | 12/2007 | Zucherman et al. |
| 7,309,336 B2 | 12/2007 | Ashley et al. |
| 7,309,357 B2 | 12/2007 | Kim |
| 7,318,839 B2 | 1/2008 | Malbert et al. |
| 7,320,688 B2 | 1/2008 | Foley et al. |
| 7,335,203 B2 | 2/2008 | Winslow et al. |
| 7,361,140 B2 | 4/2008 | Ries et al. |
| 7,361,193 B2 | 4/2008 | Frey et al. |
| 7,371,238 B2 | 5/2008 | Soboleski et al. |
| 7,377,942 B2 | 5/2008 | Berry |
| 7,400,930 B2 | 7/2008 | Sharkey et al. |
| 7,326,211 B2 | 8/2008 | Padget et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,445,636 B2 | 11/2008 | Michelson |
| 7,445,637 B2 | 11/2008 | Taylor |
| D584,812 S | 1/2009 | Ries |

(56) References Cited

U.S. PATENT DOCUMENTS

| | | |
|---|---|---|
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,481,812 B2 | 1/2009 | Frey et al. |
| 7,488,326 B2 | 2/2009 | Elliott |
| 7,520,888 B2 | 4/2009 | Trieu |
| 7,534,269 B2 | 5/2009 | Casey |
| 7,547,317 B2 | 6/2009 | Cragg |
| 7,556,629 B2 | 7/2009 | von Hoffmann et al. |
| 7,556,651 B2 | 7/2009 | Humphreys et al. |
| 7,588,574 B2 | 9/2009 | Assell et al. |
| 7,625,378 B2 | 12/2009 | Foley |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,655,012 B2 | 2/2010 | DiPoto et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,690,381 B2 | 4/2010 | Bartish, Jr. et al. |
| 7,691,120 B2 | 4/2010 | Shluzas et al. |
| 7,699,878 B2 | 4/2010 | Pavlov et al. |
| 7,715,284 B2 | 5/2010 | Culbert |
| 7,717,944 B2 | 5/2010 | Foley et al. |
| 7,722,530 B2 | 5/2010 | Davison |
| 7,727,263 B2 | 6/2010 | Cragg |
| 7,740,633 B2 | 6/2010 | Assell et al. |
| 7,744,599 B2 | 6/2010 | Cragg |
| 7,762,995 B2 | 7/2010 | Eversull et al. |
| 7,763,025 B2 | 7/2010 | Assell et al. |
| 7,763,055 B2 | 7/2010 | Foley |
| 7,766,930 B2 | 8/2010 | DiPoto et al. |
| 7,771,479 B2 | 8/2010 | Humphreys et al. |
| 7,776,094 B2 | 8/2010 | McKinley et al. |
| 7,794,463 B2 | 9/2010 | Cragg |
| 7,799,032 B2 | 9/2010 | Assell et al. |
| 7,799,033 B2 | 9/2010 | Assell et al. |
| 7,799,034 B2 | 9/2010 | Johnson et al. |
| 7,799,036 B2 | 9/2010 | Davison et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,837,734 B2 | 11/2010 | Zucheman et al. |
| 7,846,183 B2 | 12/2010 | Blain |
| 7,850,695 B2 | 12/2010 | Pagliuca et al. |
| 7,850,733 B2 | 12/2010 | Baynham |
| 7,857,832 B2 | 12/2010 | Culbert et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,875,077 B2 | 1/2011 | Humphreys et al. |
| 7,887,548 B2 | 2/2011 | Usher, Jr. et al. |
| 7,887,589 B2 * | 2/2011 | Glenn .................. A61F 2/4425 623/17.14 |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,848 B2 | 3/2011 | Patel et al. |
| 7,931,689 B2 | 4/2011 | Hochschuler et al. |
| 7,938,832 B2 | 5/2011 | Culbert et al. |
| 7,972,382 B2 | 7/2011 | Foley et al. |
| 7,993,377 B2 | 8/2011 | Culbert et al. |
| 7,998,176 B2 | 8/2011 | Culbert |
| 8,062,375 B2 | 11/2011 | Glerum |
| 8,105,382 B2 | 1/2012 | Olmos et al. |
| 8,109,977 B2 | 2/2012 | Culbert et al. |
| 8,133,232 B2 | 3/2012 | Levy |
| 8,137,404 B2 | 3/2012 | Lopez et al. |
| 8,147,549 B2 | 4/2012 | Metcalf, Jr. et al. |
| 8,157,845 B2 | 4/2012 | Wamick et al. |
| 8,216,316 B2 | 7/2012 | Kirschman |
| 8,252,060 B2 | 8/2012 | Hansell et al. |
| 8,262,736 B2 | 9/2012 | Michelson |
| 8,273,129 B2 | 9/2012 | Baynham |
| 8,317,866 B2 | 11/2012 | Palmatier |
| 8,343,189 B2 | 1/2013 | Assell et al. |
| 8,366,777 B2 | 2/2013 | Matthis |
| 8,394,107 B2 | 3/2013 | Fanger et al. |
| 8,394,129 B2 | 3/2013 | Lopez et al. |
| 8,398,713 B2 | 3/2013 | Weiman |
| 8,518,087 B2 | 8/2013 | Morgenstern et al. |
| 8,551,092 B2 | 10/2013 | Morgan et al. |
| 8,551,094 B2 | 10/2013 | Hoffmann et al. |
| 8,556,949 B2 | 10/2013 | Teisen et al. |
| 8,568,481 B2 | 10/2013 | Olmos et al. |
| 8,597,333 B2 | 12/2013 | Morgenstern et al. |
| 8,623,021 B2 | 1/2014 | Ries et al. |
| 8,652,183 B1 | 2/2014 | Truman |
| 8,696,716 B2 | 4/2014 | Kartalian et al. |
| 8,709,088 B2 | 4/2014 | Kleiner et al. |
| 8,715,014 B2 | 5/2014 | Culbert |
| 8,852,242 B2 | 10/2014 | Lopez et al. |
| 8,852,243 B2 | 10/2014 | Lopez et al. |
| 8,926,704 B2 | 1/2015 | Glerum et al. |
| 8,945,190 B2 | 2/2015 | Culbert et al. |
| 2001/0012950 A1 | 8/2001 | Nishtala et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0049529 A1 | 12/2001 | Cachia et al. |
| 2001/0049530 A1 | 12/2001 | Culbert et al. |
| 2002/0001476 A1 | 1/2002 | Nagamine et al. |
| 2002/0032462 A1 | 3/2002 | Houser et al. |
| 2002/0055740 A1 | 5/2002 | Lieberman |
| 2002/0087152 A1 | 7/2002 | Mikus et al. |
| 2002/0091387 A1 | 7/2002 | Hoogland |
| 2002/0120335 A1 | 8/2002 | Angelucci et al. |
| 2002/0143331 A1 | 10/2002 | Zucherman et al. |
| 2002/0161444 A1 | 10/2002 | Choi |
| 2002/0183848 A1 | 12/2002 | Ray et al. |
| 2003/0004528 A1 | 1/2003 | Ishikawa |
| 2003/0004575 A1 | 1/2003 | Erickson |
| 2003/0028250 A1 | 2/2003 | Reiley et al. |
| 2003/0028251 A1 | 2/2003 | Mathews |
| 2003/0063582 A1 | 4/2003 | Culbert |
| 2003/0065330 A1 | 4/2003 | Zucherman et al. |
| 2003/0065396 A1 | 4/2003 | Michelson |
| 2003/0083688 A1 | 5/2003 | Simonson |
| 2003/0139648 A1 | 7/2003 | Foley et al. |
| 2003/0139813 A1 | 7/2003 | Messerli et al. |
| 2003/0187431 A1 | 10/2003 | Simonson |
| 2003/0208122 A1 | 11/2003 | Melkent et al. |
| 2003/0208220 A1 | 11/2003 | Worley et al. |
| 2003/0220643 A1 | 11/2003 | Ferree |
| 2003/0229350 A1 | 12/2003 | Kay |
| 2003/0233102 A1 | 12/2003 | Nakamura et al. |
| 2004/0006391 A1 | 1/2004 | Reiley |
| 2004/0008949 A1 | 1/2004 | Culbert |
| 2004/0019359 A1 | 1/2004 | Worley et al. |
| 2004/0024463 A1 | 2/2004 | Thomas et al. |
| 2004/0039400 A1 | 2/2004 | Schmeiding et al. |
| 2004/0049190 A1 | 3/2004 | Biedermann et al. |
| 2004/0049223 A1 | 3/2004 | Nishtala et al. |
| 2004/0054412 A1 | 3/2004 | Gerbec et al. |
| 2004/0059339 A1 | 3/2004 | Roehm et al. |
| 2004/0059350 A1 | 3/2004 | Gordon et al. |
| 2004/0097924 A1 | 5/2004 | Lambrecht et al. |
| 2004/0097941 A1 | 5/2004 | Weiner et al. |
| 2004/0097973 A1 | 5/2004 | Loshakove et al. |
| 2004/0106925 A1 | 6/2004 | Culbert |
| 2004/0106999 A1 | 6/2004 | Mathews |
| 2004/0127906 A1 | 7/2004 | Culbert et al. |
| 2004/0133280 A1 | 7/2004 | Trieu |
| 2004/0143284 A1 | 7/2004 | Chin |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0153156 A1 | 8/2004 | Cohen |
| 2004/0158258 A1 | 8/2004 | Bonati et al. |
| 2004/0162617 A1 | 8/2004 | Zucherman et al. |

(56) References Cited

U.S. PATENT DOCUMENTS

| | | |
|---|---|---|
| 2004/0172134 A1 | 9/2004 | Berry |
| 2004/0181231 A1 | 9/2004 | Emstad et al. |
| 2004/0186471 A1 | 9/2004 | Trieu |
| 2004/0186482 A1 | 9/2004 | Kolb et al. |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0225292 A1 | 11/2004 | Sasso et al. |
| 2004/0225361 A1 | 11/2004 | Glenn et al. |
| 2004/0243239 A1 | 12/2004 | Taylor |
| 2004/0249466 A1 | 12/2004 | Liu et al. |
| 2004/0254575 A1 | 12/2004 | Obenchain et al. |
| 2004/0260297 A1 | 12/2004 | Padget et al. |
| 2004/0266257 A1 | 12/2004 | Ries et al. |
| 2005/0021031 A1 | 1/2005 | Foley et al. |
| 2005/0033434 A1 | 2/2005 | Berry |
| 2005/0043796 A1 | 2/2005 | Grant et al. |
| 2005/0065610 A1 | 3/2005 | Pisharodi |
| 2005/0080443 A1 | 4/2005 | Fallin et al. |
| 2005/0085917 A1 | 4/2005 | Marnay et al. |
| 2005/0090833 A1 | 4/2005 | Di Poto |
| 2005/0090899 A1 | 4/2005 | DiPoto |
| 2005/0102202 A1 | 5/2005 | Linden et al. |
| 2005/0113927 A1 | 5/2005 | Malek |
| 2005/0118550 A1 | 6/2005 | Turri |
| 2005/0119657 A1 | 6/2005 | Goldsmith |
| 2005/0130929 A1 | 6/2005 | Boyd |
| 2005/0131406 A1 | 6/2005 | Reiley et al. |
| 2005/0131409 A1 | 6/2005 | Chervitz et al. |
| 2005/0131538 A1 | 6/2005 | Chervitz et al. |
| 2005/0137595 A1 | 6/2005 | von Hoffmann et al. |
| 2005/0143734 A1 | 6/2005 | Cachia et al. |
| 2005/0149030 A1 | 7/2005 | Serhan |
| 2005/0154467 A1 | 7/2005 | Peterman et al. |
| 2005/0165398 A1 | 7/2005 | Reiley |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0182414 A1 | 8/2005 | Manzi et al. |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0203512 A1 | 9/2005 | Hawkins et al. |
| 2005/0216026 A1 | 9/2005 | Culbert |
| 2005/0222681 A1 | 10/2005 | Richley et al. |
| 2005/0251142 A1 | 11/2005 | von Hoffmann et al. |
| 2005/0256525 A1 | 11/2005 | Culbert et al. |
| 2005/0278026 A1 | 12/2005 | Gordon et al. |
| 2005/0283238 A1 | 12/2005 | Reiley |
| 2006/0004326 A1 | 1/2006 | Collins et al. |
| 2006/0004398 A1 | 1/2006 | Binder et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0030872 A1 | 2/2006 | Culbert et al. |
| 2006/0036241 A1 | 2/2006 | Siegal |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041314 A1 | 2/2006 | Millard |
| 2006/0047296 A1 | 3/2006 | Embry et al. |
| 2006/0058790 A1 | 3/2006 | Carl et al. |
| 2006/0058807 A1 | 3/2006 | Landry et al. |
| 2006/0058880 A1 | 3/2006 | Wysocki et al. |
| 2006/0079908 A1 | 4/2006 | Lieberman |
| 2006/0084977 A1 | 4/2006 | Lieberman |
| 2006/0084988 A1 | 4/2006 | Kim |
| 2006/0085010 A1 | 4/2006 | Lieberman |
| 2006/0089642 A1 | 4/2006 | Diaz |
| 2006/0100707 A1 | 5/2006 | Stinson et al. |
| 2006/0106381 A1 | 5/2006 | Ferree et al. |
| 2006/0111714 A1 | 5/2006 | Foley |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0129244 A1 | 6/2006 | Ensign |
| 2006/0142765 A9 | 6/2006 | Dixon et al. |
| 2006/0142776 A1 | 6/2006 | Iwanari |
| 2006/0161166 A1 | 7/2006 | Johnson et al. |
| 2006/0178743 A1 | 8/2006 | Carter |
| 2006/0178745 A1 | 8/2006 | Bartish et al. |
| 2006/0178746 A1 | 8/2006 | Bartish, Jr. et al. |
| 2006/0195103 A1 | 8/2006 | Padget et al. |
| 2006/0200186 A1 | 9/2006 | Schmieding et al. |
| 2006/0217711 A1 | 9/2006 | Stevens et al. |
| 2006/0229629 A1 | 10/2006 | Manzi et al. |
| 2006/0229725 A1 | 10/2006 | Lechmann et al. |
| 2006/0235403 A1 | 10/2006 | Blain |
| 2006/0235410 A1 | 10/2006 | Ralph |
| 2006/0235412 A1 | 10/2006 | Blain |
| 2006/0247634 A1 | 11/2006 | Warner et al. |
| 2006/0247778 A1 | 11/2006 | Ferree |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0293662 A1 | 12/2006 | Boyer, II et al. |
| 2006/0293663 A1 | 12/2006 | Walkenhorst et al. |
| 2007/0010826 A1 | 1/2007 | Rhoda |
| 2007/0016191 A1 | 1/2007 | Culbert et al. |
| 2007/0032790 A1 | 2/2007 | Aschmann et al. |
| 2007/0055236 A1 | 3/2007 | Hudgins et al. |
| 2007/0067035 A1 | 3/2007 | Falahee |
| 2007/0073399 A1 | 3/2007 | Zipnick et al. |
| 2007/0093841 A1 | 4/2007 | Hooglad |
| 2007/0118132 A1 | 5/2007 | Culbert et al. |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0162005 A1 | 7/2007 | Peterson et al. |
| 2007/0168036 A1 | 7/2007 | Ainsworth et al. |
| 2007/0185491 A1 | 8/2007 | Foley et al. |
| 2007/0203491 A1 | 8/2007 | Pasquet et al. |
| 2007/0233083 A1 | 10/2007 | Abdou |
| 2007/0233089 A1 | 10/2007 | DiPoto et al. |
| 2007/0233244 A1 | 10/2007 | Lopez et al. |
| 2007/0233253 A1 | 10/2007 | Bray et al. |
| 2007/0260248 A1 | 11/2007 | Tipirneni |
| 2007/0260314 A1 | 11/2007 | Biyani |
| 2007/0260318 A1 | 11/2007 | Lawson |
| 2007/0270954 A1 | 11/2007 | Wu |
| 2007/0270968 A1 | 11/2007 | Baynham et al. |
| 2007/0282449 A1 | 12/2007 | de Villiers |
| 2008/0015699 A1 | 1/2008 | Voydeville |
| 2008/0015703 A1 | 1/2008 | Casey |
| 2008/0039842 A1 | 2/2008 | Sweeney |
| 2008/0058598 A1 | 3/2008 | Ries et al. |
| 2008/0077148 A1 | 3/2008 | Ries et al. |
| 2008/0082172 A1 | 4/2008 | Jackson |
| 2008/0097436 A1 | 4/2008 | Culbert et al. |
| 2008/0108996 A1 | 5/2008 | Padget et al. |
| 2008/0125864 A1 | 5/2008 | deVilliers et al. |
| 2008/0140207 A1 | 6/2008 | Olmos et al. |
| 2008/0147193 A1 | 6/2008 | Matthis et al. |
| 2008/0177334 A1 | 7/2008 | Stinnette |
| 2008/0221623 A1 | 9/2008 | Gooch |
| 2008/0255618 A1 | 10/2008 | Fisher et al. |
| 2008/0262619 A1 | 10/2008 | Ray |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306481 A1 | 12/2008 | Farr et al. |
| 2008/0306537 A1 | 12/2008 | Culbert et al. |
| 2009/0005870 A1 | 1/2009 | Hawkins et al. |
| 2009/0036893 A1 | 2/2009 | Kartalian et al. |
| 2009/0062807 A1 | 3/2009 | Song |
| 2009/0069813 A1 | 3/2009 | von Hoffmann et al. |
| 2009/0131986 A1 | 3/2009 | Lee et al. |

(56) References Cited

U.S. PATENT DOCUMENTS

| | | |
|---|---|---|
| 2009/0093885 A1 | 4/2009 | Levieux et al. |
| 2009/0099610 A1 | 4/2009 | Johnson et al. |
| 2009/0105745 A1 | 4/2009 | Culbert et al. |
| 2009/0149857 A1 | 6/2009 | Culbert et al. |
| 2009/0182429 A1 | 7/2009 | Humphreys et al. |
| 2009/0187246 A1 | 7/2009 | Foley |
| 2009/0222100 A1 | 9/2009 | Cipoletti et al. |
| 2009/0240335 A1 | 9/2009 | Arcenio et al. |
| 2009/0275890 A1 | 11/2009 | Leibowitz et al. |
| 2009/0292361 A1 | 11/2009 | Lopez |
| 2010/0016973 A1 | 1/2010 | de Villiers et al. |
| 2010/0040332 A1 | 2/2010 | Culbert et al. |
| 2010/0076492 A1 | 3/2010 | Warner et al. |
| 2010/0082109 A1 | 4/2010 | Greenhalgh |
| 2010/0114147 A1 | 5/2010 | Biyani |
| 2010/0161062 A1 | 6/2010 | Foley et al. |
| 2010/0174314 A1 | 7/2010 | Mirkovic |
| 2010/0191336 A1 | 7/2010 | Greenhalgh |
| 2010/0211176 A1 | 8/2010 | Greenhalgh |
| 2010/0217330 A1 | 8/2010 | Phan et al. |
| 2010/0268228 A1 | 10/2010 | Petersen |
| 2010/0268231 A1 | 10/2010 | Kuslich |
| 2010/0268341 A1 | 10/2010 | Dvorak et al. |
| 2010/0286787 A1 | 11/2010 | Villiers et al. |
| 2010/0292700 A1 | 11/2010 | Ries |
| 2010/0292796 A1 | 11/2010 | Greenhalgh et al. |
| 2010/0298938 A1 | 11/2010 | Humphreys et al. |
| 2010/0318134 A1 | 12/2010 | Roche et al. |
| 2010/0331891 A1 | 12/2010 | Culbert et al. |
| 2011/0054538 A1 | 3/2011 | Zehavi et al. |
| 2011/0071527 A1 | 3/2011 | Nelson et al. |
| 2011/0087296 A1 | 4/2011 | Reiley et al. |
| 2011/0098531 A1 | 4/2011 | To |
| 2011/0098628 A1 | 4/2011 | Yeung et al. |
| 2011/0130838 A1 | 6/2011 | Lopez |
| 2011/0137421 A1 | 6/2011 | Hansell et al. |
| 2011/0144687 A1 | 6/2011 | Kleiner |
| 2011/0144766 A1 | 6/2011 | Kale et al. |
| 2011/0153020 A1 | 6/2011 | Abdelgany |
| 2011/0172774 A1 | 7/2011 | Varela |
| 2011/0208226 A1 | 8/2011 | Fatone et al. |
| 2011/0218575 A1 | 9/2011 | Culbert et al. |
| 2011/0230965 A1 | 9/2011 | Schell et al. |
| 2011/0238072 A1 | 9/2011 | Tyndall |
| 2011/0251690 A1 | 10/2011 | Berger et al. |
| 2011/0264147 A1 | 10/2011 | Culbert |
| 2011/0282453 A1 | 11/2011 | Greenhalgh |
| 2011/0307010 A1 | 12/2011 | Pradhan |
| 2011/0313465 A1 | 12/2011 | Warren et al. |
| 2011/0319997 A1 | 12/2011 | Glerum et al. |
| 2012/0004732 A1 | 1/2012 | Goel et al. |
| 2012/0006361 A1 | 1/2012 | Glerum |
| 2012/0059474 A1 | 3/2012 | Weiman |
| 2012/0059475 A1 | 3/2012 | Weiman |
| 2012/0059480 A1 | 3/2012 | Schell et al. |
| 2012/0065734 A1 | 3/2012 | Barrett et al. |
| 2012/0071978 A1 | 3/2012 | Suedkamp et al. |
| 2012/0089228 A1 | 4/2012 | Poulos |
| 2012/0150304 A1 | 6/2012 | Glerum |
| 2012/0150305 A1 | 6/2012 | Glerum |
| 2012/0158146 A1 | 6/2012 | Glerum |
| 2012/0158147 A1 | 6/2012 | Glerum |
| 2012/0158148 A1 | 6/2012 | Glerum |
| 2012/0185049 A1 | 7/2012 | Varela |
| 2012/0191194 A1 | 7/2012 | Olmos et al. |
| 2012/0197405 A1 | 8/2012 | Cuevas |
| 2012/0203290 A1 | 8/2012 | Warren et al. |
| 2012/0203347 A1 | 8/2012 | Glerum |
| 2012/0209386 A1 | 8/2012 | Triplett et al. |
| 2012/0215262 A1 | 8/2012 | Culbert et al. |
| 2012/0226357 A1 | 9/2012 | Varela |
| 2012/0232552 A1 | 9/2012 | Lopez et al. |
| 2012/0232658 A1 | 9/2012 | Lopez et al. |
| 2012/0265309 A1 | 10/2012 | Glerum |
| 2012/0277864 A1 | 11/2012 | Brodke et al. |
| 2012/0290090 A1 | 11/2012 | Glerum |
| 2012/0290091 A1 | 11/2012 | Kirschman |
| 2012/0290097 A1 | 11/2012 | Cipoletti |
| 2012/0303039 A1 | 11/2012 | Chin et al. |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0053894 A1 | 2/2013 | Gamache et al. |
| 2013/0096634 A1 | 4/2013 | Suh |
| 2013/0190769 A1 | 7/2013 | Lopez |
| 2013/0197642 A1 | 8/2013 | Ernst |
| 2013/0231747 A1 | 9/2013 | Olmos |
| 2013/0245703 A1 | 9/2013 | Warren |
| 2014/0067069 A1 | 3/2014 | Lopez |
| 2014/0142629 A1 | 5/2014 | Hoffmann |
| 2014/0236296 A1 | 8/2014 | Wagner et al. |
| 2014/0257296 A1 | 9/2014 | Lopez |
| 2014/0257484 A1 | 9/2014 | Flower |
| 2014/0257489 A1 | 9/2014 | Warren |
| 2014/0277204 A1 | 9/2014 | Sandhu |
| 2014/0277473 A1 | 9/2014 | Perrow |
| 2014/0371532 A1 | 12/2014 | Trovato |
| 2015/0018891 A1 | 1/2015 | Culbert |
| 2015/0094610 A1 | 4/2015 | Lopez |

FOREIGN PATENT DOCUMENTS

| | | |
|---|---|---|
| DE | 198 32 798 | 11/1999 |
| DE | 201 01 793 U1 | 5/2001 |
| EP | 0 077 159 | 4/1983 |
| EP | 0 260 044 | 3/1988 |
| EP | 0 525 352 A1 | 2/1993 |
| EP | 0 611 557 | 8/1994 |
| EP | 0 625 336 | 11/1994 |
| EP | 0 433 717 | 6/1997 |
| EP | 1 046 376 A1 | 4/2000 |
| EP | 0 853 929 B1 | 9/2002 |
| EP | 1 378 205 A1 | 7/2003 |
| EP | 1 374 784 A1 | 1/2004 |
| EP | 1 676 538 | 7/2006 |
| EP | 1 757 529 A1 | 2/2007 |
| EP | 1 864 616 | 12/2007 |
| EP | 1 379 186 | 5/2009 |
| EP | 2 100 565 | 9/2009 |
| EP | 1 523 278 | 11/2009 |
| EP | 2 331 023 | 6/2011 |
| EP | 1 845 874 | 10/2012 |
| EP | 2 683 310 | 1/2014 |
| EP | 2 688 498 | 1/2014 |
| EP | 2 890 332 | 7/2015 |
| ES | 200801551 | 5/2008 |
| FR | 2 699 065 | 12/1992 |
| FR | 2 728 778 | 12/1994 |
| FR | 2 745 709 | 3/1996 |
| FR | 2 800 601 | 11/1999 |
| FR | 2 801 189 | 11/1999 |
| FR | 2 808 182 | 4/2000 |
| GB | 2157788 A | 10/1985 |
| GB | 2173565 A | 10/1986 |
| JP | 64-52439 | 2/1989 |
| JP | 6-319742 A | 11/1994 |
| JP | 07-502419 | 3/1995 |
| JP | 07-184922 | 7/1995 |
| JP | 10-085232 A | 4/1998 |
| JP | 11-089854 A | 4/1999 |
| JP | 2004-194731 | 7/2004 |
| JP | 2005-533627 | 11/2005 |
| JP | 2011-511107 | 5/2009 |
| JP | 4988203 | 8/2012 |
| JP | 5164571 | 12/2012 |
| WO | WO 91/09572 | 12/1989 |
| WO | WO 93/04652 | 3/1993 |
| WO | WO 96/28100 | 9/1996 |
| WO | WO 99/52478 | 10/1999 |
| WO | WO 99/62417 | 12/1999 |
| WO | WO 00/67652 | 5/2000 |

(56) References Cited

FOREIGN PATENT DOCUMENTS

| WO | WO 2000/76409 | 12/2000 |
|---|---|---|
| WO | WO 2001/12054 | 2/2001 |
| WO | WO 2001/54598 | 8/2001 |
| WO | WO 2001/80751 | 11/2001 |
| WO | WO 2002/43601 | 6/2002 |
| WO | WO 2002/078555 | 10/2002 |
| WO | WO 2003/021308 | 3/2003 |
| WO | WO 2003/043488 | 5/2003 |
| WO | WO 2004/008949 | 1/2004 |
| WO | WO 2004/064603 | 8/2004 |
| WO | WO 2004/078220 | 9/2004 |
| WO | WO 2004/078221 | 9/2004 |
| WO | WO 2004/098453 | 11/2004 |
| WO | WO 2005/041818 | 5/2005 |
| WO | WO 2005/112835 | 12/2005 |
| WO | WO 2006/017507 | 2/2006 |
| WO | WO 2006/063083 | 6/2006 |
| WO | WO 2006/108067 | 10/2006 |
| WO | WO 2007/048038 | 4/2007 |
| WO | WO 2007/119212 | 10/2007 |
| WO | WO 2007/124130 | 4/2008 |
| WO | WO 2008/044057 | 4/2008 |
| WO | WO 2008/070863 | 6/2008 |
| WO | WO 2008/064842 | 11/2008 |
| WO | WO 2009/047630 | 4/2009 |
| WO | WO 2006/047363 | 5/2009 |
| WO | WO 2009/152919 | 12/2009 |
| WO | WO 2009/155577 | 12/2009 |
| WO | WO 2010/011941 | 1/2010 |
| WO | WO 2010/062971 | 6/2010 |
| WO | WO 2010/136170 | 12/2010 |
| WO | WO 2010/148112 | 12/2010 |
| WO | WO 2011/046460 | 4/2011 |
| WO | WO 2011/079910 | 7/2011 |
| WO | WO 2010/135156 | 11/2011 |
| WO | WO 2011/142761 | 11/2011 |
| WO | WO 2011/150350 | 12/2011 |
| WO | WO 2012/048008 | 4/2012 |
| WO | WO 2014/036178 | 3/2014 |

OTHER PUBLICATIONS

Gray's Anatomy, Crown Publishers, Inc., 1977, pp. 33-54.
U.S. Appl. No. 09/266,138, filed Mar. 10, 1999, Cachia.
U.S. Appl. No. 11/417,904, filed May 3, 2006, von Hoffman et al.
U.S. Appl. No. 11/417,904, filed May 3, 2006, Culbert.
U.S. Appl. No. 14/470,820, filed Aug. 27, 2014, Lopez et al.
U.S. Appl. No. 14/574,859, filed Dec. 18, 2014, Culbert et al.
Alfen, et al., "Developments in the Area of Edoscopic Spine Surgery". European Musculoskeletal Review 2006, pp. 23-24.
ThessysTM, Transforminal Endoscopic Spine System. Medical Solutions, ioimax®.
Brochure for PERPOS PLS System Surgical Technique by Interventional Spine.
Brooks, M.D., et al. Efficacy of Supplemental Posterior Transfacet Pedicle Device Fixation in the Setting of One- or Two-Level Anterior Lumbar Interbody Fusion.
Chin, Kingsley R., M.D. "Early Results of the Triage Medical Percutaneous Transfacet Pedicular BONE-LOK Compression Device for Lumbar Fusion".
Iprenburg, et al., "Transforaminal Endoscopic Surgery in Lumbar Disc Herniation in an Economic Crisis—The TESSYS Method". US Musculoskeletal, 2008 pp. 47-49.
James F. Zucherman, "A Multicenter, Prospective, Randomized Trial Evaluating the X STOP Interspinous Process Decompression System for the Treatment of Neurogenic Intermittent Claudication", SPINE vol. 30, No. 12, pp. 1351-1358.
Kambin, et al; Percutaneous Lateral Discectomy of the Lumbar Spine: A Preliminary Report; Clin. Orthop.; 1983; 174: 127-132.
Kambin, et al; Percutaneous Posterolateral Discectomy. Anatomy and Mechanism; Clin. Orthop. Relat. Res.; Oct. 1987; 223: 145-154.
King, M.D., Don, "Internal Fixation for Lumbosacral Fusion", The Journal of Bone and Joint Surgery. J Bone Joint Surg Am. 1948; 30:560-578.
Mahar, et al. Biomechanical Comparison of a Novel Percutaneous Transfacet Device and a Traditional Posterior System for Single Level Fusion. Journal of Spinal Disorders & Techniques, Dec. 2006, vol. 19 No. 8, pp. 591-594.
Manal Siddiqui, "The Positional Magnetic Resonance Imaging Changes in the Lumbar Spine Following Insertion of a Novel Interspinous Process Distraction Device", Spine vol. 30, No. 23, pp. 2677-2682.
Medco Forum, "Percutaneous Lumbar Fixation Via PERPOS PLS System Interventional Spine". Sep. 2008, vol. 15, No. 37.
Medco Forum, "Percutaneous Lumbar Fixation via PERPOS System From Interventional Spine". Oct. 2007, vol. 14, No. 49.
Morgenstern R; Transforaminal Endoscopic Stenosis Surgery—A Comparative Study of Laser and Reamed Foraminoplasty.In: European Musculoskeletal Review, Issue 1,2009.
Niosi, Christina A., "Biomechanical characterization of the three-dimentional kinematic behaviour of the Dynesys dynamic stabilization system: an in vitro study", EUR SPINE J (2006) 15: pp. 913-922.
Paul D. Fuchs, "The Use of an Interspinous Implant in Conjunction With a Graded Facetectomy Procedure", SPINE vol. 30, No. 11, pp. 1266-1272.
ProMapTM EMG Navigation Probe. Technical Brochure Spineology Inc., dated May 2009.
Vikram Talwar, "Insertion loads of the X STOP interspinous process distraction system designed to treat neurogenic intermittent claudication", EUR SPINE J (2006) 15: pp. 908-912.

\* cited by examiner

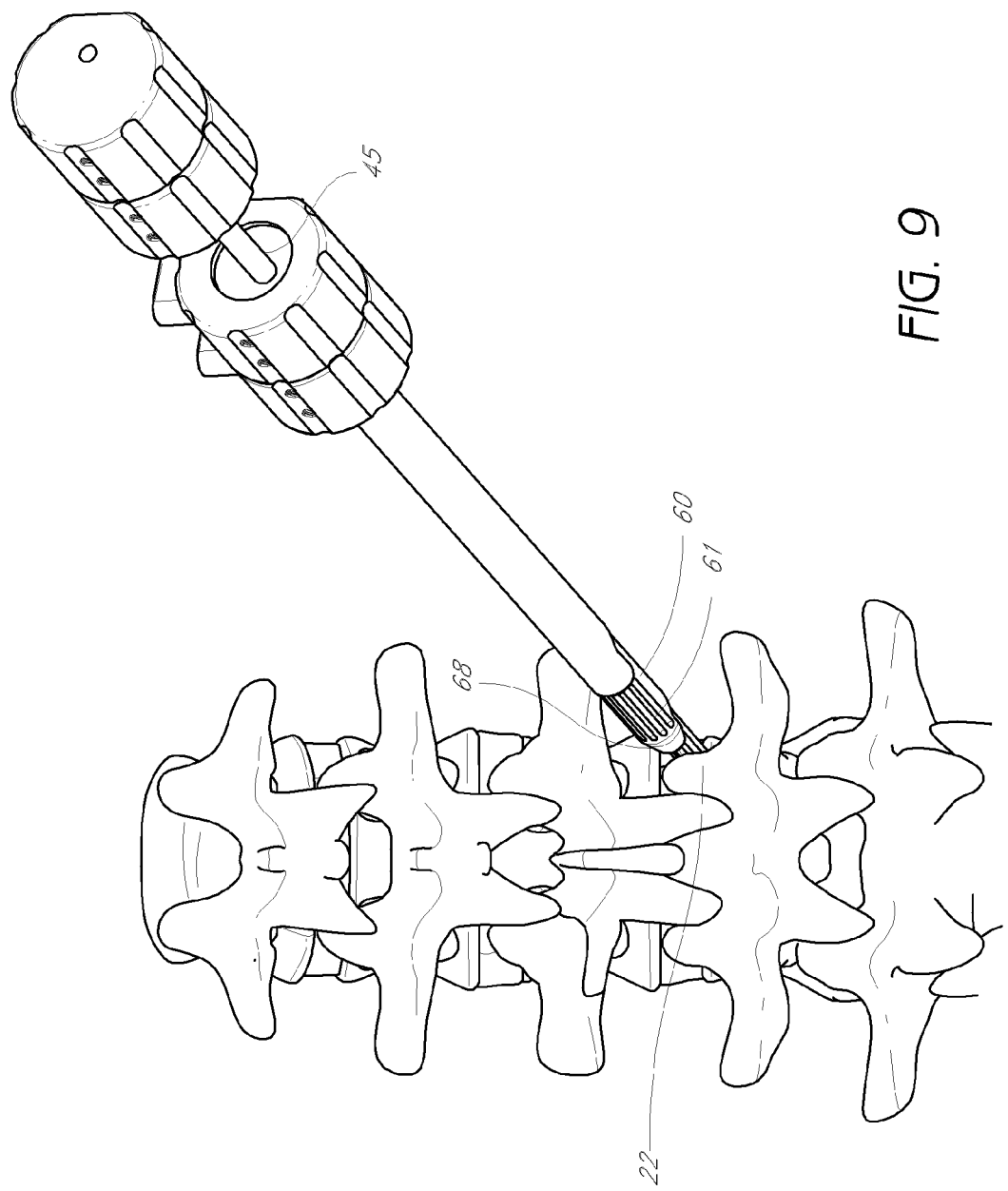

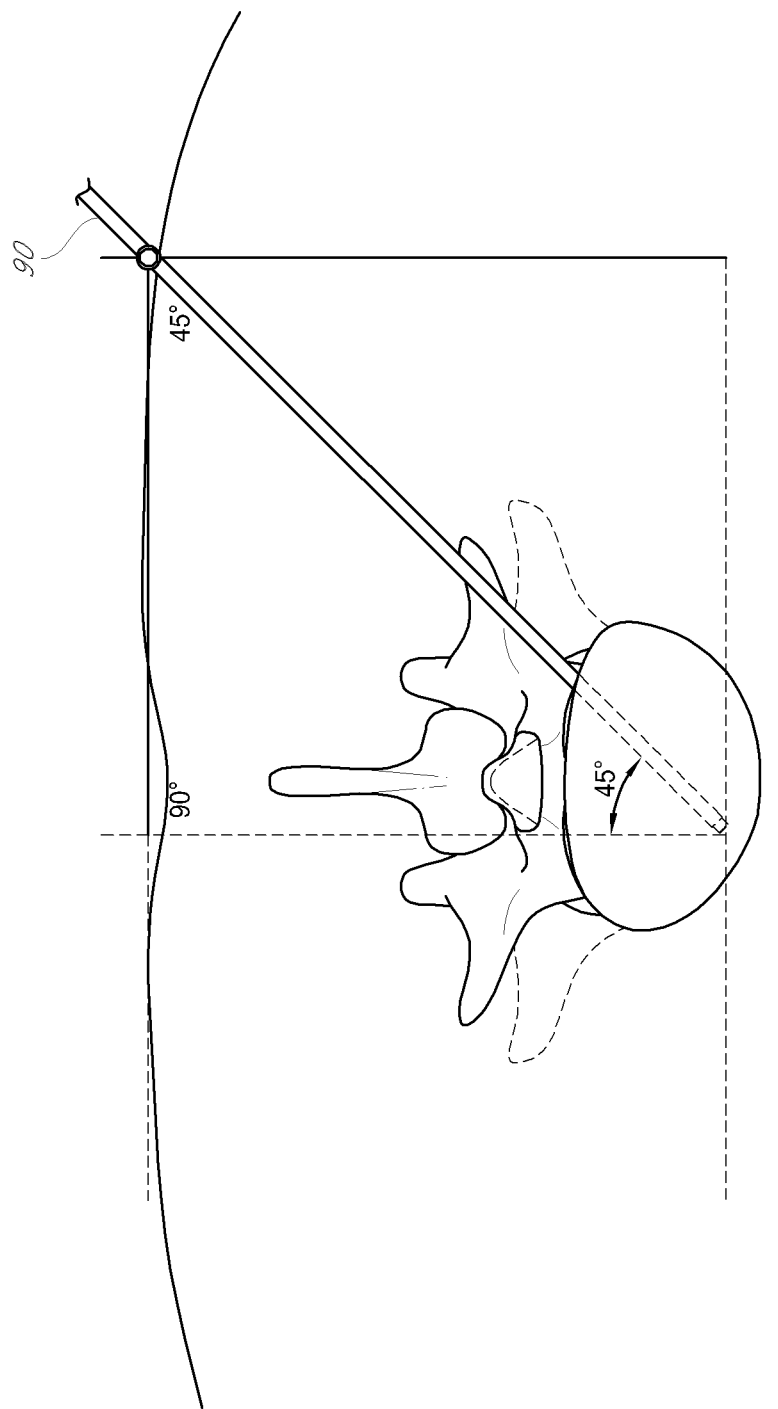

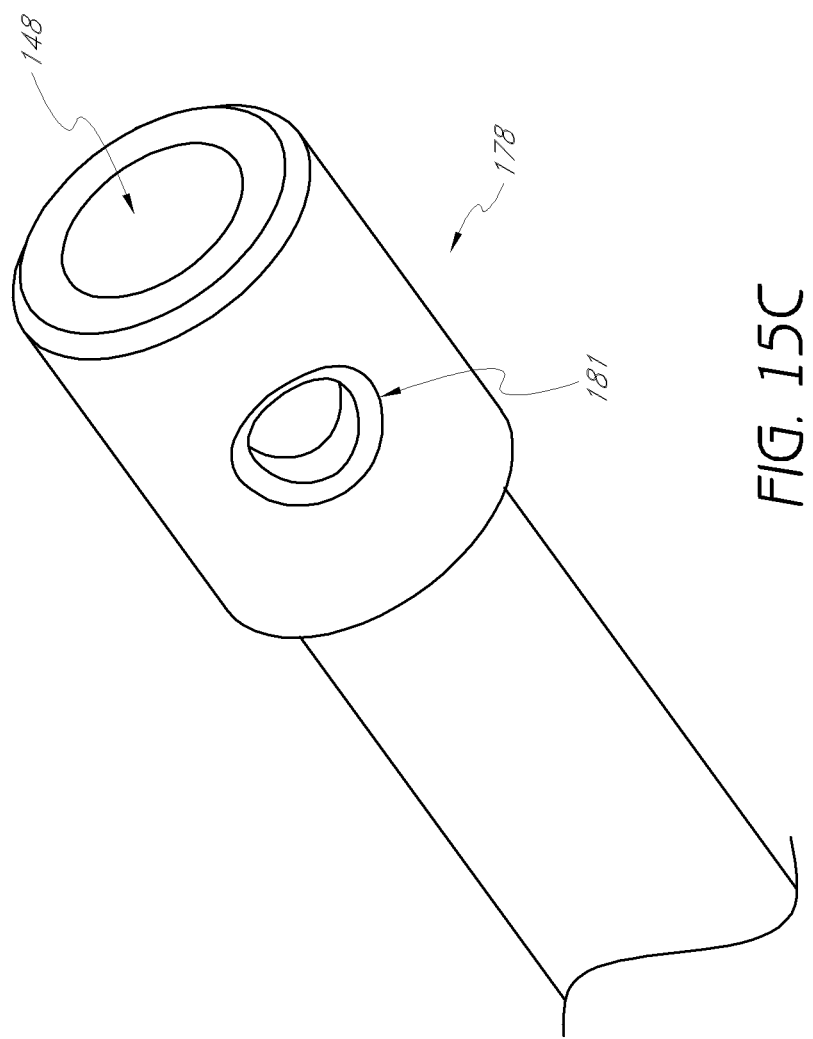

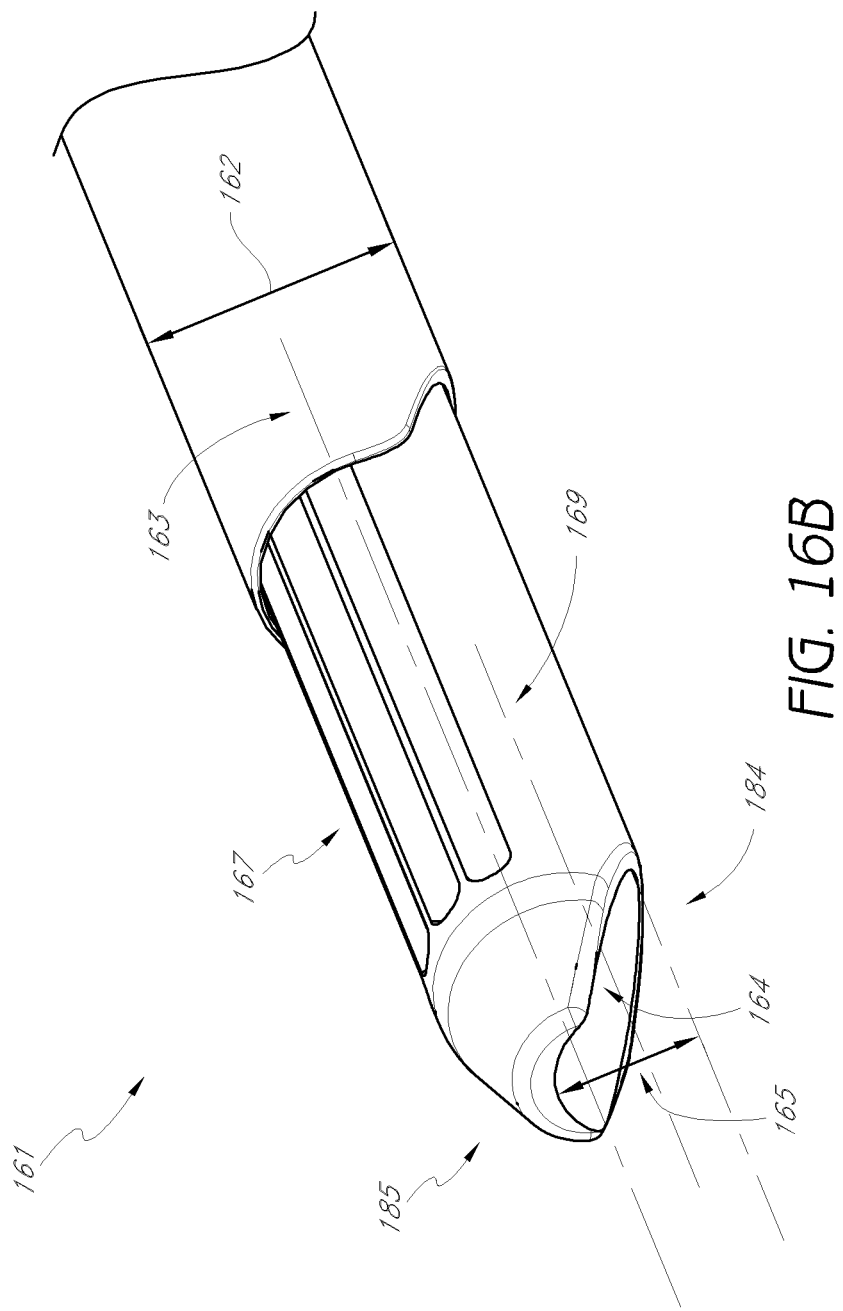

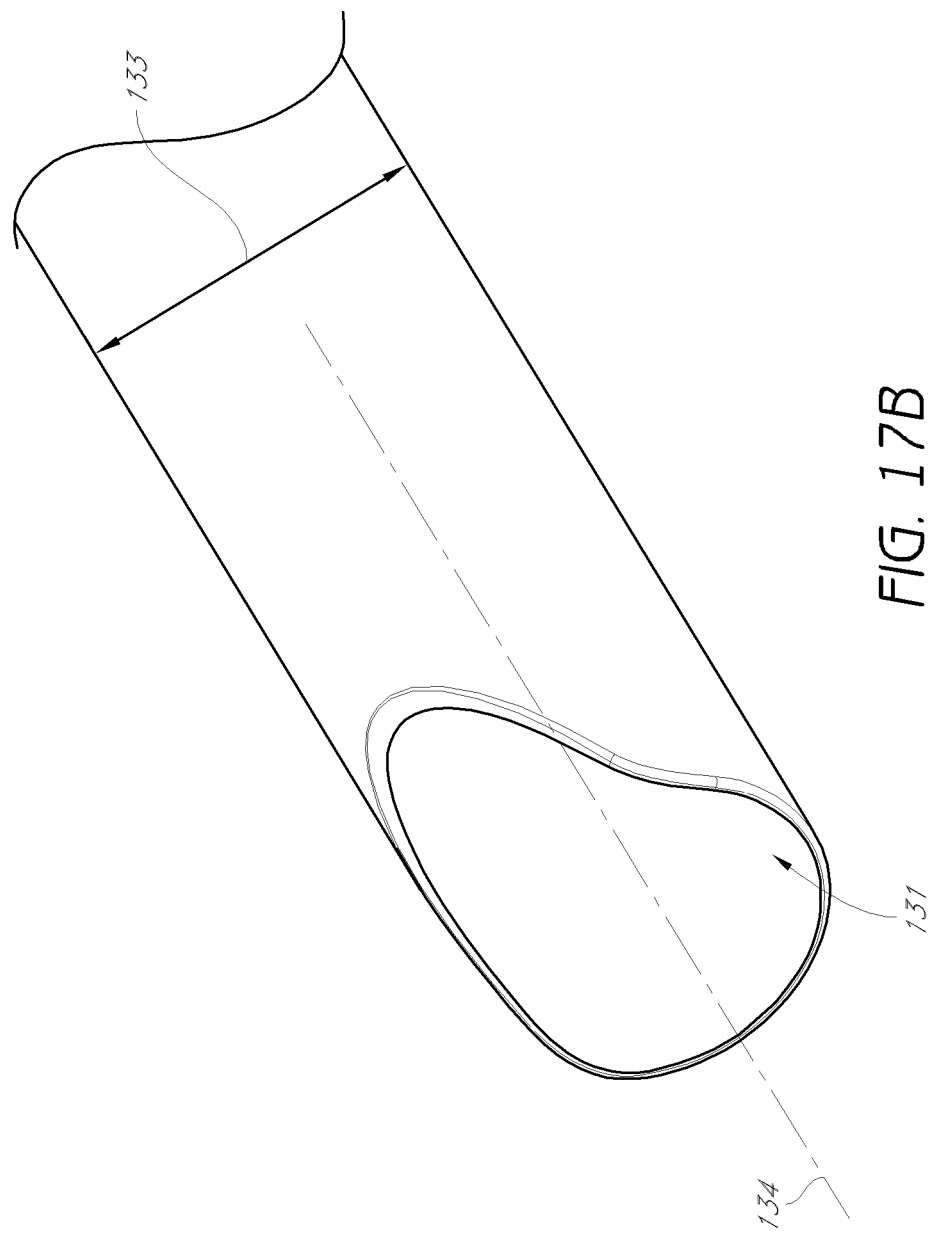

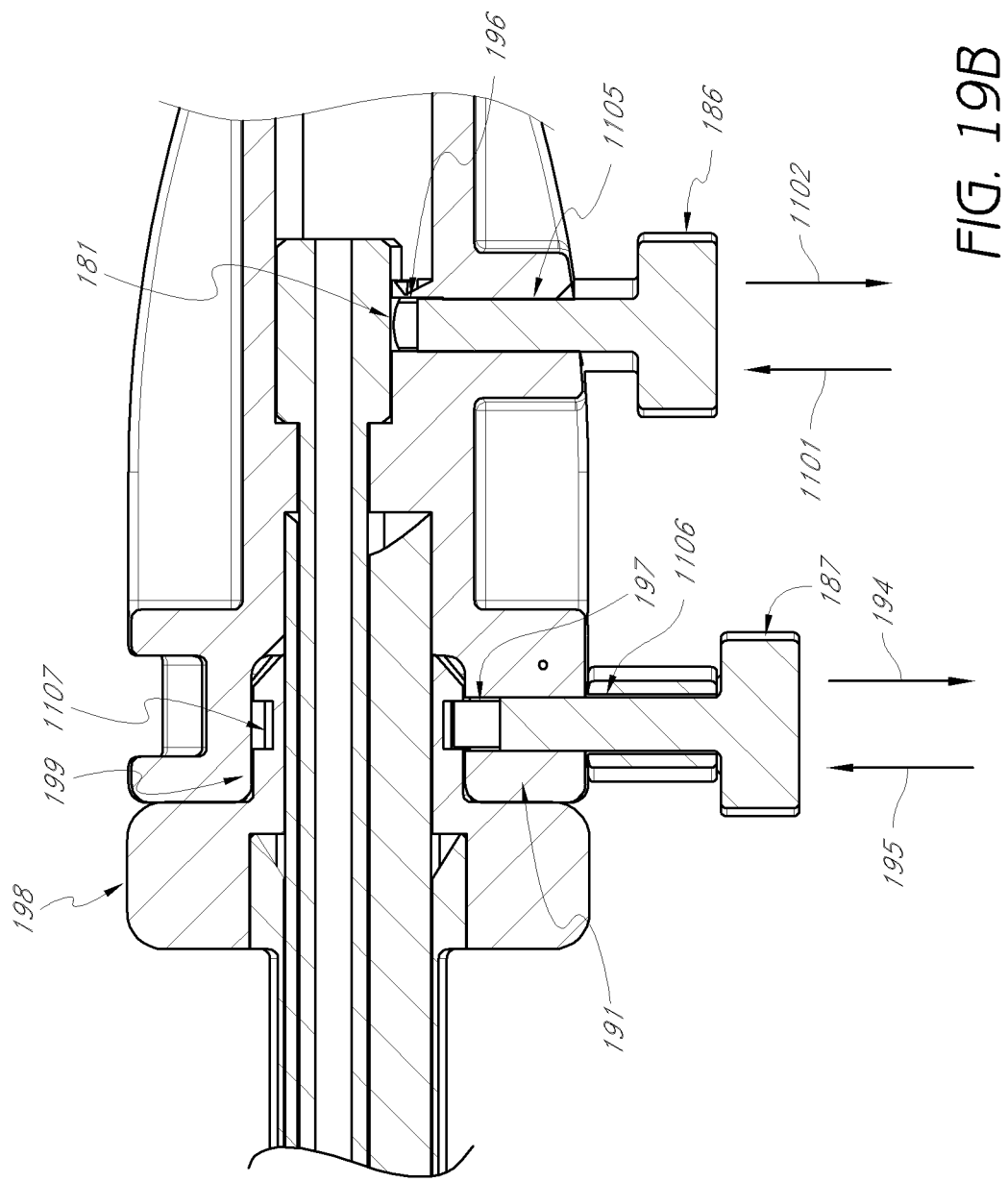

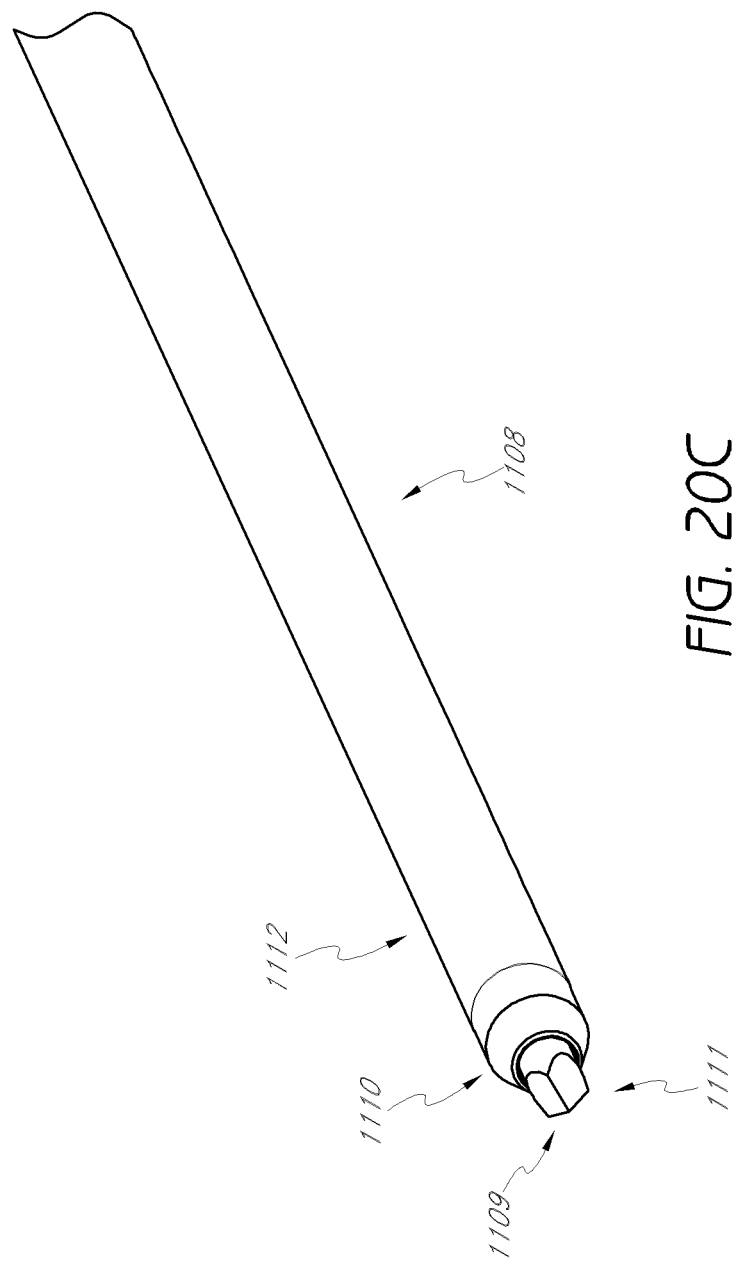

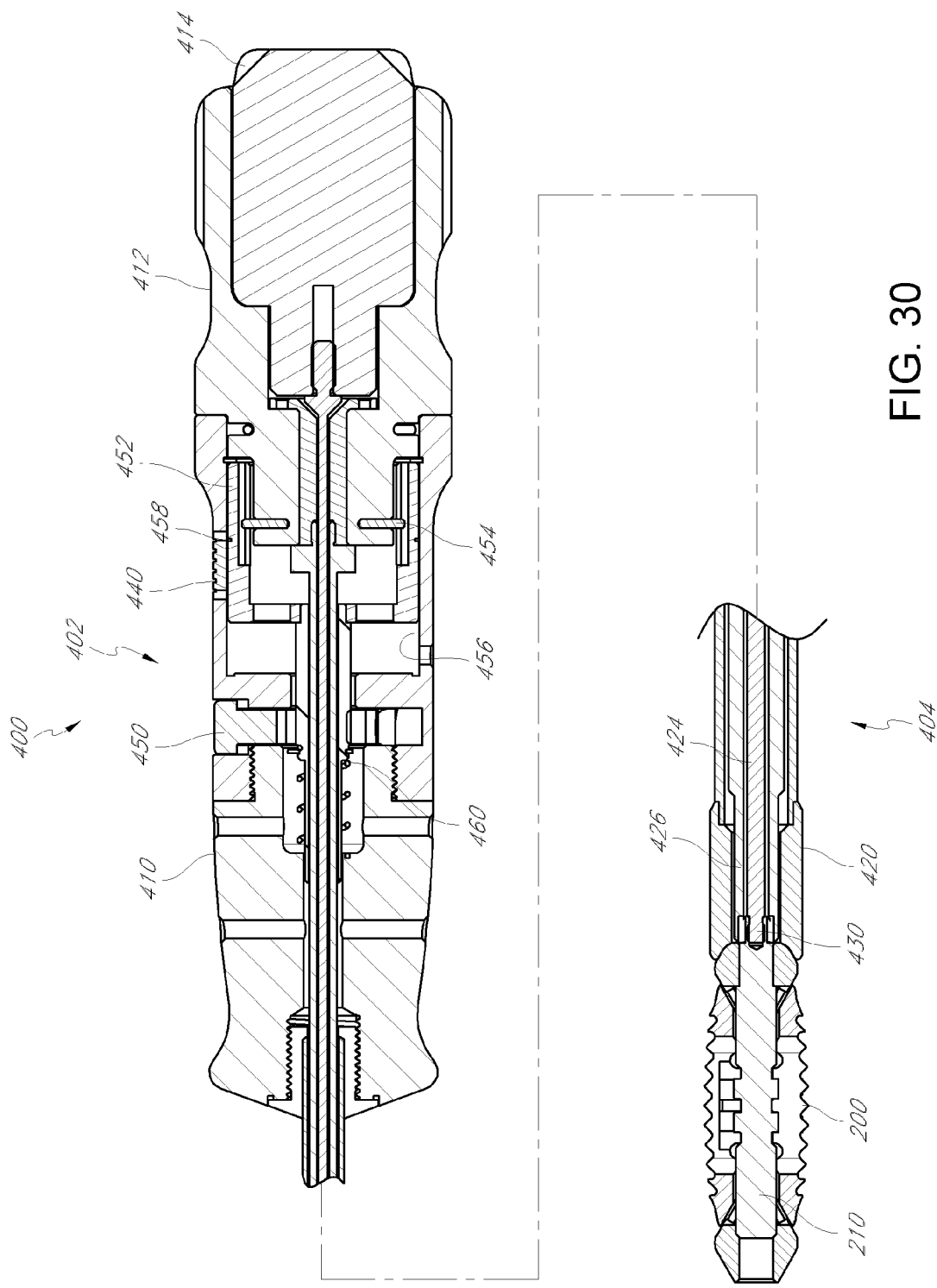

ARTIFICIAL DISC

BACKGROUND

Field

The present application relates to medical devices and, more particularly, to a medical device and method for treating the spine.

Description of the Related Art

The human spine is a flexible weight bearing column formed from a plurality of bones called vertebrae. There are thirty-three vertebrae, which can be grouped into one of five regions (cervical, thoracic, lumbar, sacral, and coccygeal). Moving down the spine, there are generally seven cervical vertebrae, twelve thoracic vertebrae, five lumbar vertebrae, five sacral vertebrae, and four coccygeal vertebrae. The vertebrae of the cervical, thoracic, and lumbar regions of the spine are typically separate throughout the life of an individual. In contrast, the vertebra of the sacral and coccygeal regions in an adult are fused to form two bones, the five sacral vertebrae which form the sacrum and the four coccygeal vertebrae which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Spinal fusion is one such method. In spinal fusion, one or more of the vertebra of the spine are united together ("fused") so that motion no longer occurs between them. Thus, spinal fusion is the process by which the damaged disc is replaced and the spacing between the vertebrae is restored, thereby eliminating the instability and removing the pressure on neurological elements that cause pain.

Spinal fusion can be accomplished by providing an intervertebral implant between adjacent vertebrae to recreate the natural intervertebral spacing between adjacent vertebrae. Once the implant is inserted into the intervertebral space, osteogenic substances, such as autogenous bone graft or bone allograft, can be strategically implanted adjacent the implant to prompt bone in-growth in the intervertebral space. The bone ingrowth promotes long-term fixation of the adjacent vertebrae. Various posterior fixation devices (e.g., fixation rods, screws etc.) can also be utilize to provide additional stabilization during the fusion process.

Notwithstanding the variety of efforts in the prior art described above, these intervertebral implants and techniques are associated with another disadvantage. In particular, these techniques typically involve an open surgical procedure, which results in higher cost, lengthy in-patient hospital stays and the pain associated with open procedures. In addition, many intervertebral implants are inserted anteriorly while posterior fixation devices are inserted posteriorly. This results in additional movement of the patient. Therefore, there remains a need in the art for an improved apparatus and method for introducing an intervertebral implant.

SUMMARY

One embodiment comprises an intervertebral implant that includes a first body portion comprising a first member, a second member, and a first joint portion. A first shaft is provide such that the first member and the second member are pivotable around the shaft. A second body portion comprises a first member, a second member, and a second joint portion. A second shaft is provided and the first member of the second body portion and the second member of the second body portion are pivotable around the shaft. The first joint portion is removably connected to the second joint portion.

Any of the implant features described in the specification can be included in any embodiment. For example, the first and second body portions can include one or more aperture, one or more textured surfaces, and/or a bioactive coating. The one or more textured surfaces can include a ribbed surface, spikes, or other features to engage or anchor the implant into the bone and resist movement. In certain aspects, the first joint portion and the second joint portion form a ball and socket joint. In certain aspects, the implant includes one or more depressions configured for interaction with a deployment tool.

Another embodiment comprises an intervertebral implant that includes a body portion including a first member and a second member. The first body portion includes an open configuration and a closed configuration. A shaft extends through the first body portion and the first member of the first body portion and the second member are pivotable around the shaft from the closed configuration to the open configuration. The body portion includes a motion limiting portion to limit rotational movement of first member relative to the second member when the body portion is in the open configuration.

Any of the implant features described in the specification can be included in any embodiment. For example, the first member can be configured to translate along a central axis of the shaft. In certain aspects, one or more surfaces of the body portion can include a textured surface, one or more apertures, and/or a bioactive coating. The textured surface can include a ribbed surface, spikes, or other features to engage or anchor the implant into the bone and resist movement. In certain aspects, the body portion can include one or more depressions configured for interaction with a deployment tool. In certain aspects, the body portion can include a spring-loaded mechanism capable of transitioning the body portion from the closed configuration to the open configuration.

Another embodiment comprises a method of performing orthopedic surgery. The method includes engaging a first body portion with a deployment tool, delivering the first body portion into an intervertebral space; and transitioning the first body portion from a closed configuration to an open configuration.

Any of the method steps described in the specification can be included in any embodiment. For example, delivering the first body portion can include delivering the first body portion through a posterolateral approach. In certain aspects, delivering the first body portion through the posterolateral approach can include delivering the first body portion through a Kambin's triangle. In certain aspects, the method can include: engaging a second body portion with the deployment tool; delivering the second body portion into the intervertebral space; and transitioning the second body portion from a closed configuration to an open configuration. In certain aspects, the method can include connecting a first joint portion of the first body portion to a second joint portion of the second body portion.

For purposes of summarizing the disclosure, certain aspects, advantages and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 9 is a perspective view of the dilation introducer of FIG. 7A, with the third dilator tube introduced over the second dilator tube.

FIGS. 10A-10D show another embodiment in which a trocar is used in place of the first dilator tube.

FIG. 15C is an enlarged detail view of the proximal end of the second dilator tube shown in FIG. 15A.

FIG. 16B is an enlarged detail view of the distal end of the third dilator tube shown in FIG. 16A.

FIG. 17B is an enlarged detail view of the distal end of the access cannula shown in FIG. 17A.

FIG. 19B is an enlarged detail of the longitudinal cross-sectional view shown in FIG. 19A.

FIG. 20C is an enlarged detail view of a distal tip of a neuro-monitoring needle of FIG. 20A.

FIG. 30 is a side cross-sectional view of the deployment tool shown in FIG. 38 wherein an expandable implant is attached to a distal end thereof.

DETAILED DESCRIPTION

In accordance with certain embodiments disclosed herein, an improved apparatus for inserting an intervertebral implant is provided. For example, in one embodiment, the apparatus may be used to insert surgical instruments and/or one or more intervertebral implants through a minimally invasive procedure to reduce trauma to the patient and thereby enhance recovery and improve overall results. By minimally invasive, Applicant means a procedure performed percutaneously through an access device in contrast to a typically more invasive open surgical procedure.

Certain embodiments disclosed herein are discussed in the context of an intervertebral implant and spinal fusion because of the device and methods have applicability and usefulness in such a field. The device can be used for fusion, for example, by inserting an intervertebral implant to properly space adjacent vertebrae in situations where a disc has ruptured or otherwise been damaged. "Adjacent" vertebrae can include those vertebrae originally separated only by a disc or those that are separated by intermediate vertebra and discs. Such embodiments can therefore be used to create proper disc height and spinal curvature as required in order to restore normal anatomical locations and distances. However, it is contemplated that the teachings and embodiments disclosed herein can be beneficially implemented in a variety of other operational settings, for spinal surgery and otherwise.

Certain embodiments disclosed herein are discussed in the context of an intervertebral implant that can preserve at least some degree of motion between two adjacent vertebrae. In one arrangement, the intervertebral implant is configured to be inserted through the Kambin triangle (as described below) in a reduced cross-sectional profile. Once the implant is passed through the Kambin triangle, the implant can be converted into a second, larger cross-sectional profile in which the device can engage and maintain separation of the adjacent vertebra while still allowing least some degree of motion between two adjacent vertebrae.

Figure 1:
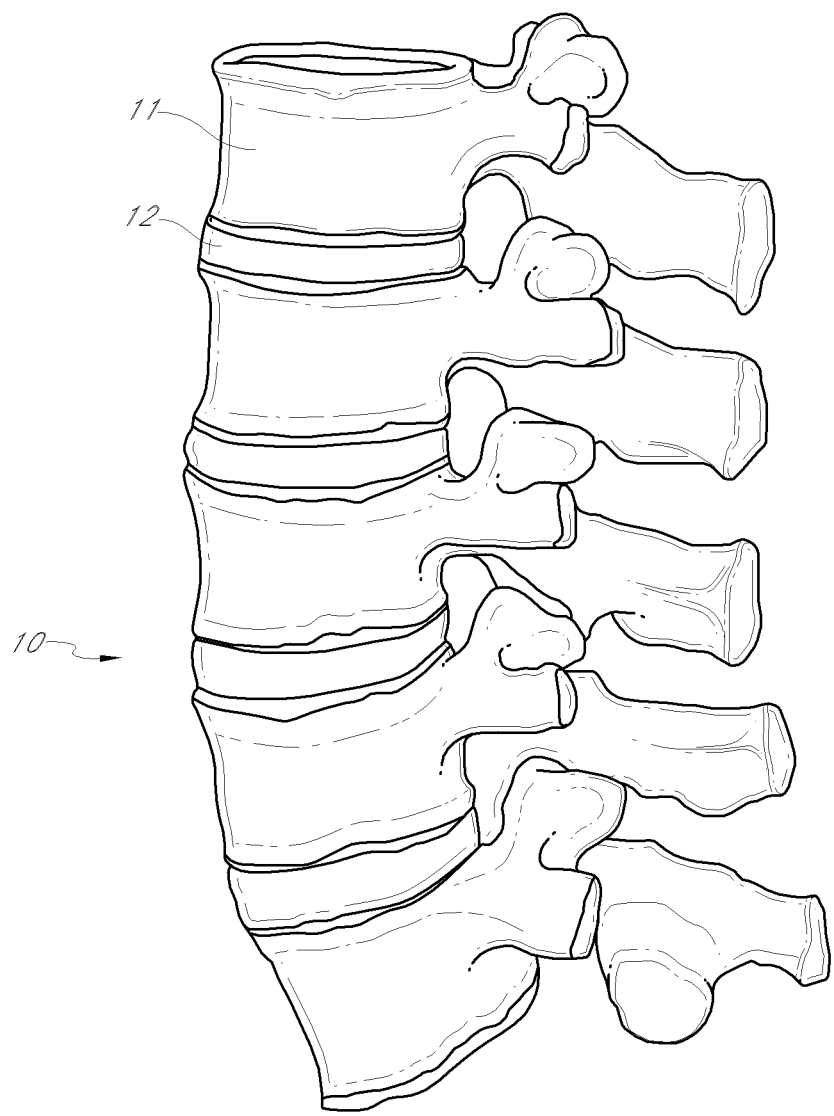
FIG. 1 is a lateral elevational view of a portion of a vertebral column.

As context for the methods and devices described herein, FIG. 1 is a lateral view of a vertebral column 10. As shown in FIG. 1, the vertebral column 10 comprises a series of alternative vertebrae 11 and fibrous intervertebral discs 12 that provide axial support and movement to the upper portions of the body. The vertebral column 10 typically comprises thirty-three vertebrae 11, with seven cervical (C1-C7), twelve thoracic (T1-T12), five lumbar (L1-L5), five fused sacral (S1-S5), and four fused coccygeal vertebrae.

Figure 2:
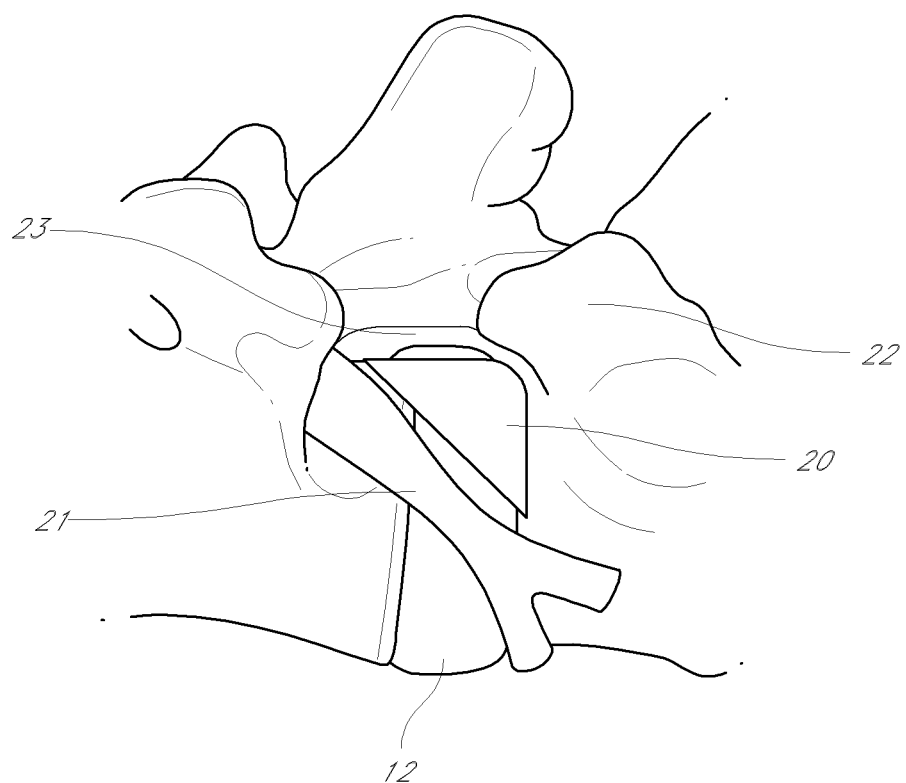
FIG. 2 is a schematic side view of Kambin's triangle.

FIG. 2 is a schematic view of Kambin's triangle. This region 20 is the site of posterolateral access for spinal surgery. It can be defined as a right triangle over the intervertebral disc 12 viewed dorsolaterally. The hypotenuse is the exiting nerve 21, the base is the superior border of the inferior vertebra 22, and the height is the traversing nerve root 23. As will be explained below, in one embodiment, the intervertebral disc 12 is accessed through this region by performing a foraminoplasty in which a portion of the inferior vertebra is removed such that surgical instruments or implants can be introduced at this region of the spine. In such a procedure, it is often desired to protect the exiting nerve and the traversing nerve root. Apparatuses and methods for accessing the intervertebral disc through Kambin's triangle may involve performing endoscopic foraminoplasty while protecting the nerve will be discussed in more detail below. Utilizing foraminoplasty to access the intervertebral disc through Kambin's triangle can have several advantages (e.g., less or reduced trauma to the patient) as compared to accessing the intervertebral disc posteriorly or anteriorly as is typically done in the art. In particular, surgical procedures involving posterior access often require removal of the facet joint. For example, transforaminal interbody lumbar fusion (TLIF) typically involves removal of one facet joint to create an expanded access path to the intervertebral disc. Removal of the facet joint can be very painful for the patient, and is associated with increased recovery time. In contrast, accessing the intervertebral disc through Kambin's triangle may advantageously avoid the need to remove the facet joint. As described in more detail below, endoscopic foraminoplasty may provide for expanded access to the intervertebral disc without removal of a facet joint. Sparing the facet joint may reduce patient pain and blood loss associated with the surgical procedure. In addition, sparing the facet joint can advantageously permit the use of certain posterior fixation devices which utilize the facet joint for support (e.g., trans-facet screws, trans-pedicle screws, and/or pedicle screws). In this manner, such posterior fixation devices can be used in combination with interbody devices inserted through the Kambin's triangle.

Dilation Introducer

FIGS. 2-7B illustrate an embodiment of a dilation introducer 100 that can be used to perform percutaneous orthopedic surgery. As will be described in detail below, the dilation introducer in the illustrated embodiments can comprise an access cannula 30, and a first, second and third dilator tubes 40, 45, 60. While the illustrated embodiment includes first, second and third dilator tubes 40, modified embodiments can include more or less dilator tubes and/or dilator tubes with modified features. It is also anticipated that in some embodiments, the access cannula 30 can be eliminated from the introducer or modified.

Figure 3:
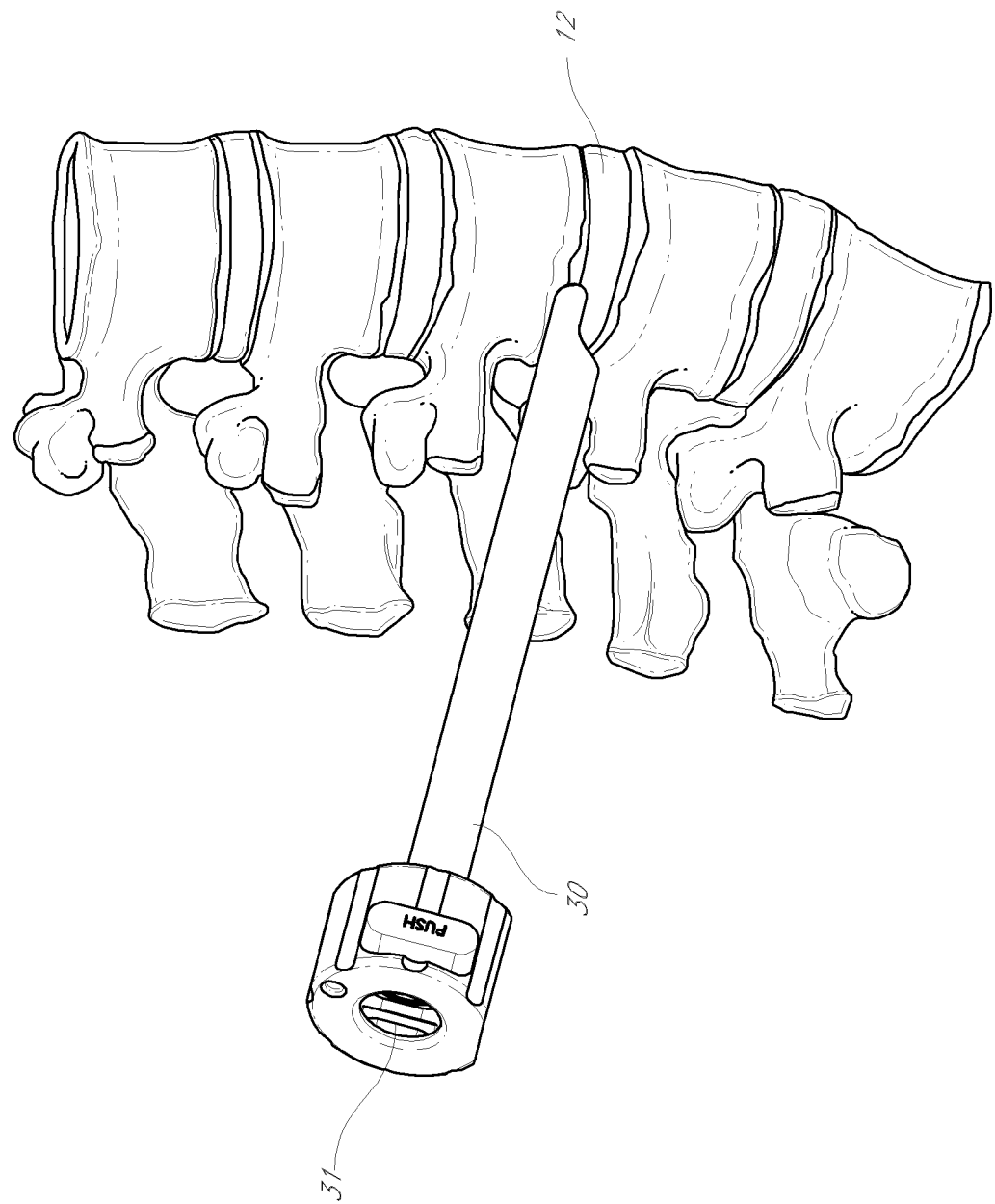
FIG. 3 is a perspective view of an access cannula in positioned against a vertebral column.

FIG. 3 illustrates an embodiment of the access cannula 30, which is shown in a position for performing surgery on an intervertebral disc, for instance transforaminal lumbar interbody fusion. The access cannula 30 in the illustrated embodiment has an inner lumen 31 that allows for surgical instruments and devices to pass through it to access the intervertebral disc 12. The distal tip of the cannula can be oriented such that surgical instruments have access to the intervertebral disc without contacting with the exiting nerve. The position shown in FIG. 3 can be achieved by following the method disclosed herein, discussed in more detail below.

Figure 4A:
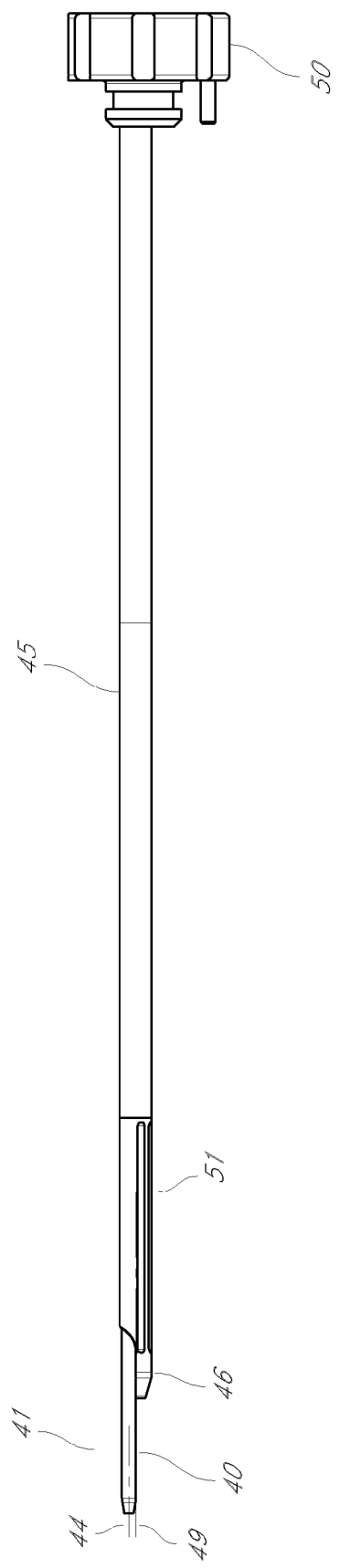
FIG. 4A is a plan view of a first and second dilator tubes in a combined position.
Figure 4B:
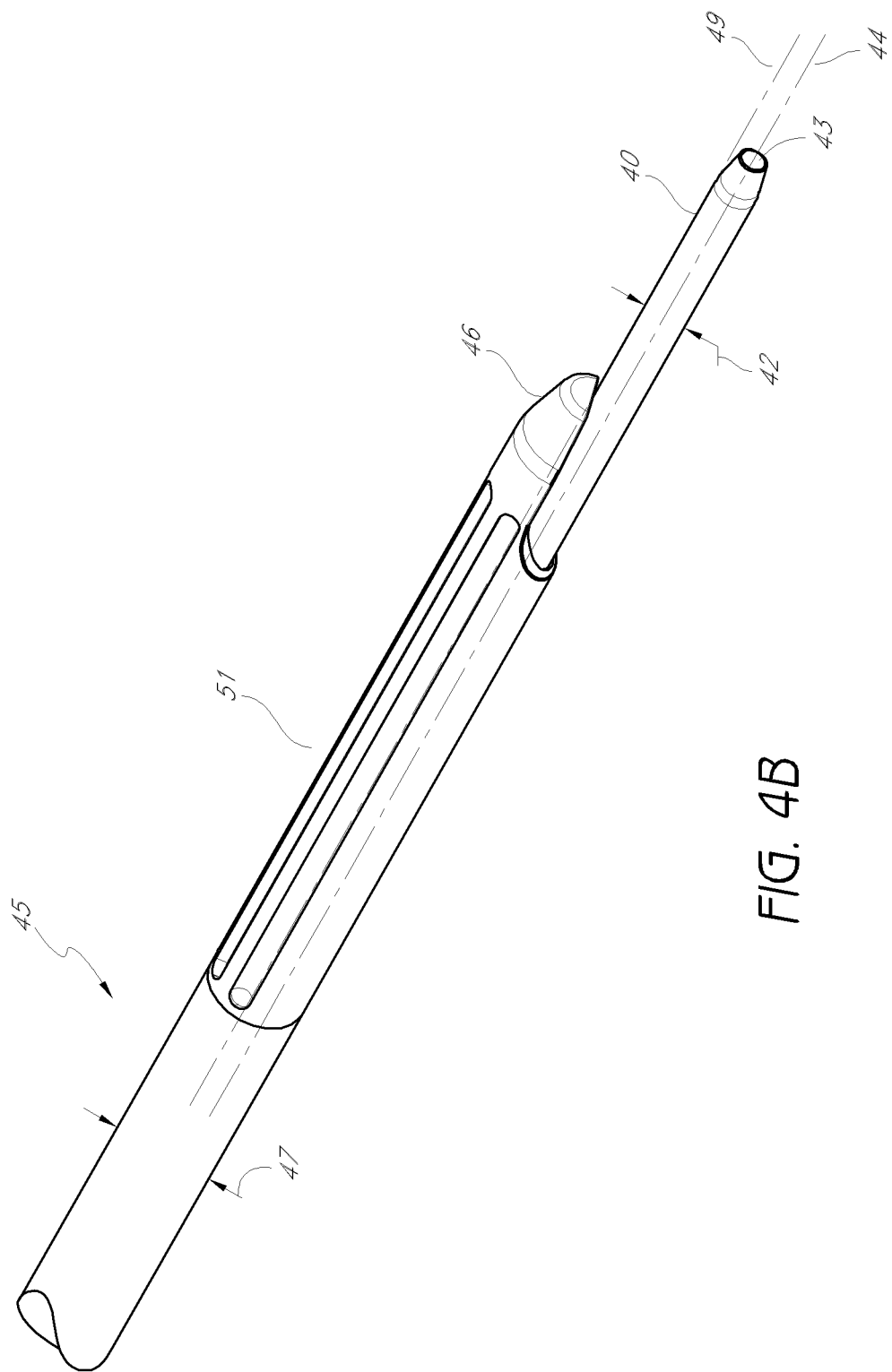
FIG. 4B is an enlarged detail view of the distal tip of the first and second dilator tubes shown in FIG. 4A.

FIGS. 4A and 4B illustrate an embodiment of the first dilator tube 40 and second dilator tube 45 of the dilation introducer 100. As shown, in the illustrated embodiment, the first dilator tube 40 has a distal portion 41, an outer radius 42 and a first longitudinal lumen 43. The illustrated second dilator tube 45 has a distal portion 46, an outer radius 47 and a second longitudinal lumen 48. As shown, the first dilator tube can be received within the lumen of the second dilator tube. The outer radius 42 of the first dilator tube can be centered around a first longitudinal axis 44. The outer radius 47 of the second dilator tube can be centered around a second longitudinal axis 49. In the illustrated embodiment, the second longitudinal axis 49 is laterally offset from the first longitudinal axis 44. In the configuration shown, the outer radius of the first dilator tube is nearly equivalent to the inner radius of the second longitudinal lumen such that the first dilator tube can be slidably received within the second dilator tub. The second dilator tube 45 can include a handle 50 for rotating the tube independently of the first dilator tube 40. In the illustrated embodiment, a collar can be located distal to the handle, with an outer radius larger than the outer radius of the second dilator tube, but smaller than the outer radius of the handle. In a modified embodiment, the first dilator tube 40 can also a separate handle which can be locked together with the handle 50 of the second dilator tube 45. In one embodiment, the first and second dilator tubes 40, 45 can locked longitudinally locked together, such that slidable movement of the first tube with respect to the second is restricted. In one embodiment, the distal portion 46 of the second dilator tube has a flattened edge. This flattened edge advantageously prevents the second dilator tube 45 from penetrating the disc.

FIG. 4B shows an enlarged detail view of the distal portions of the first and second dilator tubes 40, 45 of FIG. 4A. The distal portion 46 of the second dilator tube 45 can have a generally semi-annular cross-section, configured such that when the first dilator tube 40 is received within the second dilator tube 45, the outer radial surface of the first dilator tube 40 is partially exposed at the distal portion 46 of the second dilator tube 45. The opening of the generally semi-annular cross-section of the second dilator tube can be oriented opposite the second longitudinal axis 49 with respect to the first longitudinal axis 44. Additionally, the second dilator tube can include cutting flutes or ridges 51 on one side, located opposite the opening of the generally semi-annular cross-section of the second dilator tube 45. In other embodiments, the cutting flutes may be replaced with a coarse surface (e.g., knurling, sharp edges, abrasive members, etc.) which, when rotated or slid (e.g., back and forth) against bone, will create a recess therein. As noted above, other mechanisms for removing bone can be used, and the cutting flutes are shown here by way of example only. As can be seen in FIG. 4B, the inner lumen of the second dilator tube 45 can be off-center. In this configuration, the cutting flutes 51 are further from the axis of rotation than the side opposite the cutting flutes. This is particularly advantageous for performing foraminoplasty while protecting the exiting nerve, as will be discussed in more detail below.

Although the illustrated embodiment depicts the first and second dilator tubes as separate elements, in alternative embodiments these two tubes can be coupled formed together as one unified dilator tube with a staggered distal portion. In still other embodiments, the first dilator tube and second dilator tube may be coupled together to form a single component. The tubes may be joined by, for instance, welding, adhesive, mechanical joints, or any other appropriate means.

In another alternative embodiment, the first dilator tube may be omitted. Instead, a Jamshidi® needle with a removable handle, or a similar device, may be used to initially define a path to the intervertebral disc. With the handle of the Jamshidi® needle removed, the second dilator tube may be advanced over the Jamshidi® needle, just as with the first dilator tube. In some embodiments, a K-wire or similar device can be inserted through the Jamshidi® needle and/or dilator tubes.

Figure 5A:
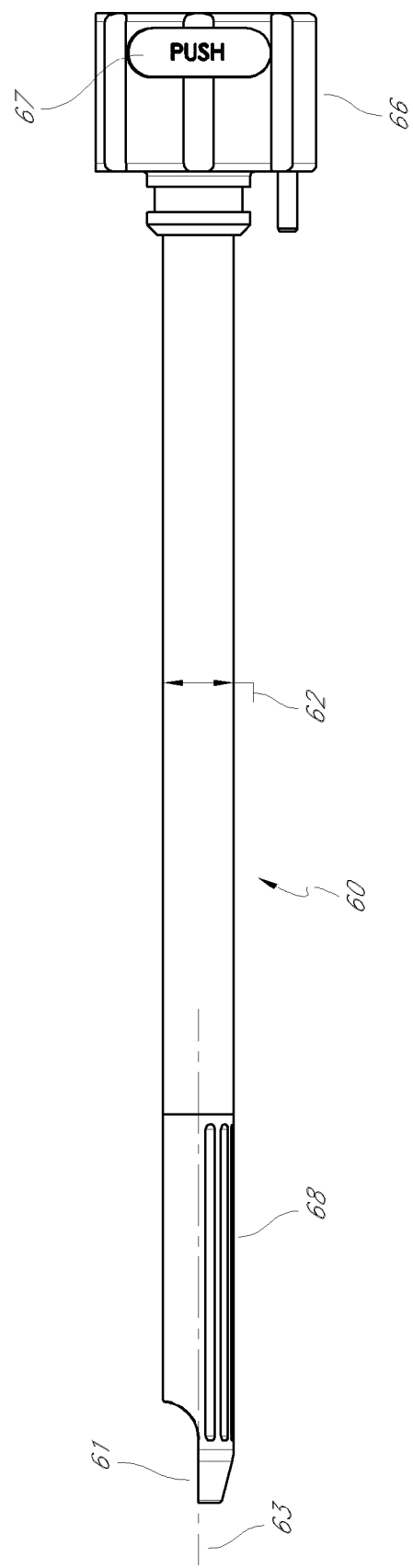
FIG. 5A is a plan view of a third dilator tube.
Figure 5B:
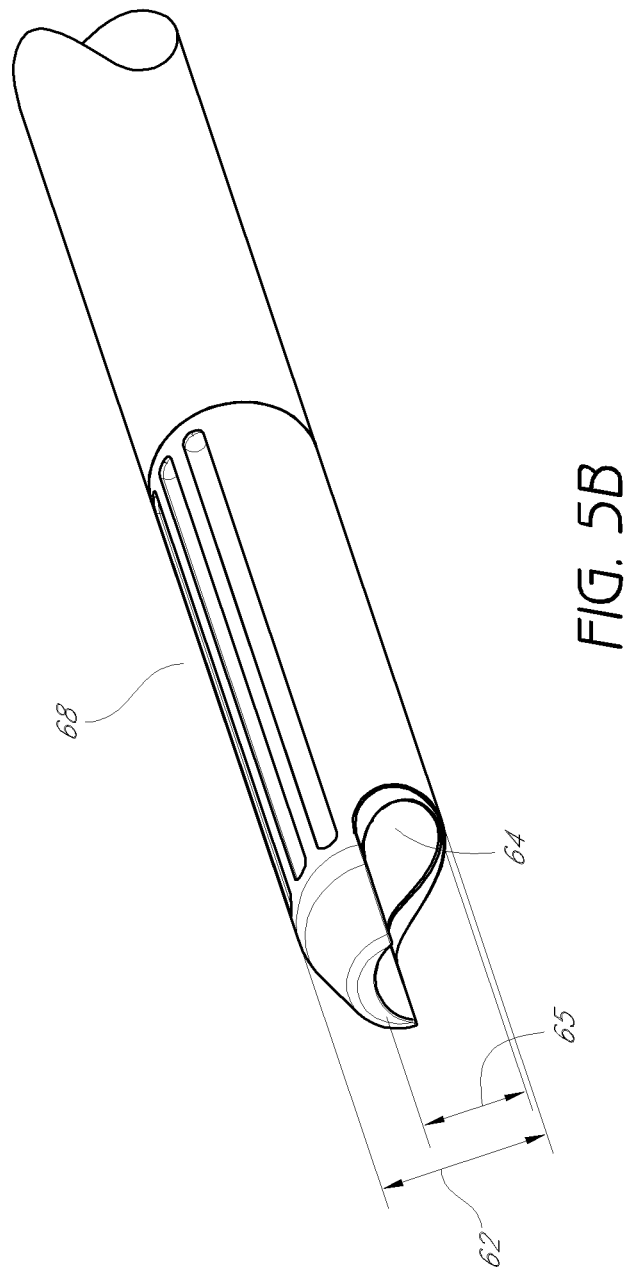
FIG. 5B is an enlarged detail view of the distal tip of the third dilator tube shown in FIG. 5A.

FIGS. 5A and 5B illustrate and embodiment of the third dilator tube 60, which can be configured to be slidably introduced over the second dilator tube 45. The third dilator tube 60 can include a distal portion 61, a third outer radius 62 centered around a third longitudinal axis 63, and a third longitudinal lumen 64 having a third inner radius 65. The third lumen 64 can be configured to removably receive the second dilator tube (not shown) for slidable movement within the third lumen 64. In such a configuration, the third longitudinal axis 63 is parallel to and laterally offset from the second longitudinal axis 49. A handle 66 can allow for rotation of the third dilator tube. In one arrangement, a collar can be located distal to the handle 66, with an outer radius larger than the outer radius of the third dilator tube 45, but smaller than the outer radius of the handle.

In some embodiments, a button 67 on the handle 66 allows for the operator to toggle between a locked and unlocked configuration. In a locked configuration, the second and third dilator tubes are unable to slide relative to one another. In an embodiment, the locked configuration permits the dilator tubes to rotate independently with respect to one another. In another embodiment, the locked configuration restrains rotational movement as well as slidable movement. The button 67 may comprise a generally rectangular shape with a cut-out large enough for the collar of the second dilator tube 45 to pass therethrough. A spring located underneath the button 67 provides upward pressure on the button. When uncompressed, the cut-out portion of the button presses firmly against the collar of the second dilator tube 45, which may be received within the handle 66 of the third dilator tube. When uncompressed, the friction of the button 67 against the collar inhibits movement of the third dilator tube 60 with respect to the second dilator tube. In some embodiments, the cut-out portion of the button may form a notch configured to fit within the ridge on the collar of the third dilator tube. Upon compressing the button 67, the cut-out portion of the button may be moved away from the collar, permitting free movement of the third dilator tube 60 relative to the second dilator tube 45.

FIG. 5B shows an enlarged detail view of the distal portion of the third dilator tube of FIG. 5A. The distal portion 61 has a generally semi-annular cross-section, and cutting flutes 167 for reaming bone located opposite the opening of the semi-annular cross-section. As with the second dilator tube, in other embodiments the cutting flutes may be replaced or used in combination with a coarse or other cutting or abrading surface which, when rotated or slid against bone, will create a recess therein. As can be seen in FIG. 5B, the inner lumen of the third dilator tube 60 may be off-center. In this configuration, the cutting flutes 68 are further from the axis of rotation than the side opposite the cutting flutes. This is particularly beneficial for performing foraminoplasty while protecting the exiting nerve, as will be discussed in more detail below.

Figure 6A:
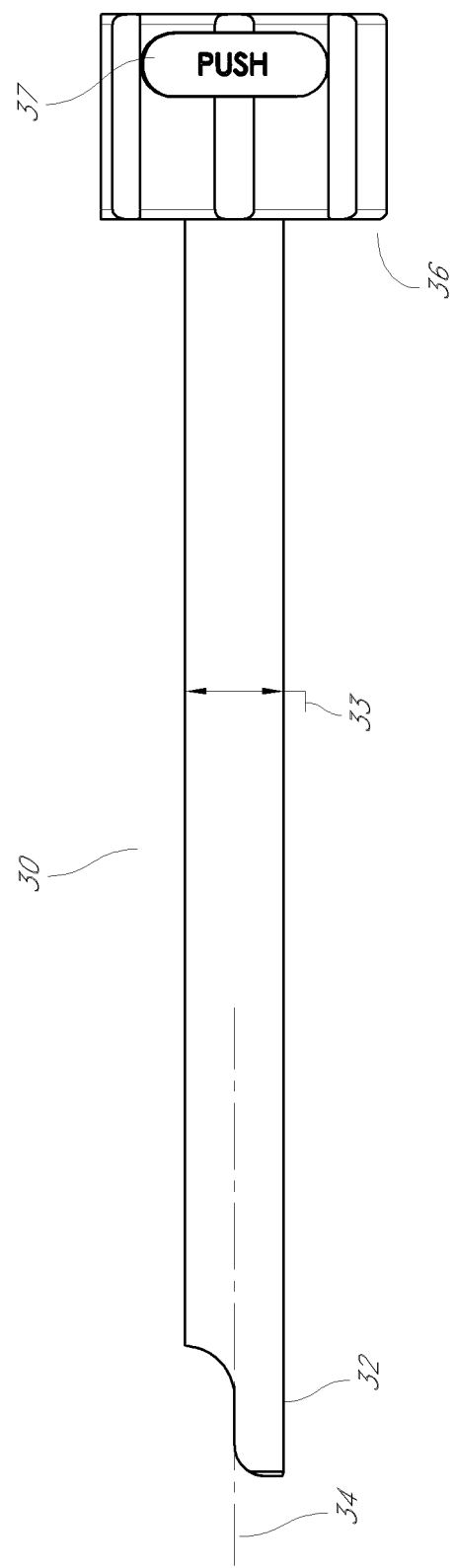
FIG. 6A is a side view of the access cannula shown in FIG. 3.
Figure 6B:
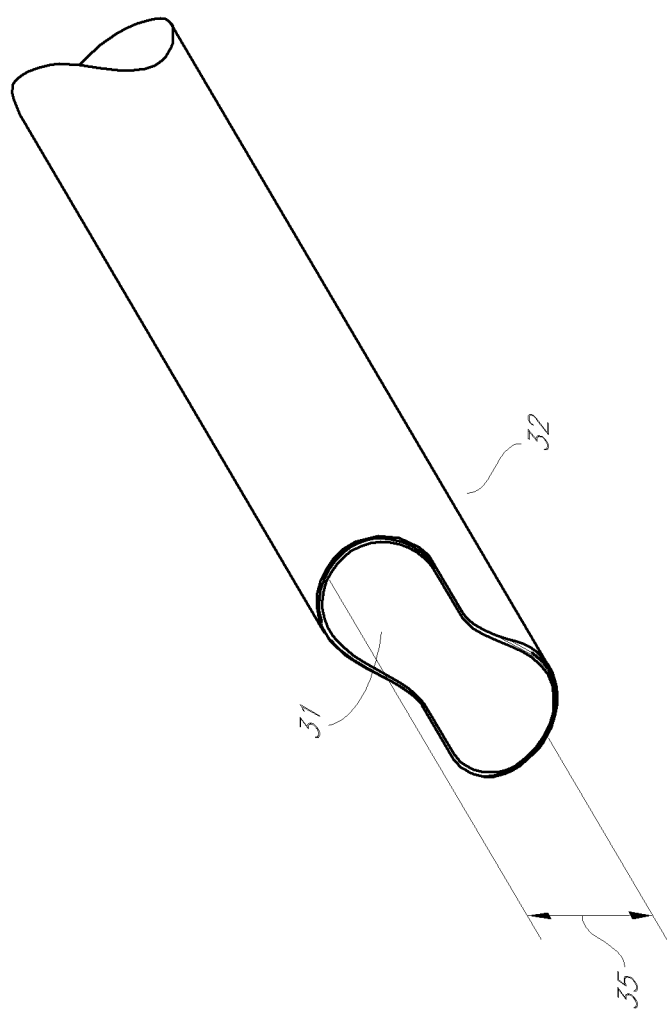
FIG. 6B is an enlarged detail view of the distal tip of the access cannula shown in FIG. 6A.

FIGS. 6A and 6B illustrate an embodiment of the access cannula, which can be configured to be introduced over the third dilator tube (not shown). The access cannula 30 has a distal portion 32, a fourth outer radius 33 centered around a fourth longitudinal axis 34, and a fourth longitudinal lumen 31 having a fourth inner radius 35. The access cannula 30 may be configured to removably receive the third dilator tube (not shown) for slidable movement within the third lumen. A handle allows for rotation of the access cannula 30.

In some embodiments, a button 37 on the handle 36 allows for the operator to toggle between a locked and unlocked configuration. In a locked configuration, third dilator tube and the access cannula are unable to slide relative to one another. In an embodiment, the locked configuration permits the dilator tubes to rotate independently with respect to one another. In another embodiment, the locked configuration restrains rotational movement as well as slidable movement. The button 37 may comprise a generally rectangular shape with a cut-out large enough for the collar of the third dilator tube 60 to pass therethrough. A spring located beneath the button 37 can provide upward pressure on the button. When uncompressed, the cut-out portion of the button can press firmly against the collar of the third dilator tube 45, which may be received within the handle of the access cannula 30. When uncompressed, the friction of the button 37 against the collar can inhibit movement of the access cannula 30 with respect to the third dilator tube 60. Upon compressing the button 37, the cut-out portion of the button can be moved away from the collar, permitting free movement of the access cannula 30 relative to the third dilator tube 60.

FIG. 6B shows an enlarged detail view of the distal portion of the access cannula of FIG. 6A. The distal portion 32 can have a generally semi-annular cross-section. In the embodiment shown, the fourth longitudinal lumen may be centered with respect to the outer radius of the access cannula, in contrast to the second and third dilator tubes. In other embodiments, however, the access cannula may also have a longitudinal lumen that may be off-center with respect to the outer radius. In yet another embodiment, the access cannula need not be limited to a cylindrical outer surface. The outer surface could, for instance, have an elliptical, polygonal, or other cross-sectional shape.

Figure 7A:
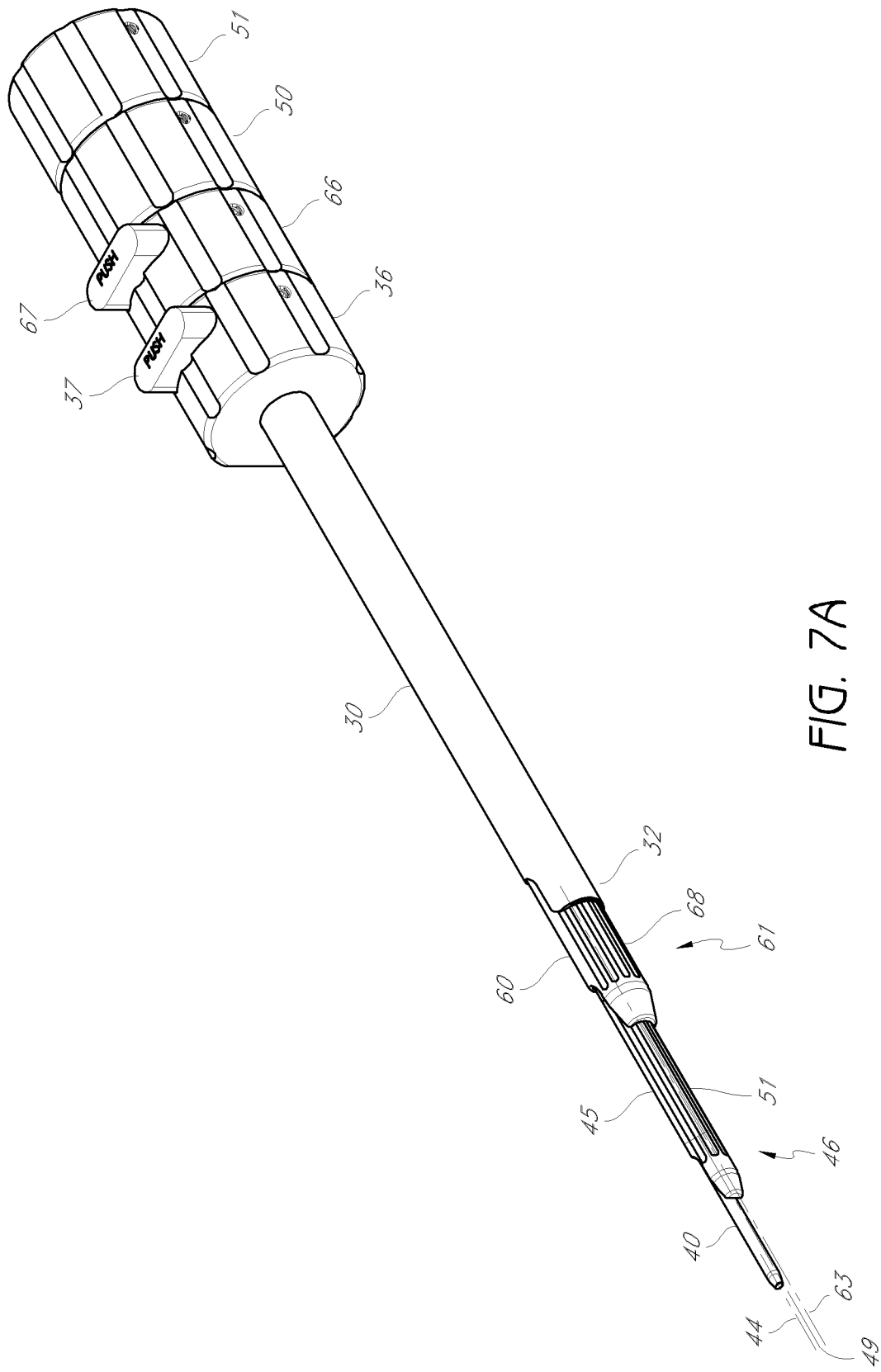
FIG. 7A is a perspective view of a dilation introducer comprising the first and second dilator tubes of FIG. 4A, the third dilator tube of FIG. 5A and the access cannula of FIG. 6A.
Figure 7B:
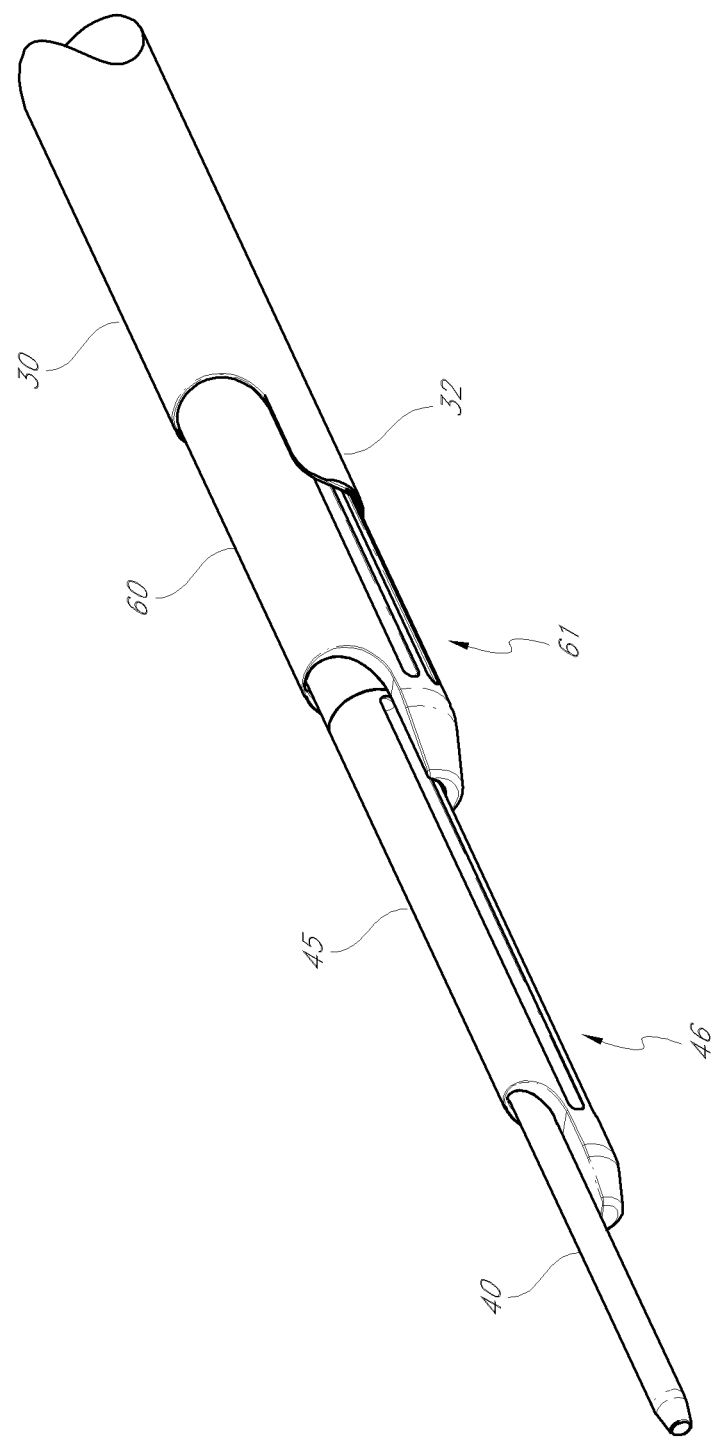
FIG. 7B is an enlarged detail view of the distal tip of dilation introducer shown in FIG. 7A.

FIGS. 7A and 7B illustrate one embodiment of the dilation introducer 100 in an assembled configuration. As shown, the access cannula 30 can be positioned over the third dilator tube 60, which can be positioned over the second dilator tube 45, which in turn can be positioned over the first dilator tube 40. The handles 50, 151 of the first and second dilator tubes can be locked together to constrain slidable movement, but allow for the second dilator tube 45 to rotate with respect to the first dilator tube 40. The third dilator tube 60 can be advanced distally until the distal portion 61 of the third dilator tube aligns with the distal portion 46 of the second dilator tube. Further, the access cannula may also be advanced so that the distal portion 32 aligns with the distal portions 46, 61 of the second and third dilator tubes. The second and third dilator tubes 45, 60 each have cutting flutes 51, 68 on their respective distal portions 46, 61. As can be seen, the first, second, and third longitudinal axes 44, 49, 63 are each laterally offset from one another.

In certain embodiments, the first, second and third dilator tubes along with the access cannula can be provided with additional stops that engage the buttons described above. For example, in one embodiment, notches or detents can be provided that engage the button when one tube is advanced distally and reaches a specific location (e.g., end point). In this manner, forward movement of a tube or cannula can be limited once the tube or cannula may be advanced to a desired location FIG. 7B shows an enlarged detail view of the dilation introducer of FIG. 7A. The distal portions 46, 61, 32 of each of the second and third dilator tubes 45, 60, and of the access cannula 30 have generally semi-annular cross-sections. The distal portions 46, 61 of the second and third dilator tubes in the illustrated embodiment can have flattened edges, to prevent penetration into the intervertebral disc as each dilator tube is advanced.

Method of Use

FIGS. 8A-13 illustrate one embodiment of a method of performing percutaneous orthopedic surgery using the dilation introducer. With initial reference to FIG. 8A, the first dilator tube 40 can be placed through Kambin's triangle 20 until the distal portion 41 abuts or even penetrates the intervertebral disc 12. In one arrangement, the second dilator tube 45 can then be advanced over the first dilator tube 40 until the distal portion 46 of the second dilator tube abuts but does not enter the intervertebral disc 12.

As discussed above, although the illustrated embodiment shows the first and second dilator tubes as separate elements, in alternative embodiments these two tubes may be formed together as one unified dilator tube with a staggered distal portion. In still other embodiments, the first dilator tube and second dilator tube may be coupled together to form a single component. In these alternative embodiments, the unified or coupled dilator tube may be advanced until the more distal portion abuts or penetrates the intervertebral disc.

In another alternative embodiment, the first dilator tube may be omitted. Instead, a Jamshidi® needle with a removable handle or similar device may be used. In such an embodiment, the Jamshidi® needle may be first introduced to abut or enter the intervertebral disc, after which the handle may be removed. Optionally, a K-wire may be inserted into the Jamshidi® needle after it is in position either abutting or partially penetrating the intervertebral disc. The second dilator tube may then be advanced over the Jamshidi® needle.

Figure 8A:
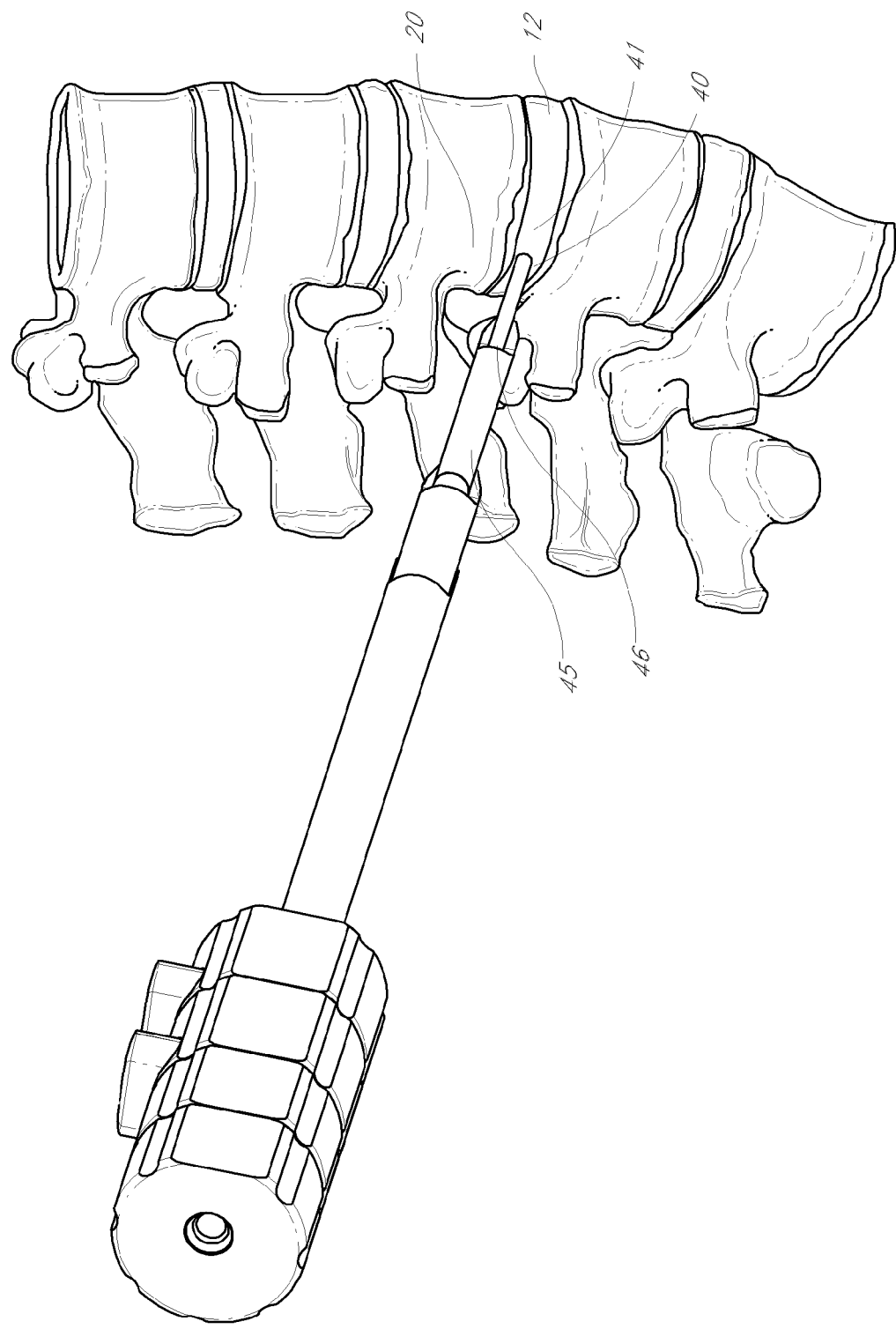
FIG. 8A is a perspective view of the dilation introducer of FIG. 7A positioned against the spine.
Figure 8B:
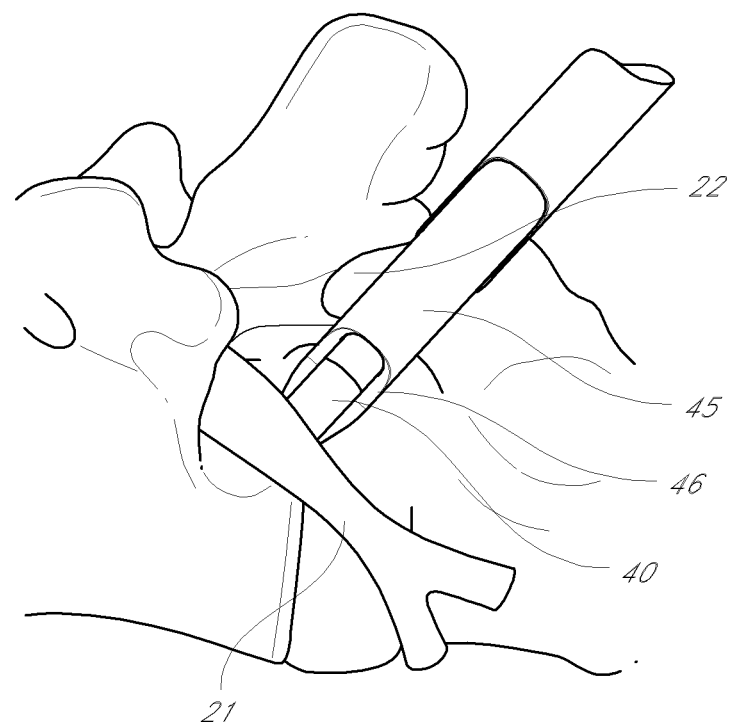
FIG. 8B is an enlarged detail view of the second dilator tube of FIG. 7A introduced over the first dilator tube of FIG. 7A.

FIG. 8B shows an enlarged detail of the second dilator tube 45 introduced over the first dilator tube 40. The distal portion 46 of the second dilator tube 45 can have a semi-annular cross-section with an opening that forms a recess with respect to the leading edge of the tube 45. The second dilator tube 45 can be oriented for advancement over the first dilator tube 40 such that the opening of the semi-annular cross-section faces the exiting nerve 21. This technique advantageously limits and/or eliminates contact with the exiting nerve. The distal portion 46 of the second dilator tube opposite the opening of the semi-annular cross-section abuts the inferior vertebrae 22. The cutting flutes (not shown) are positioned against the inferior vertebrae 22. The second dilator tube 45 may be rotated slightly back and forth, such that the cutting flutes create a recess in the inferior vertebrae 22, making room for introduction of the third dilator tube. When rotating the second dilator tube, care is taken to minimize any trauma inflicted upon the exiting nerve. Accordingly, in the illustrated embodiment, the tube 45 can be used to remove bone on a side of the tube 45 generally opposite of the nerve 21.

With reference now to FIG. 9, the third dilator tube 60 can be introduced over the second dilator tube 45. In one arrangement, the distal portion 61 of the third dilator tube 60 abuts but does not enter the intervertebral disc. In the illustrated embodiment, a flattened edge of the distal portion can help ensure that the third dilator tube 60 does not penetrate the intervertebral disc or limit such penetration. As with the second dilator tube, the opening of the semi-annular cross-section of the distal portion of the third dilator tube can be positioned to face the exiting nerve (not shown). Contact between the third dilator tube 60 and the nerve can thereby be minimized or eliminated. The cutting flutes 68 of the third dilator tube can be positioned opposite the opening of the semi-annular cross-section and abut the inferior vertebrae 22. The third dilator tube 60 may be rotated slightly back and forth, such that the cutting flutes create a further recess in the inferior vertebrae 22, making room for introduction of the access cannula. Again, care should be taken during the rotation of the third dilator tube to ensure that the exiting nerve is not injured thereby. Accordingly, the third dilator tube can be can be used to remove bone on a side of the tube 60 generally opposite of the nerve 21.

FIGS. 10A-D show an alternative method in which a trocar can be used in place of the first dilator tube. In some embodiments, the insertion point and access trajectory can first be determined. For example, a patient may lie face down on a surgical frame to facilitate a lordotic position of the lumbar spine. With aid of a lateral x-ray or other imaging system, a K-wire (or equivalent) can be laid beside the patient and placed to the depth of optimal insertion for the intervertebral implant. Intersection with the skin can be marked on the K-wire (or equivalent). With the aid of an anteroposterior x-ray or other imaging system, the K-wire (or equivalent) can be laid on top of the patient, aligned with the disc in a view that allows for the end plates to be parallel (e.g., Ferguson View or Reverse Ferguson, as applicable). The distance between the midline and the previously marked point on the K-wire can define the insertion point.

Figure 10B:
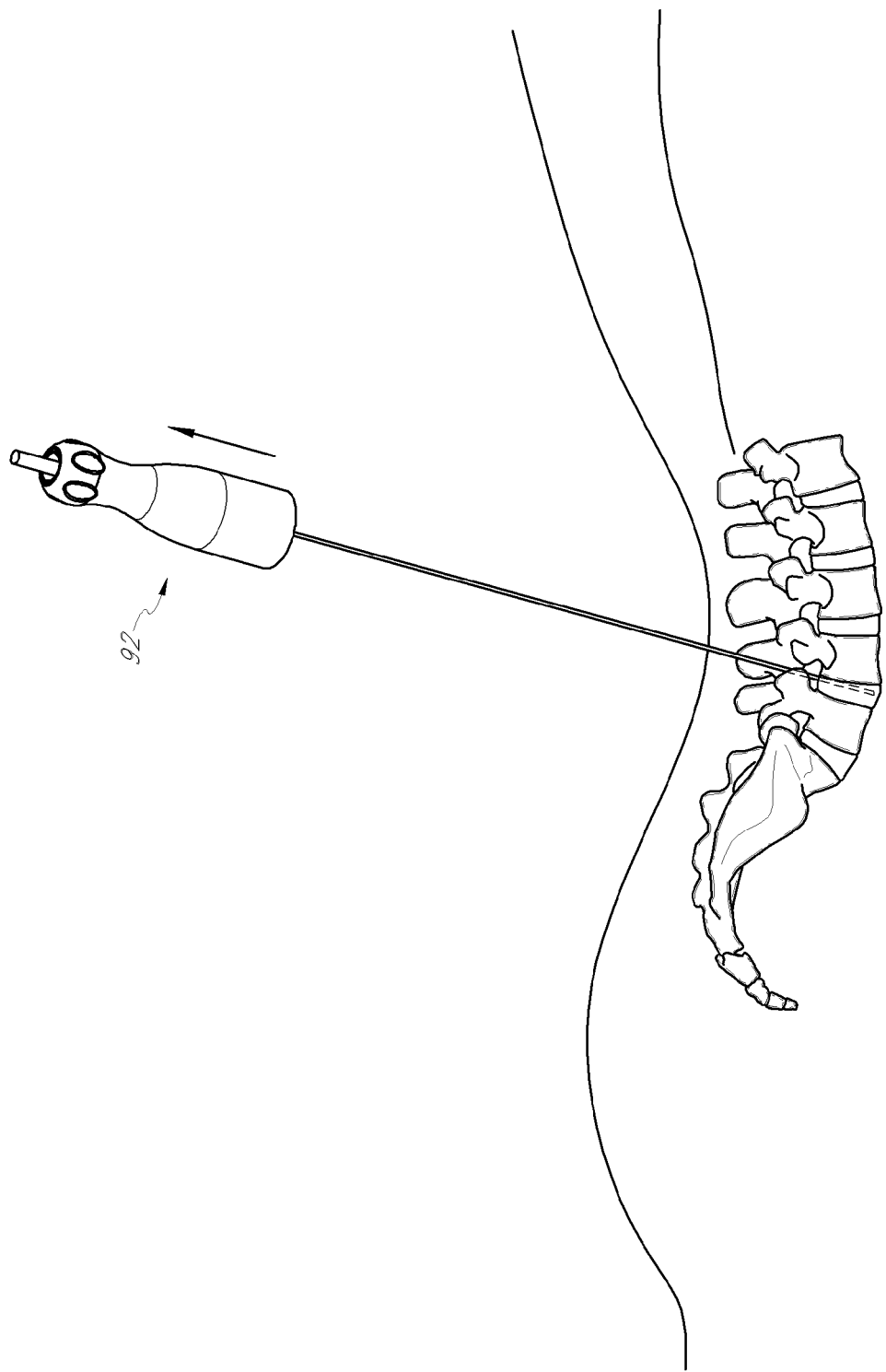
Figure 10C:
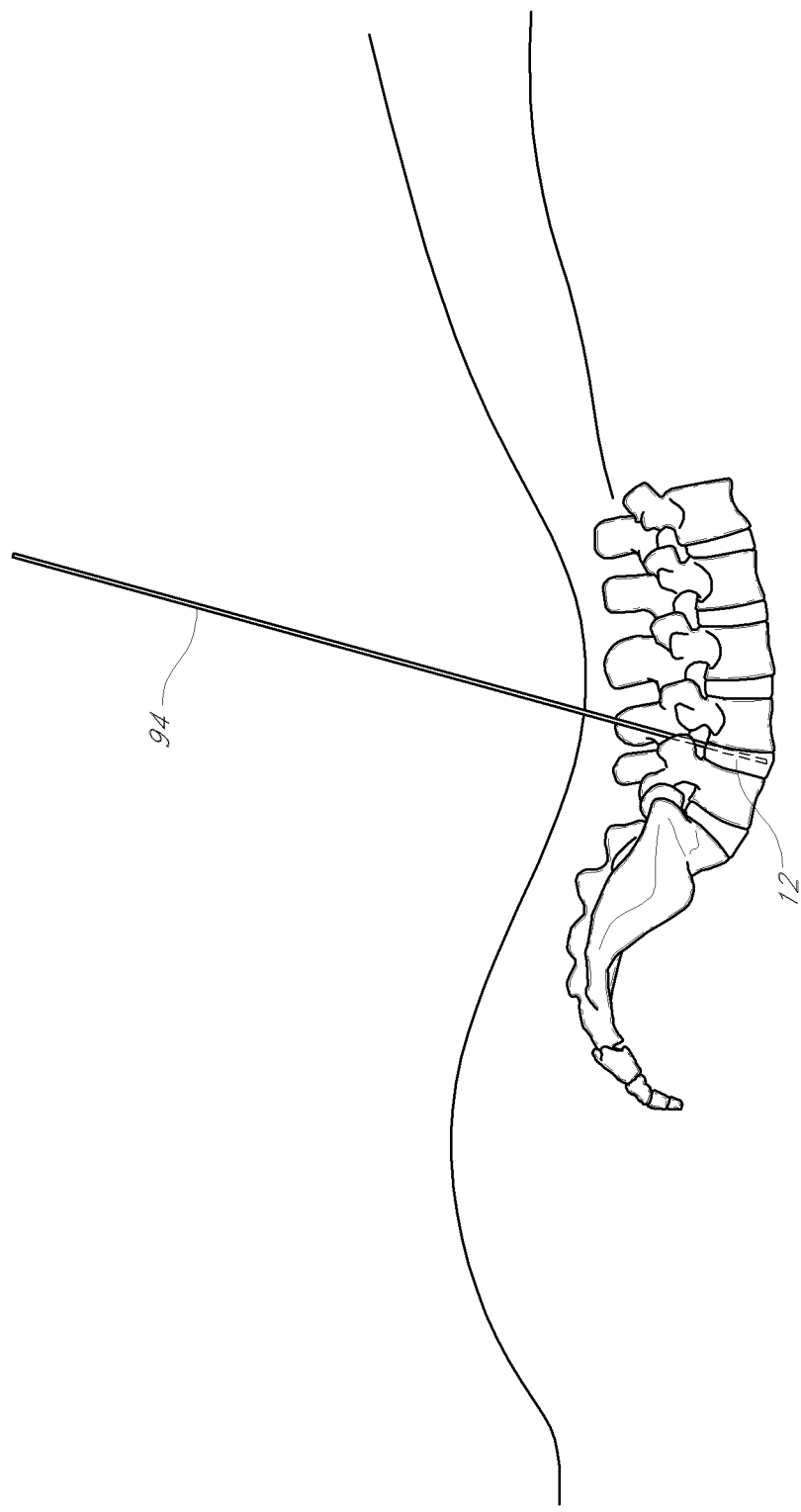
Figure 10D:
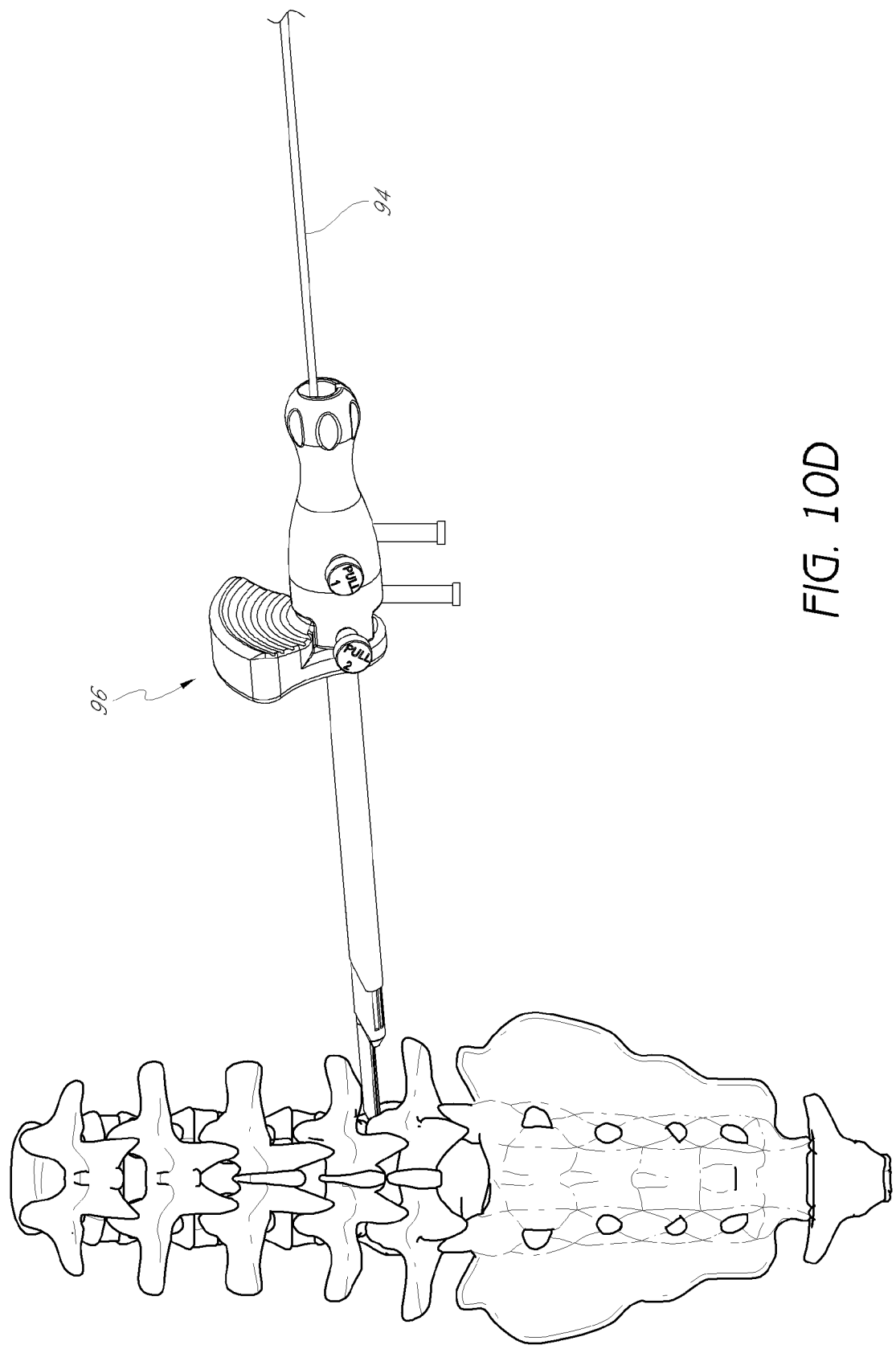

As illustrated in FIG. 10A, a small skin incision can be made defining a trajectory into the disc can be between 45 and 55 degrees. Next, a trocar 90 can be placed into the center of the disc 12 of the level to be treated, up to but not through the distal annulus. Alternatively, an 11 gauge to 18 gauge access needle can be used. As shown in FIGS. 10B-C, the inner stylet 92 of the trocar (if present) can be removed while maintaining the outer sheath 94 in place within the disc 12. Alternatively, a K-wire can be inserted into the disc and the outer sheath may be removed. Next, a dilation introducer 96 can be placed over the outer sheath 94 of the trocar (or over the K-wire, if applicable). The dilation introducer 96 can be aligned so that the smooth edges are oriented towards the exiting nerve root and the foramen. In some embodiments, the dilation introducer 96 can include at least second and third dilator tubes, each having cutting flutes adapted to perform foraminoplasty for improved access to the disc space. In some embodiments, the dilation introducer 96 can function substantially as described elsewhere herein, except that the trocar 90 has replaced the first dilator tube. In some embodiments, the second dilator tubes may be rotated within +/−45 degrees around the longitudinal axis so that the cutting flutes do not contact the exiting nerve.

Figure 11:
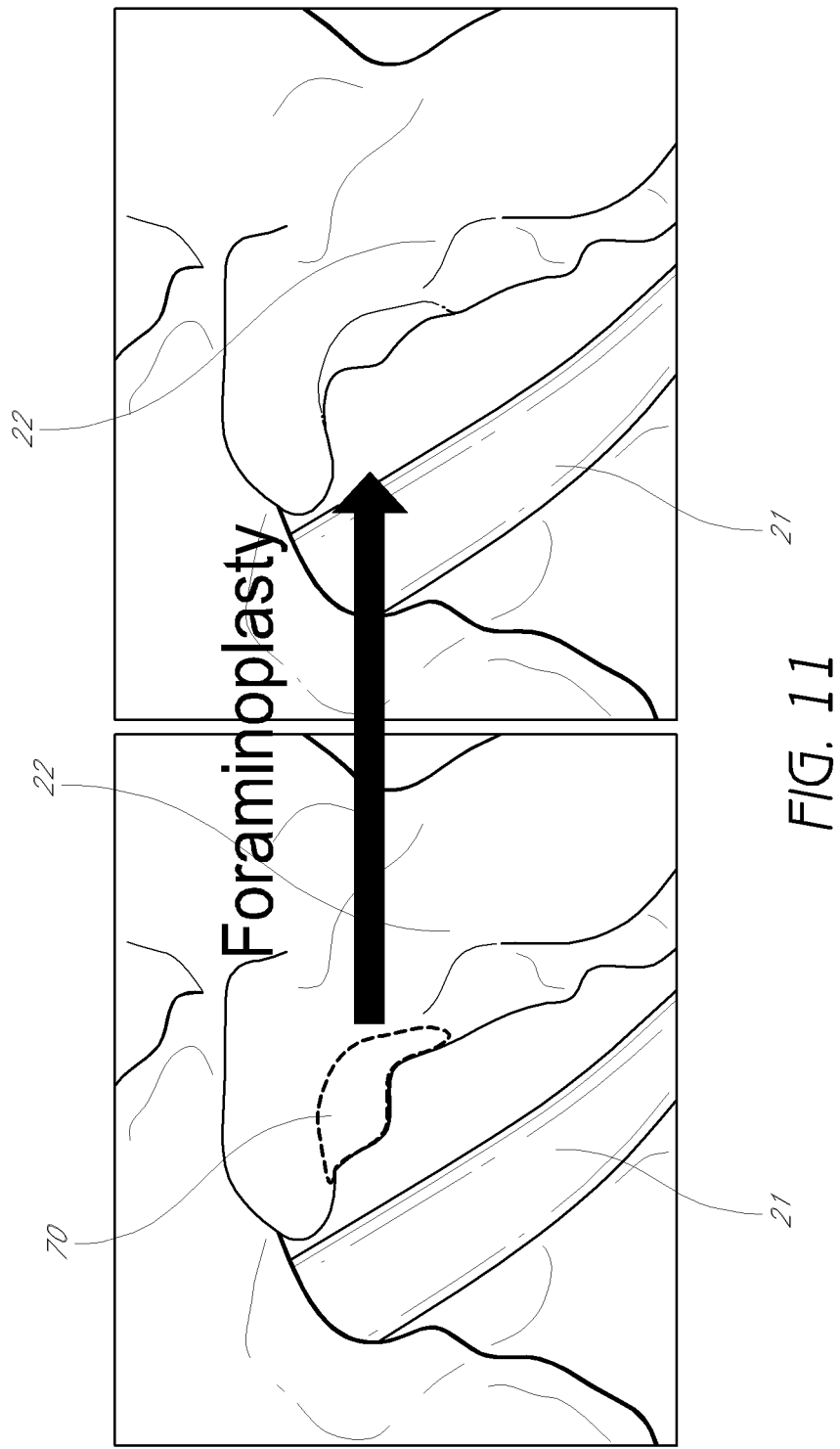
FIG. 11 shows the access point before and after the foraminoplasty performed by the dilation introducer of FIG. 7A.

FIG. 11 shows the access area before and after the second and third dilator tubes 45, 60 are rotated to create a recess in the inferior vertebrae 22. The area 70 in the left image demarcated by a dashed line is the portion of bone that can be removed by the second and third dilation tubes 45, 60. This foraminoplasty permits the access cannula to be introduced without disturbing the exiting nerve 21. The method described is not limited by the precise location of the recess shown in FIG. 11. In general, a recess may be formed anywhere along the superior border of the inferior vertebrae 22, in order to provide improved access for a dilation introducer.

Figure 12A:
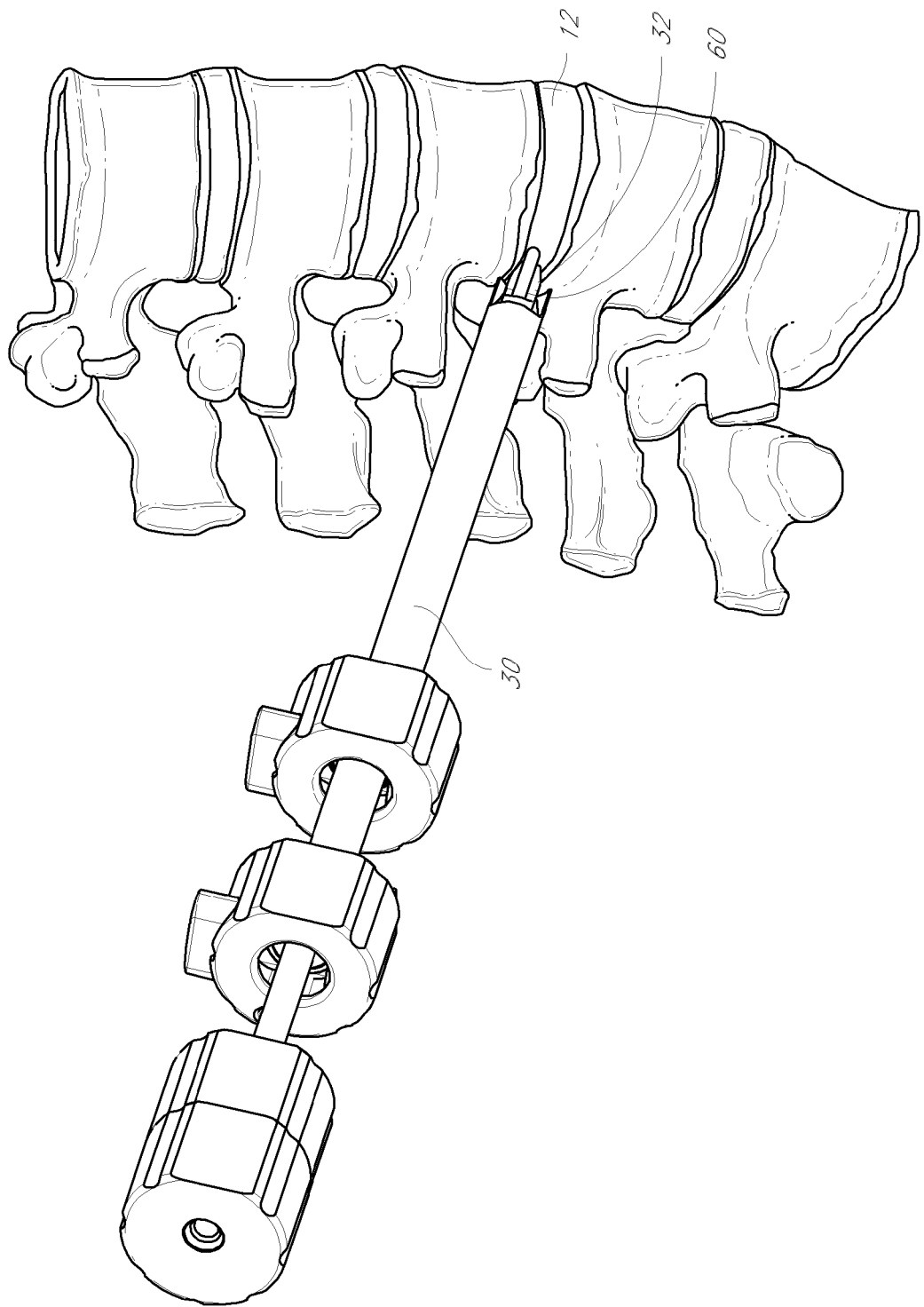
FIG. 12A is a perspective view of the dilation introducer of FIG. 7A, with the access cannula introduced over the third dilator tube.

FIG. 12A shows the access cannula 30 introduced over the third dilator tube 60. The distal portion 32 of the access cannula 30 abuts but does not enter the intervertebral disc 12. In one embodiment, the distal portion 32 can be equipped with flattened edges to guard against insertion into the intervertebral disc. As with the second and third dilator tubes 45, 60, the opening of the semi-annular cross-section of the distal portion 32 of the access cannula 30 can be positioned initially to face the exiting nerve (not shown). Contact between the access cannula 30 and the exiting nerve can thereby be minimized during insertion.

Figure 12B:
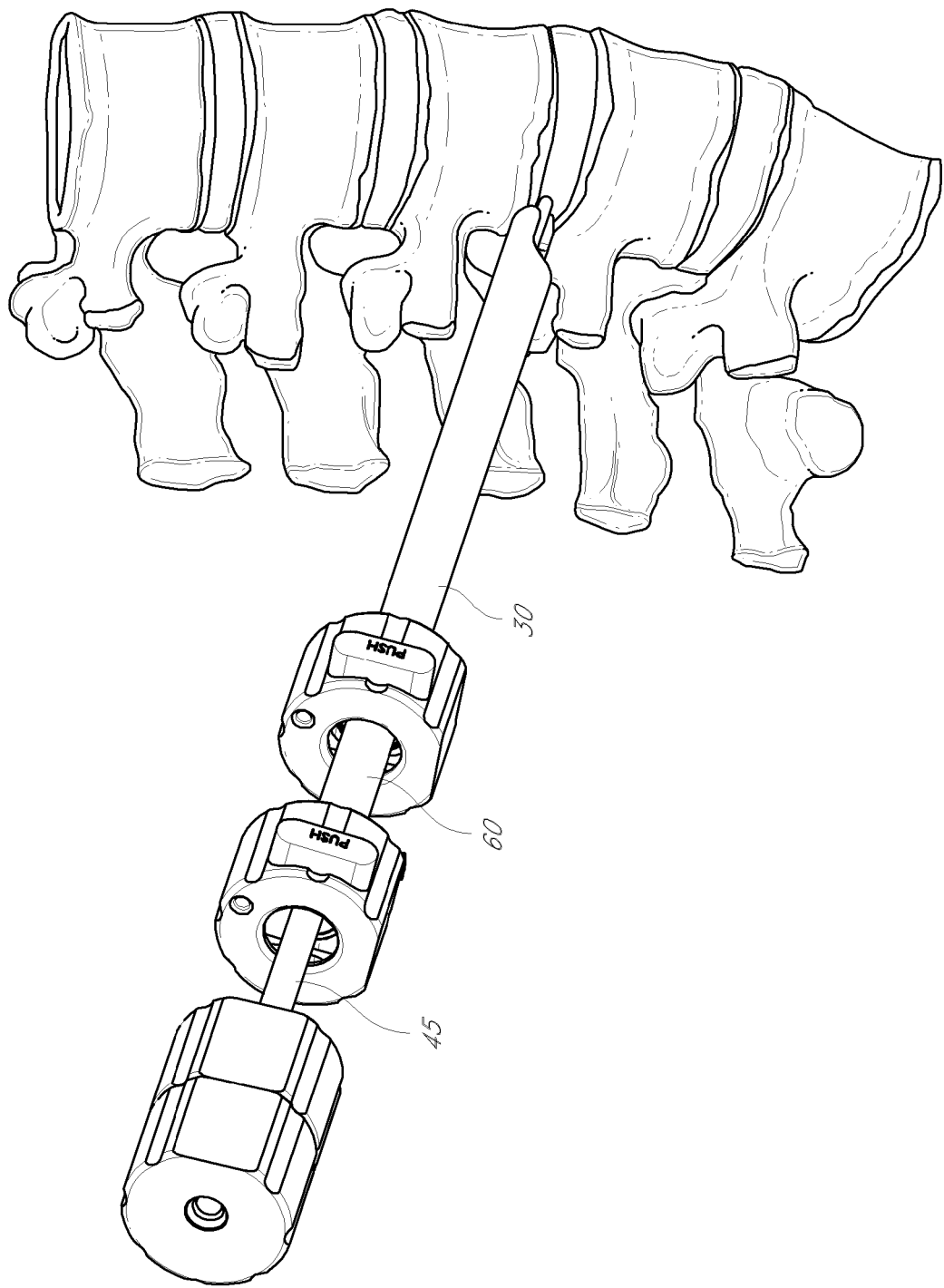
FIG. 12B is a perspective view of the dilation introducer of FIG. 7A, with the access cannula rotated to protect the exiting nerve.

As can be seen in FIG. 12B, the access cannula 30 can then be rotated such that the opening of the semi-annular cross-section faces opposite the exiting nerve (not shown). Since, unlike the second and third dilator tubes 45, 60, the outer surface of the access cannula is smooth, trauma to the exiting nerve may be minimized during this rotation.

Figure 12C:
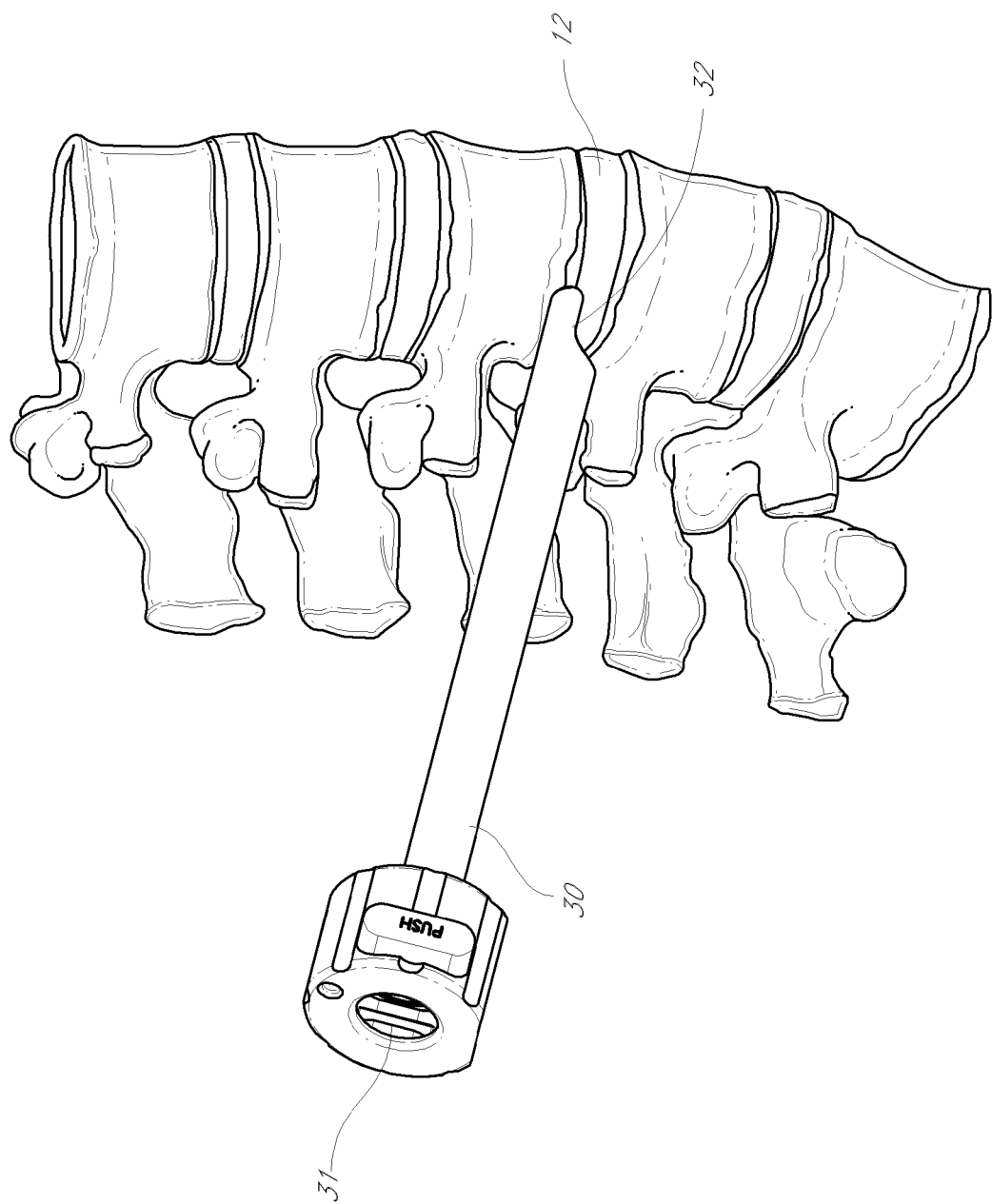
FIG. 12C is a perspective view of the dilation introducer of FIG. 7A, with the first, second, and third dilator tubes removed, while the access cannula remains in place.

Referring now to FIG. 12C, once the access cannula 30 is in position, which in one embodiment comprising until the distal portion 32 abuts the intervertebral disc 12, the cannula 30 can be rotated so that the opening of the semi-annular cross-section faces opposite the exiting nerve (not shown), the first, second, and third dilator tubes 40, 45, 60 may be removed. In one embodiment, rotation of the cannula 30 can gently move the nerve away from the access site while also protecting the nerve as tools and devices may be inserted through the cannula 30. The access cannula 30 can then provide an open lumen 31 through which surgical tools can be introduced to the site of the intervertebral disc 12. As noted above, the positioning of the access cannula 30 protects the exiting nerve (not shown) from coming into contact with any of the surgical tools.

Figure 13:
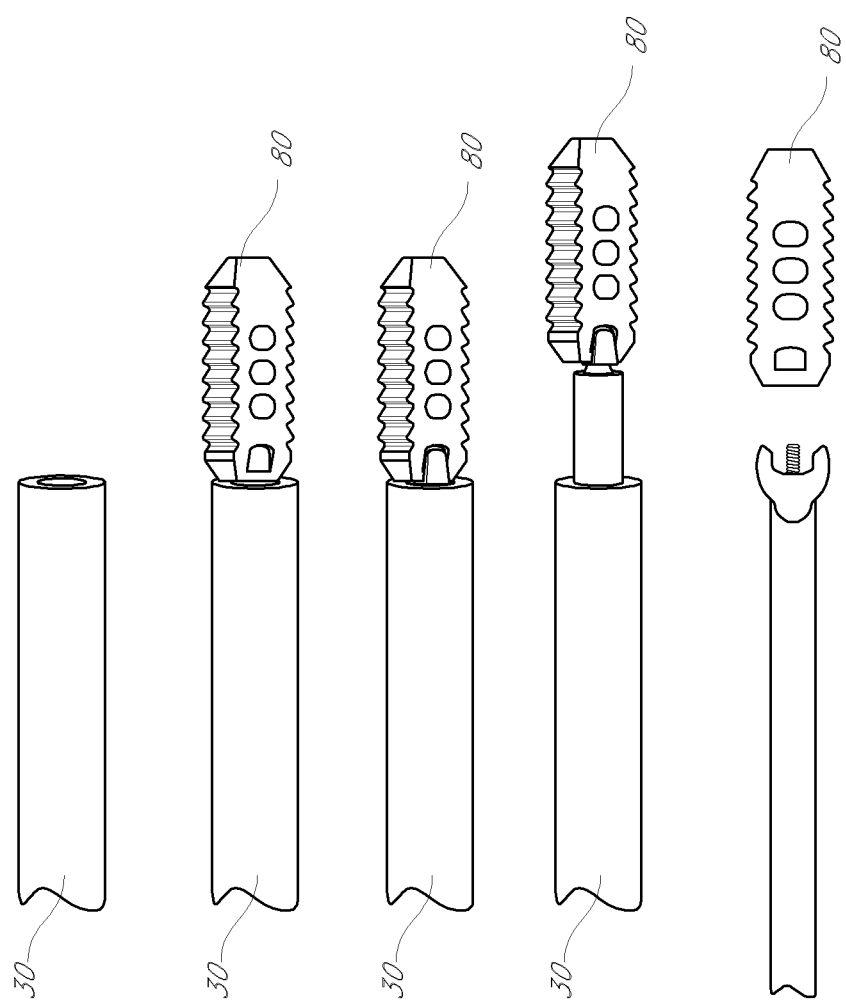
FIG. 13 is a plan view of an intervertebral implant for delivery through the access cannula.

An example of a surgical tool for use through the access cannula is depicted in FIG. 13. The intervertebral implant 80 may be introduced through the access cannula 30, and released once in position. Although a particular intervertebral implant is shown here, one of skill in the art will readily understand that any number of surgical tools may be introduced through the access cannula. For example, surgical tools to be inserted through the access cannula may include, without limitation, discectomy tools, tissue extractors, rasps, forceps, drills (e.g., trephine), rongeurs, curettes, paddle distractors, mechanical distractors, lasers, automated probes, manual probes, and plasma wands. In one embodiment of use, an opening in the disc annulus can be formed and a portion of the disc can be removed using tools advanced through the access cannula 30. The disc space can be distracted (e.g., using paddle distractors) before and/or after the implant 80 and/or different or additional interbody devices are inserted through the access cannula 30 and placed between the vertebral bodies to maintain spacing. In some embodiments the disc nucleus or portions thereof is removed while leaving the disc annulus.

FIGS. 14-20D illustrate another aspect of a dilation introducer 1100 that can be used to perform percutaneous orthopedic surgery. The dilation introducer in this embodiment is similar in some respects to that described above. As will be described in detail below, the proximal portion of the dilation introducer 1100 differs significantly from that of the dilation introducer 100 described above. The dilation introducer 1100 in the illustrated embodiments can comprise an access cannula 130, and a first, second and third dilator tubes 140, 145, 160. While the illustrated embodiment includes first, second and third dilator tubes 140, modified embodiments can include more or less dilator tubes and/or dilator tubes with modified features. It is also anticipated that in some embodiments, the access cannula 130 can be eliminated from the introducer or modified.

Figure 14A:
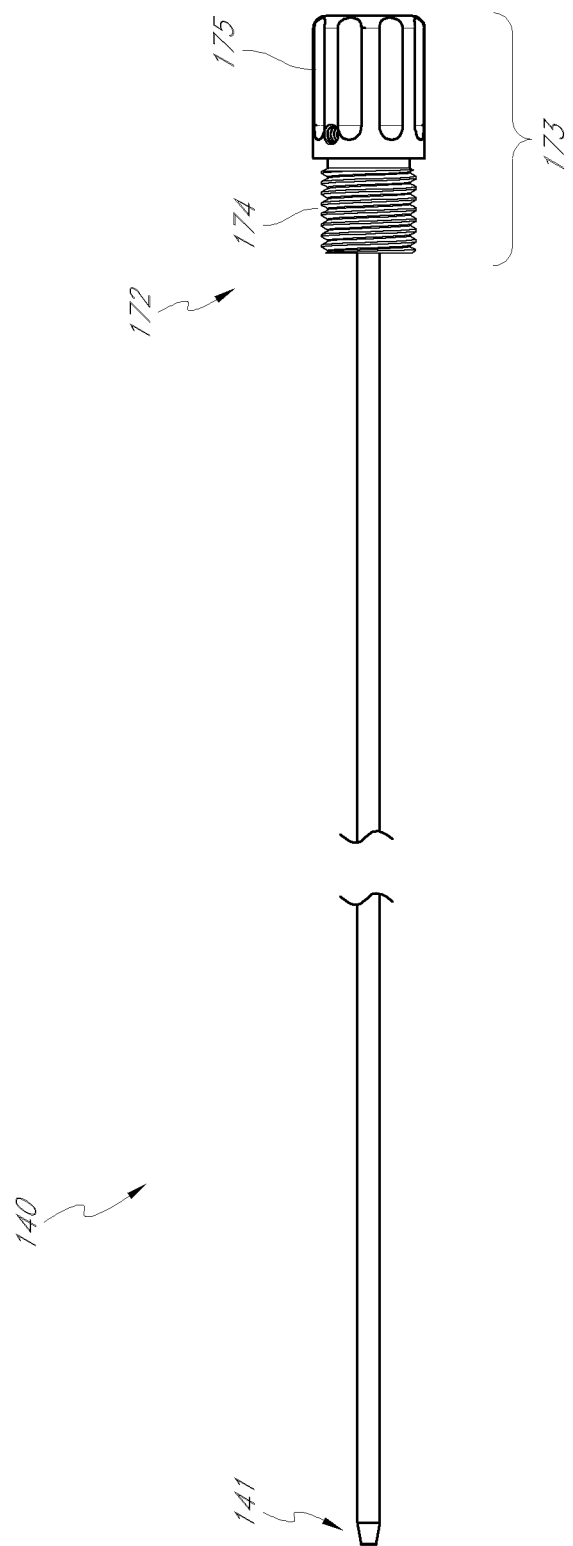
FIG. 14A is a plan view of another embodiment of a first dilator tube.
Figure 14B:
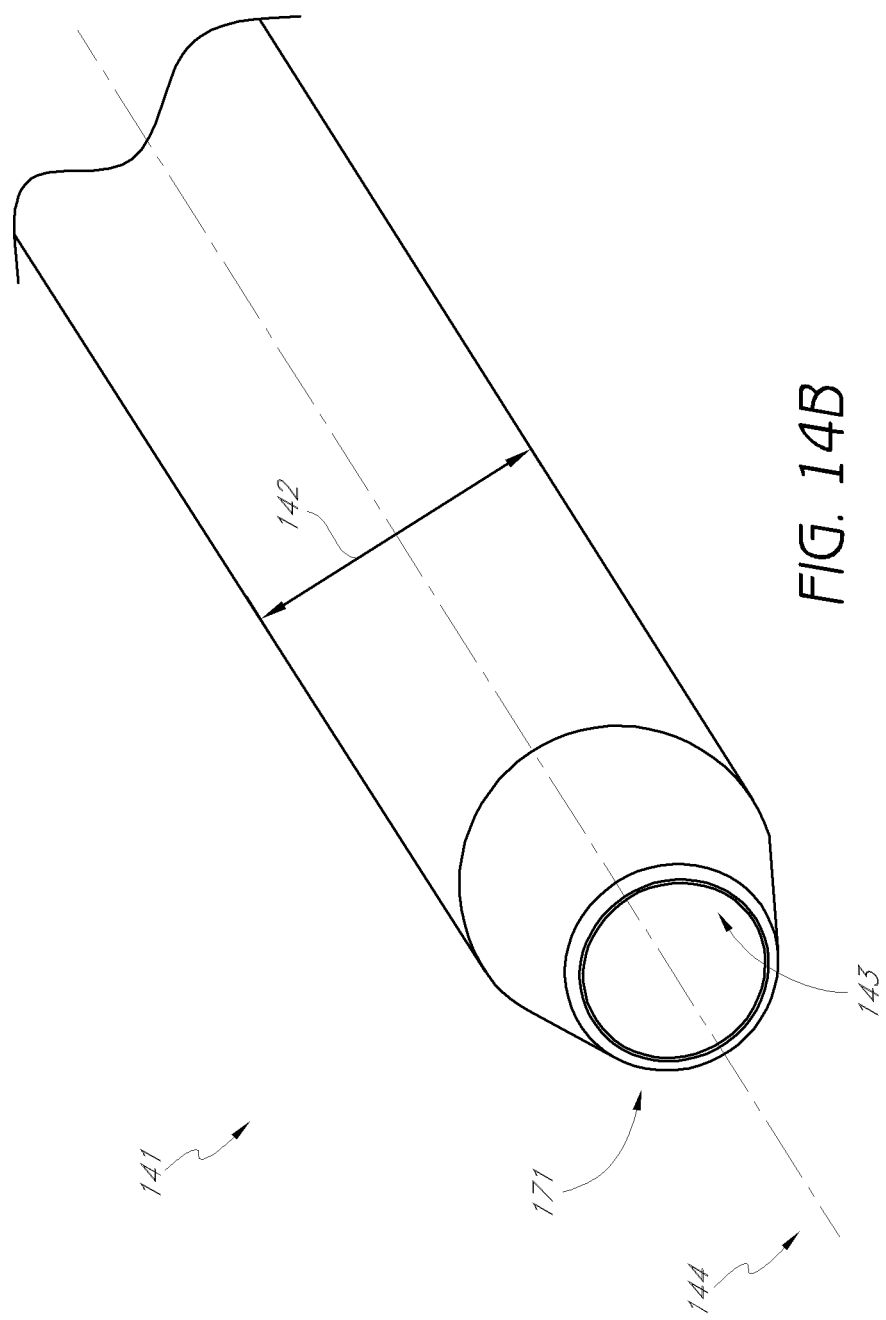
FIG. 14B is an enlarged detail view of the distal end of the first dilator tube shown in FIG. 14A.
Figure 14C:
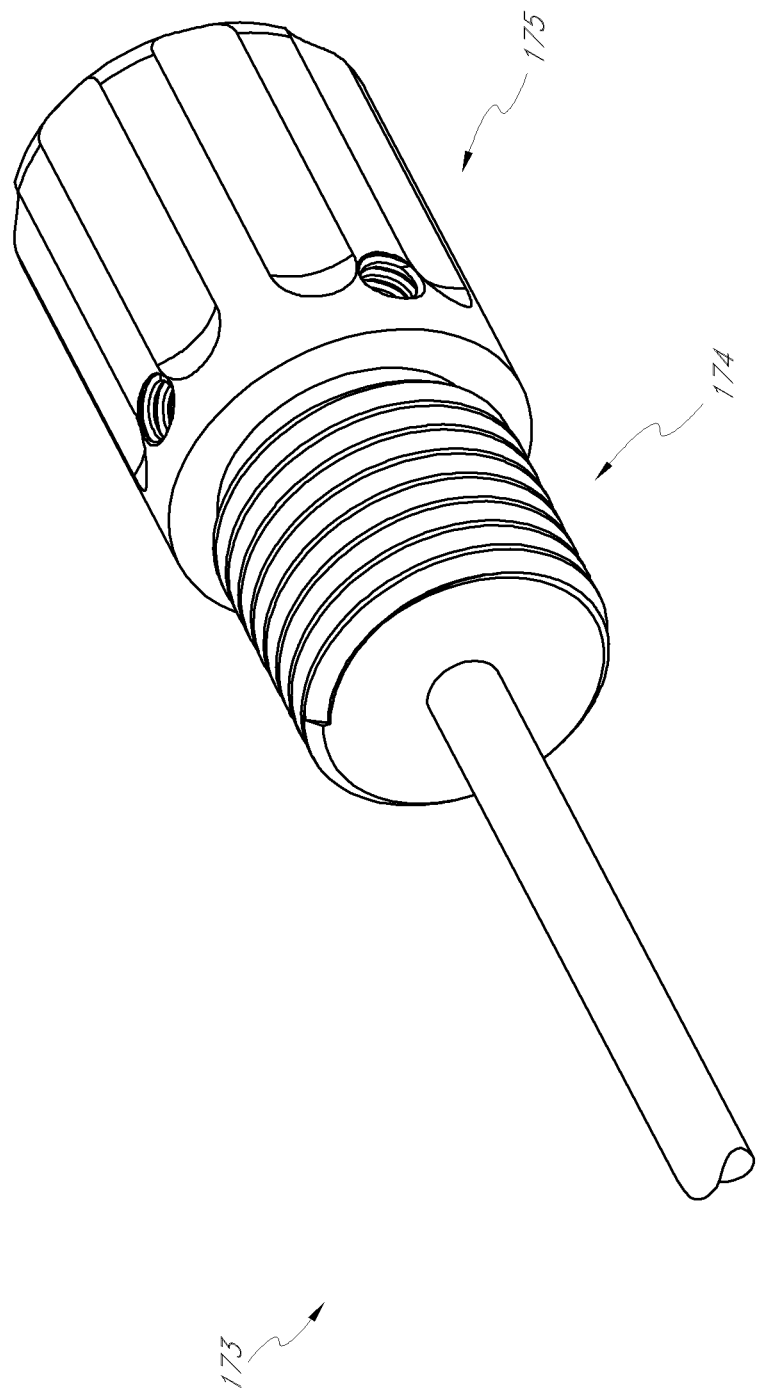
FIG. 14C is an enlarged detail view of the proximal end of the first dilator tube shown in FIG. 14A.

FIGS. 14A to 14C illustrate an embodiment of the first dilator tube 140 of the dilation introducer 1100. As shown, in the illustrated embodiment, the first dilator tube 140 may have distal portion 141, an outer radius 142, and a first longitudinal lumen 143. The outer radius 142 can be centered around first longitudinal axis 144. The distal portion 141 may include a tapered tip 171 of the dilator tube. The proximal portion 172 of the first dilator tube may include a first proximal head 173, with a threaded portion 174 distal to the gripping portion 175. In some embodiments, the longitudinal lumen 143 extends through the proximal head 173, such that a guidewire or K-wire may be introduced through the proximal head 173 and the dilator tube 140.

Figure 15A:
FIG. 15A is a plan view of another embodiment of a second dilator tube.
Figure 15B:
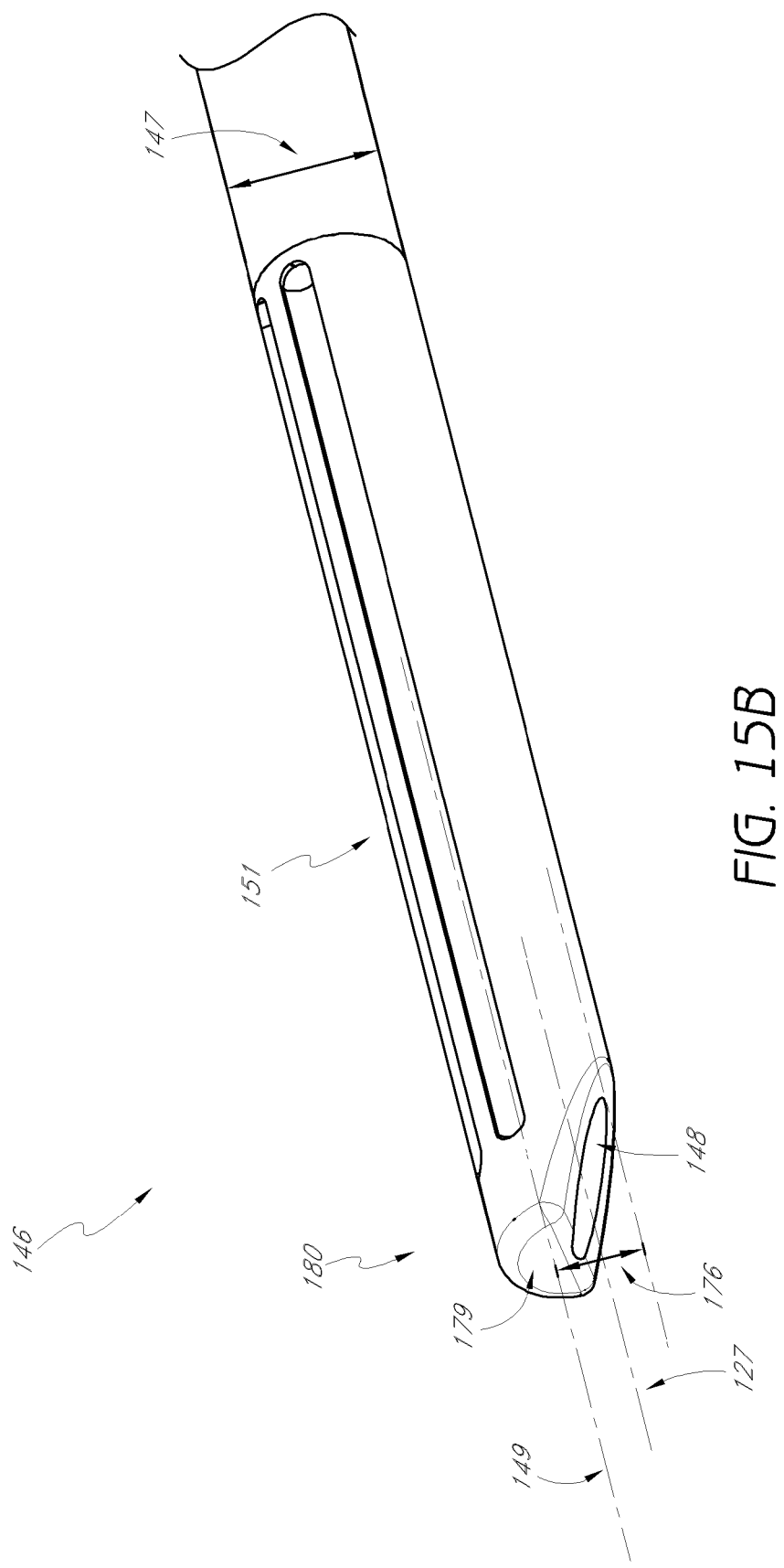
FIG. 15B is an enlarged detail view of the distal end of the second dilator tube shown in FIG. 15A.

FIGS. 15A to 15C illustrate an embodiment of the second dilator tube 145. In the embodiment shown the second dilator tube has a distal portion 146, and an outer radius 147. The outer radius may be centered around a second longitudinal axis 149. The second dilator tube includes a second longitudinal lumen 48 with an inner radius 176. The outer radius 142 of the first dilator tube may be nearly equivalent to the inner radius 176 of the second dilator tube, such that the first dilator tube 140 can be slidably received within the second longitudinal lumen 148. The proximal portion 177 of the second dilator tube includes a collar 178.

FIG. 15B shows an enlarged detail view of the distal portion of the second dilator tube 145. The distal portion 146 of the second dilator tube may include a flattened edge 179. This flattened edge 179 advantageously prevents the second dilator tube 145 from penetrating the intervertebral disc 112. The tip 180 of distal portion 146 can have a generally semi-annular cross-section, configured such that when the first dilator tube 140 is received within the second dilator tube 145, the outer radial surface of the first dilator tube 140 is partially exposed at the distal tip 180 of the second dilator tube 145. The opening of the generally semi-annular cross-section of the second dilator tube can be oriented opposite the second longitudinal axis 149 with respect to the longitudinal axis 127 of the second longitudinal lumen.

When the first dilator tube 140 is received within the second dilator tube 145, the longitudinal axis 127 of the second longitudinal lumen is essentially aligned with the first longitudinal axis 144. Additionally, the second dilator tube 145 can include cutting flutes or ridges 151 on one side, located opposite the opening of the generally semi-annular cross-section of the second dilator tube 145. In other embodiments, the cutting flutes 151 may be replaced with a coarse surface (e.g., knurling, sharp edges, abrasive members, etc.) which, when rotated or slid (e.g., back and forth) against bone, will create a recess therein. As noted above, other mechanisms for removing bone can be used, and the cutting flutes are shown here by way of example only. As can be seen in FIG. 15B, the inner lumen 148 of the second dilator tube 145 can be off-center. In this configuration, the cutting flutes 151 are further from the axis of rotation than the side opposite the cutting flutes. This is particularly advantageous for performing foraminoplasty while protecting the exiting nerve, as will be discussed in more detail below.

FIG. 15C shows an enlarged detail view of the proximal portion 177 of the second dilator tube 145. The collar 178 includes an aperture 181, which may be used in conjunction with the third dilator tube, as described in detail below. In alternative embodiments, the aperture 181 may be instead replaced with a circumferentially oriented groove.

FIGS. 16A to 16D illustrate and embodiment of the third dilator tube 160, which can be configured to be slidably introduced over the second dilator tube 145. The third dilator tube 160 can include a distal portion 161, a third outer radius 162 centered around a third longitudinal axis 163, and a third longitudinal lumen 164 having a third inner radius 165 centered around longitudinal axis 169 that runs parallel to and laterally offset from the third longitudinal axis 163. The third lumen 164 can be configured to removably receive the second dilator tube 145 for slidable movement within the third lumen 164. In such a configuration, the second longitudinal axis 149 essentially aligns with the longitudinal axis 169 of the inner lumen 164 of the third dilator tube 160. The proximal portion 182 includes a handle assembly 183.

Figure 16A:
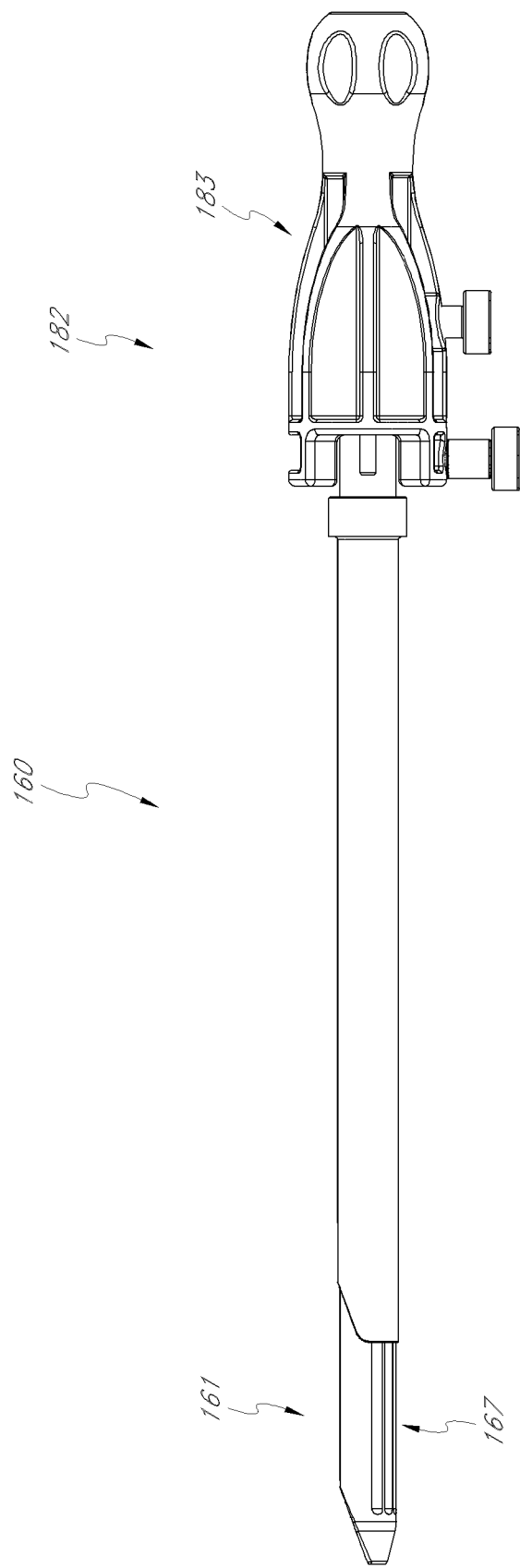
FIG. 16A is a plan view of another embodiment of a third dilator tube.

FIG. 16B shows an enlarged detail view of the distal portion of the third dilator tube of FIG. 16A. The distal portion 161 of the third dilator tube may include a flattened edge 185. This flattened edge 185 advantageously prevents the third dilator tube 160 from penetrating the intervertebral disc 112. The tip 184 of the distal portion 161 has a generally semi-annular cross-section, and cutting flutes 167 for reaming bone located opposite the opening of the semi-annular cross-section. As with the second dilator tube, in other embodiments the cutting flutes may be replaced or used in combination with a coarse or other cutting or abrading surface which, when rotated or slid against bone, will create a recess therein. As can be seen in FIG. 16B, the longitudinal lumen 164 of the third dilator tube 160 may be off-center. In this configuration, the cutting flutes 167 are further from the axis of rotation than the side opposite the cutting flutes. This is particularly beneficial for performing foraminoplasty while protecting the exiting nerve, as will be discussed in more detail below.

Figure 16C:
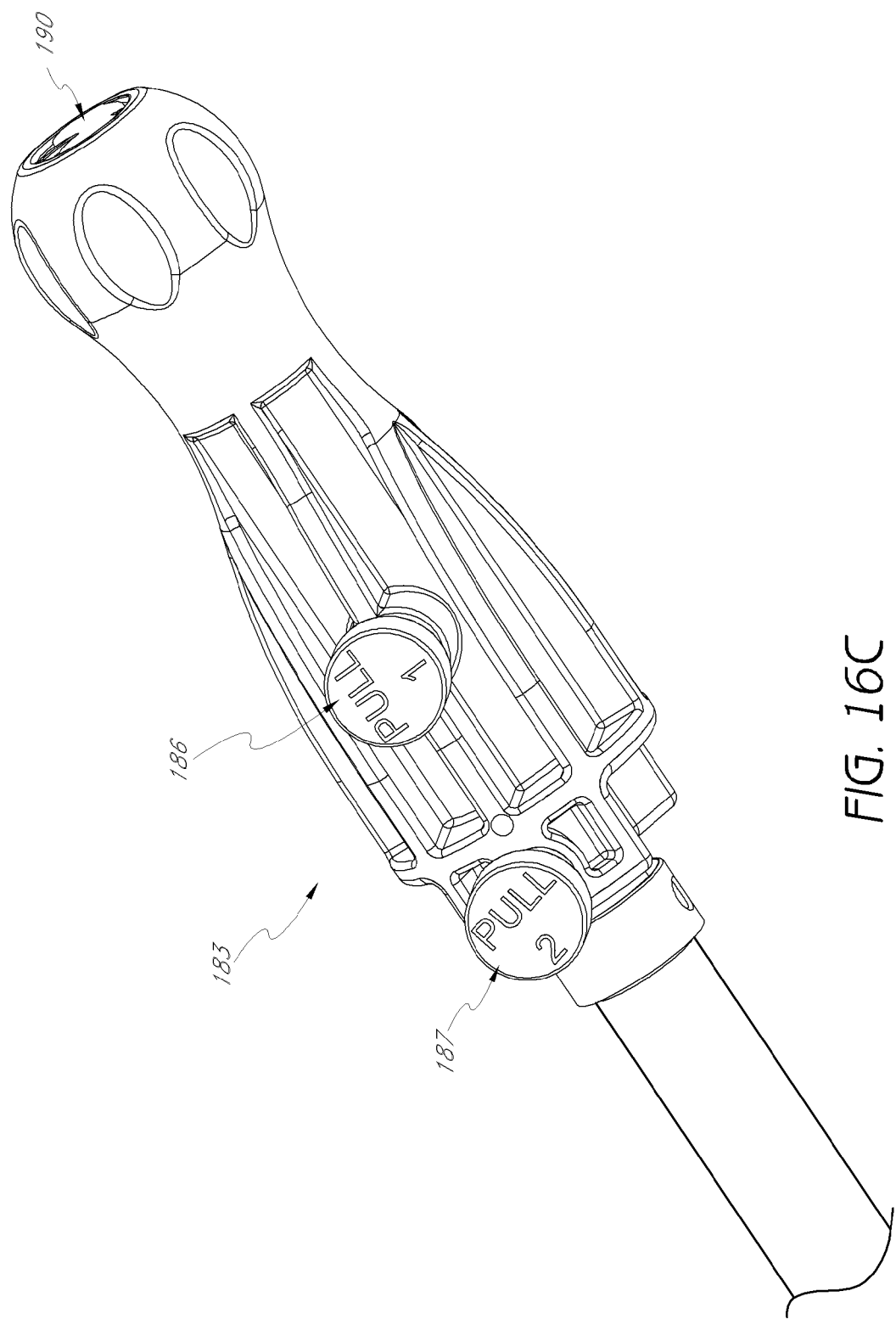
FIGS. 16C and 16D are enlarged detail views of the proximal end of the third dilator tube shown in FIG. 16A.
Figure 16D:
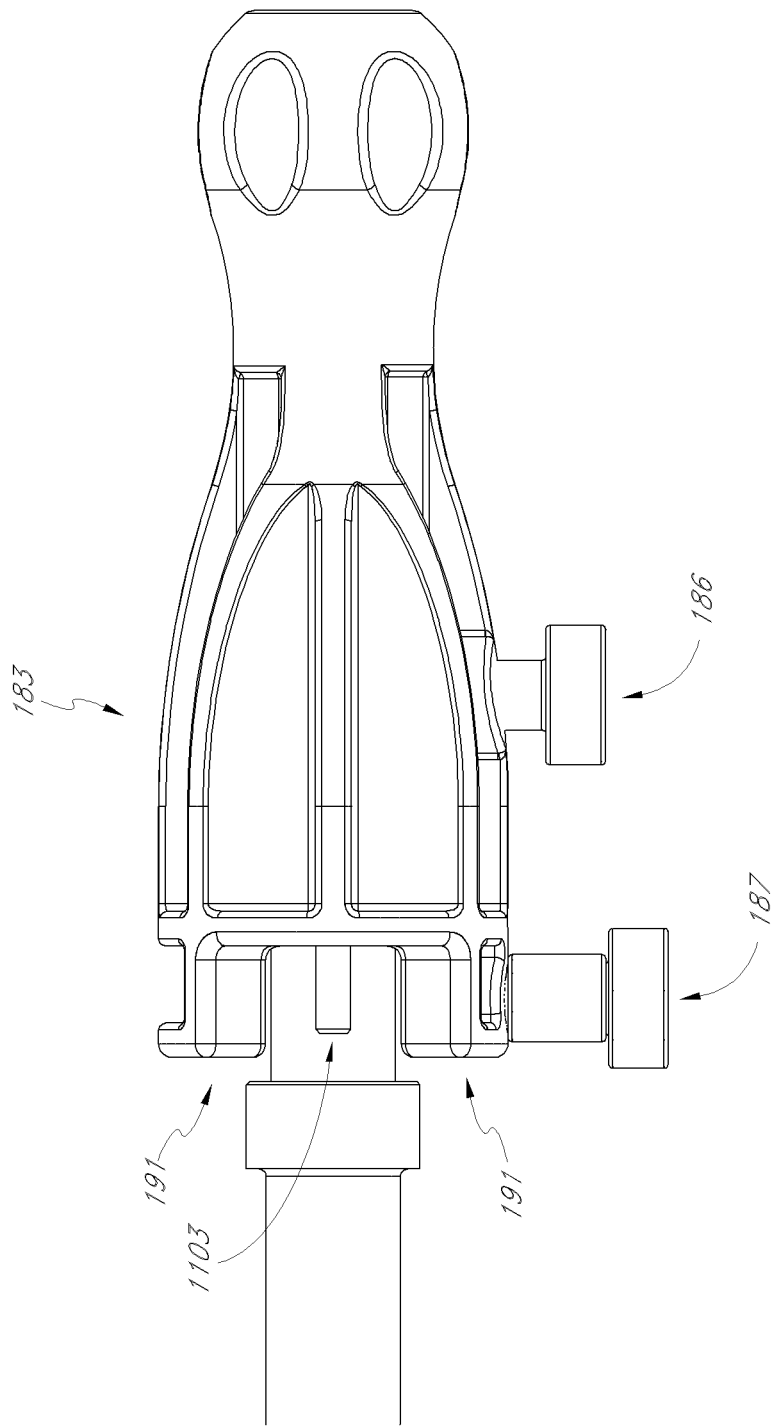

FIGS. 16C and 16D show enlarged detail views of the proximal portion 182 of the third dilator tube 160. The proximal portion 182 includes a handle assembly 183. A first latching button 186 may be configured for constraining the movement of the third dilator tube relative to the second dilator tube, as described in more detail below. In various embodiments, the latching button 186 may constrain slidable movement, rotational movement, or both. A second latching button 187 may be located distal the first latching button 186, and may be configured to constrain the movement of the access cannula relative to the third dilator tube, as described in more detail below. The distal end of the handle assembly 183 includes an overhanging lip 191 into which the proximal grip 136 of the access cannula can be removably received. When the proximal grip 136 of the access cannula is received within the overhanging lip 191, the locking pin 1103 slides within the locking pinhole 1104 on the proximal grip 136 of the access cannula, thereby restricting rotational movement of the access cannula relative to the third dilator tube. In various embodiments, the locking pinhole may be omitted, permitting rotation of the access cannula 130 relative to the third dilator tube 60.

Figure 17A:
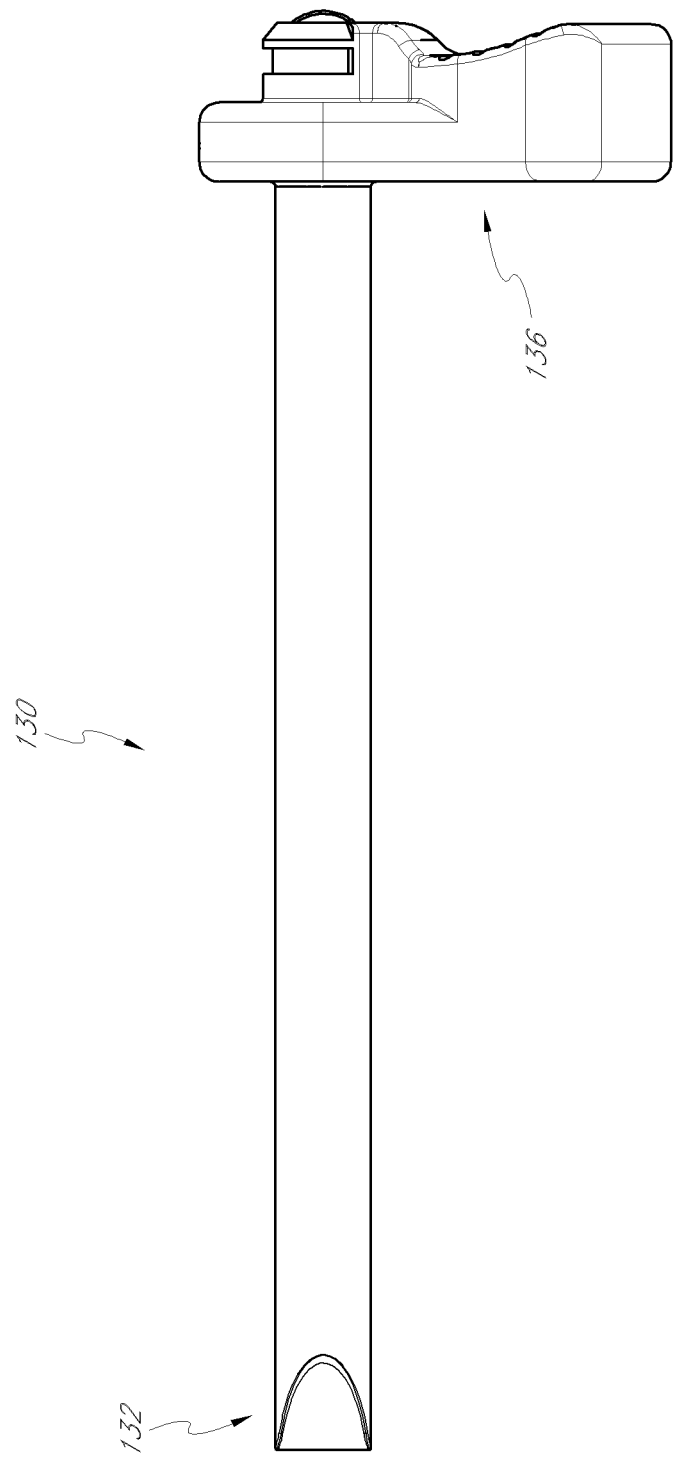
FIG. 17A is a plan view of another embodiment of an access cannula.
Figure 17C:
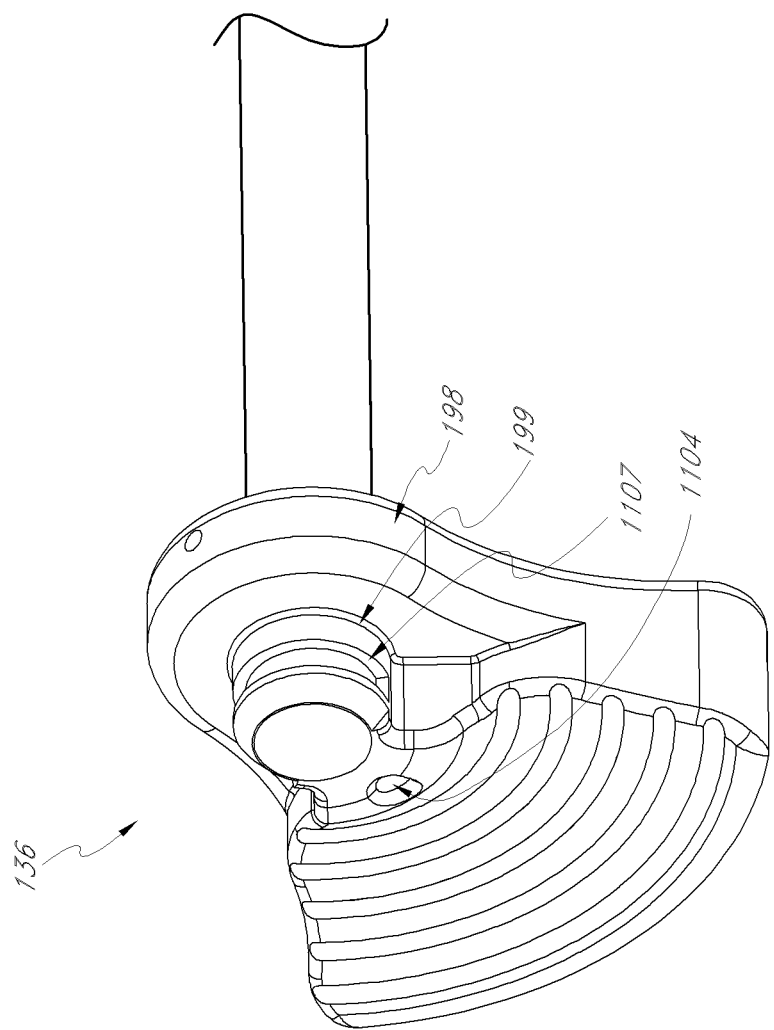
FIG. 17C is an enlarged detail view of the proximal end of the access cannula shown in FIG. 17A.

FIGS. 17A to 17C illustrate an embodiment of the access cannula 130, which can be configured to be introduced over the third dilator tube 145. The access cannula 130 has a distal portion 132, a fourth longitudinal axis 134, and a fourth longitudinal lumen 131 having a fourth inner radius 135. The access cannula 130 may be configured to removably receive the third dilator tube (not shown) for slidable movement within the third lumen. A handle 136 allows for rotation of the access cannula 130.

FIG. 17B shows an enlarged detail view of the distal portion of the access cannula of FIG. 17A. The distal portion 132 can have a generally semi-annular cross-section. In the embodiment shown, the fourth longitudinal lumen may be centered with respect to the outer radius of the access cannula, in contrast to the second and third dilator tubes. In other embodiments, however, the access cannula may also have a longitudinal lumen that is off-center with respect to the outer radius. In yet another embodiment, the access cannula need not be limited to a cylindrical outer surface. The outer surface could, for instance, have an elliptical, polygonal, or other cross-sectional shape.

FIG. 17C shows an enlarged detail view of the proximal portion 193 of the access cannula of FIG. 17A. The proximal grip 136 may provide additional leverage while advancing the access cannula over the third dilator tube. The proximal grip 136 includes a larger diameter portion 198 and a smaller diameter portion 199. The smaller diameter portion 199 includes a circumferential channel 1107 for use in interlocking with the third dilator tube, as discussed in detail below. A locking pinhole 1104 can receive the locking pin 1103 on the third dilator tube, thereby restraining rotational movement of the access cannula 160 relative to the third dilator tube 145.

Figure 18A:
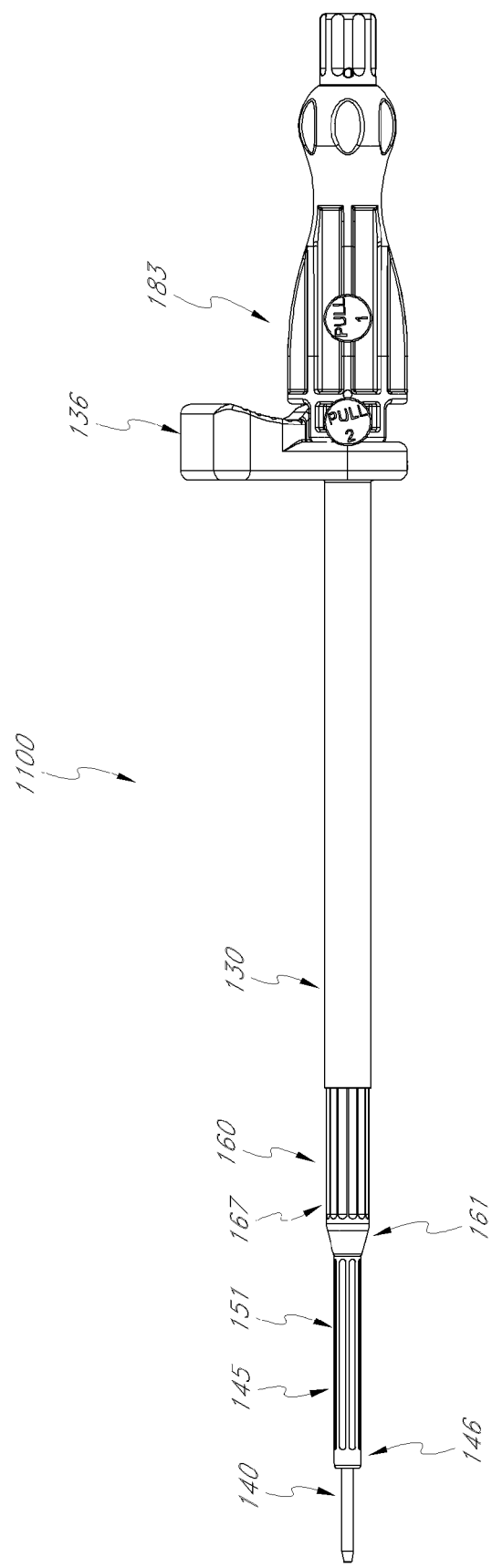
FIG. 18A is a plan view of another embodiment of a dilation introducer comprising the first dilator tube of FIG. 14A, the second dilator tube of FIG. 15A, the third dilator tube of FIG. 16A, and the access cannula of FIG. 17A.
Figure 18B:
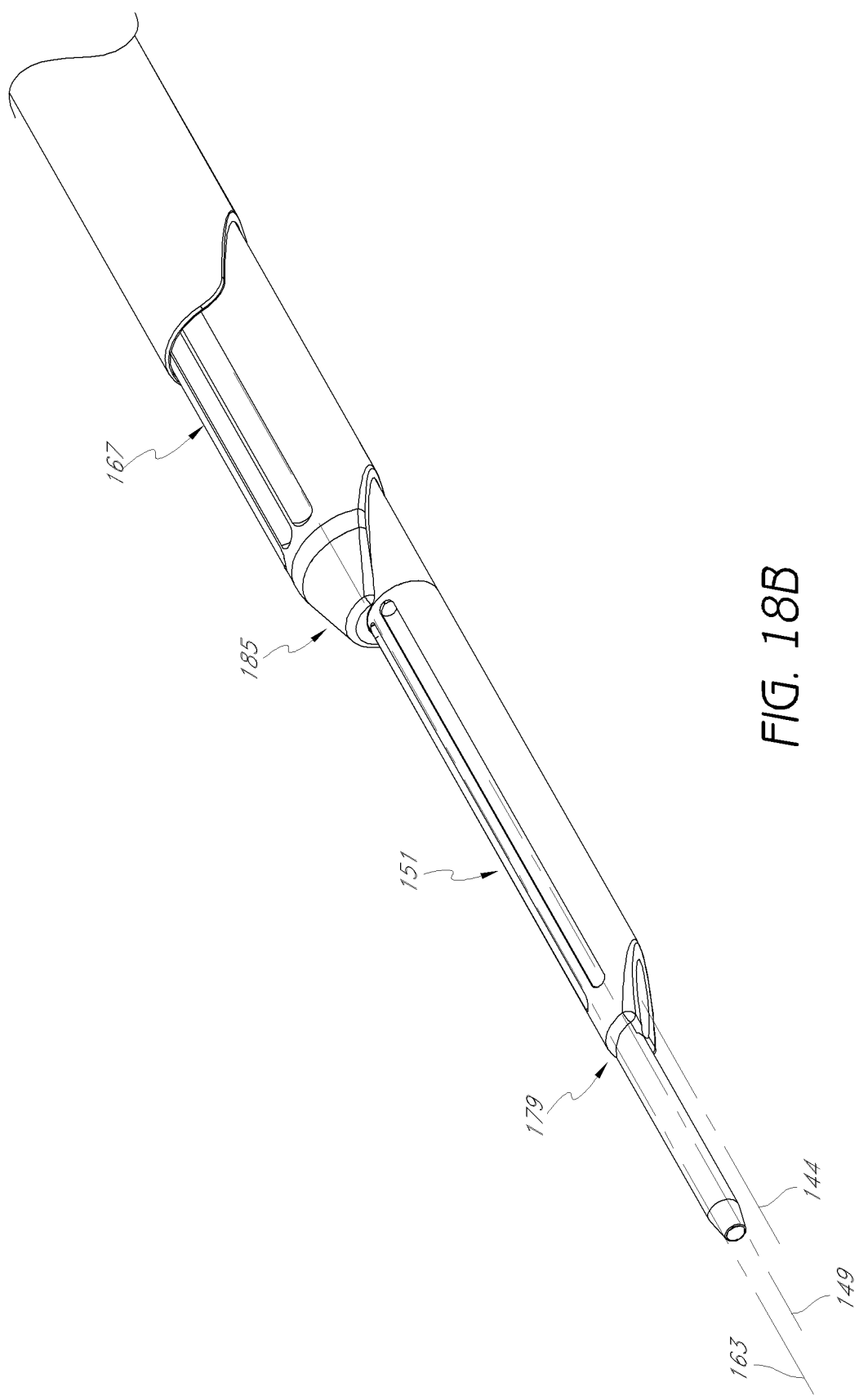
FIG. 18B is an enlarged detail view of the distal end of the dilation introducer shown in FIG. 18A.
Figure 18C:
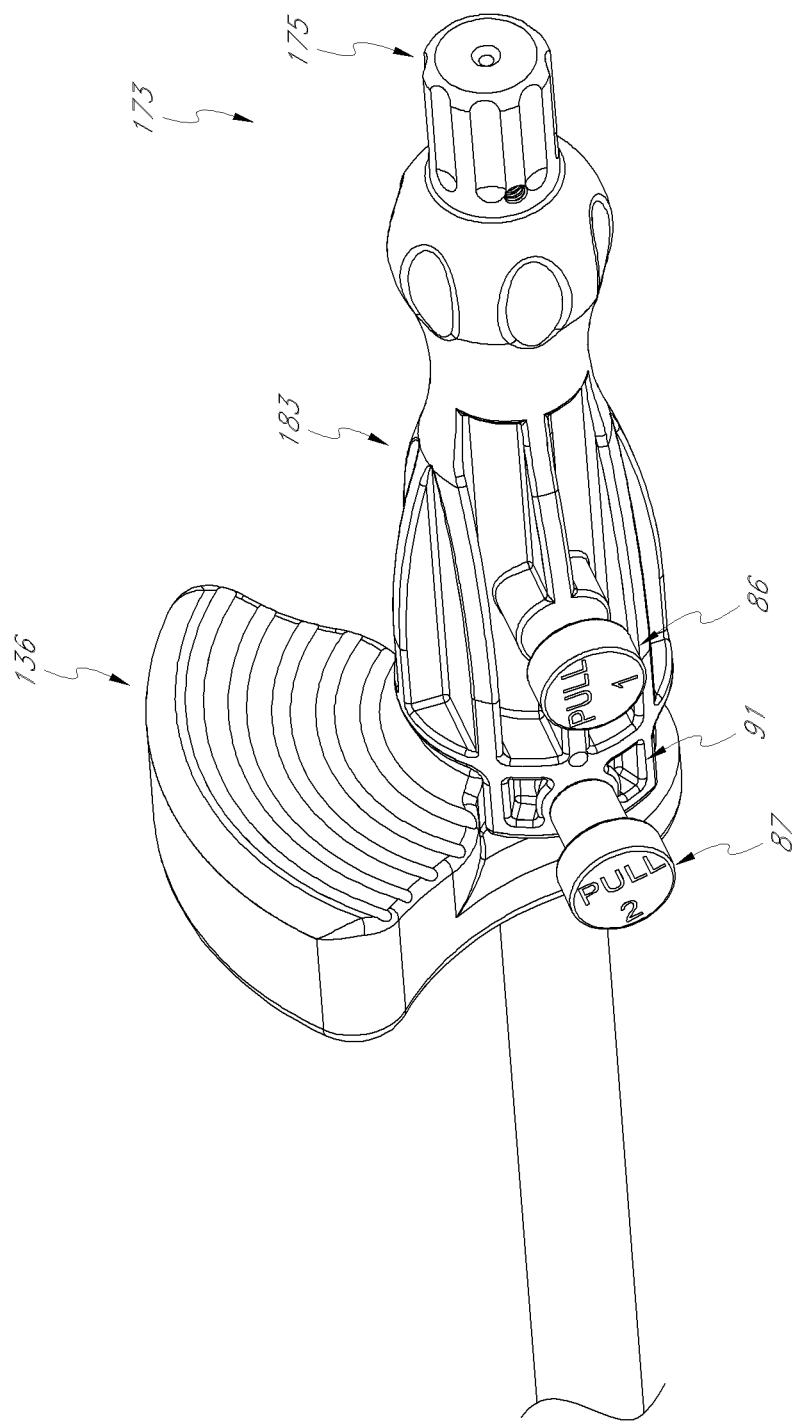
FIG. 18C is an enlarged detail view of the proximal end of the dilation introducer shown in FIG. 18A.

FIGS. 18A to 18C illustrate one embodiment of the dilation introducer 1100 in an assembled configuration. As shown, the access cannula 130 can be positioned over the third dilator tube 160, which can be positioned over the second dilator tube 145, which in turn can be positioned over the first dilator tube 140. The handle assembly 183 of the third dilator tube may be in a locked configuration with the proximal grip 136 of the access cannula can be locked together to constrain slidable movement, but allow for the access cannula 130 to rotate with respect to the third dilator tube 160. Additionally, the second dilator tube 145 may be locked together with the third dilator tube to constrain slidable movement, while still allowing the second dilator tube 145 to rotate with respect to the third dilator tube. Alternatively, the second dilator tube may be in a locked configuration preventing both slidable and rotational movement with respect to the third dilator tube 145. The third dilator tube 60 can be advanced distally until the distal portion 161 of the third dilator tube aligns with the distal portion 46 of the second dilator tube. Further, the access cannula 130 may also be advanced so that the distal portion 32 aligns with the distal portions 146, 161 of the second and third dilator tubes. The second and third dilator tubes 145, 160 each have cutting flutes 151, 167 on their respective distal portions 146, 161. As can be seen, the first, second, and third longitudinal axes 144, 149, 163 are each laterally offset from one another.

In certain embodiments, the first, second and third dilator tubes 140, 145, 160 along with the access cannula 130 can be provided with additional stops that engage the proximal grip 136 of the access cannula and the handle assembly 183 of the third dilator tube described above. For example, in one embodiment, notches or detents can be provided that engage the proximal grip 136 or handle assembly 183 when one tube is advanced distally and reaches a specific location (e.g., end point). In this manner, forward movement of a tube or cannula can be limited once the tube or cannula is advanced to a desired location FIG. 18B shows an enlarged detail view of the distal portion of the dilation introducer of FIG. 18A. The distal portions 146, 161, 132 of each of the second and third dilator tubes 145, 160, and of the access cannula 130 may have generally semi-annular cross-sections. The distal portions 146, 161 of the second and third dilator tubes 145, 160 in the illustrated embodiment can have flattened edges 179, 185 to prevent penetration into the intervertebral disc as each dilator tube is advanced.

FIG. 18C shows an enlarged detail view of the proximal portion of the dilation introducer of FIG. 18A. The proximal grip 136 of the access cannula 130 is shown in a locked configuration with the handle assembly 183 of the third dilator tube 160. The smaller diameter portion (not shown) may be received within the overhanging lip 191 on the distal end of the handle assembly 183. Latching buttons 186, 187 constrain movement of the third dilator tube relative to the second dilator tube, and of the access cannula relative to the third dilator tube, respectively. The gripping portion 175 of proximal head 173 of the first dilator tube 140 is visible at the proximal end of the dilation introducer. As shown, the first dilator tube may be fastened to the handle assembly 183 by means of the threaded portion 174 (not shown) on the proximal head 173 and the threaded receiving portion 190 (not shown) of the handle assembly 183. As shown, this fastening constrains both rotational and slidable movement of the first dilator tube relative to the third dilator tube. In various embodiments, the first dilator tube may be affixed to the handle assembly 183 by other means that allow for free rotational movement, free slidable movement, or both.

Figure 19A:
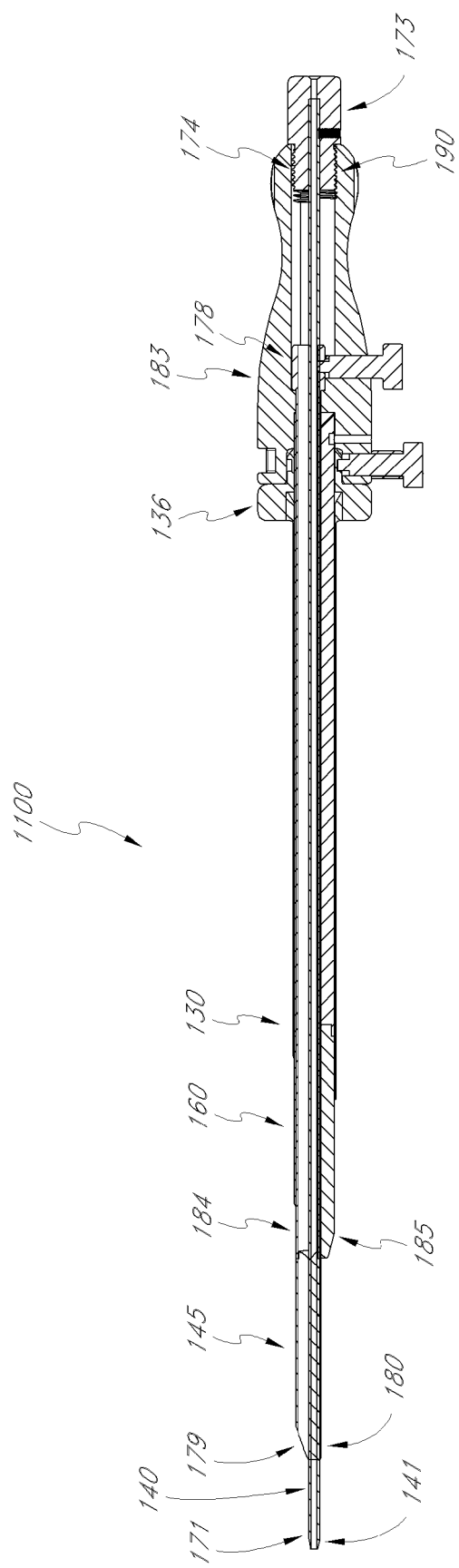
FIG. 19A is a longitudinal cross-sectional view of the dilation introducer of FIG. 18A.
Figure 20A:
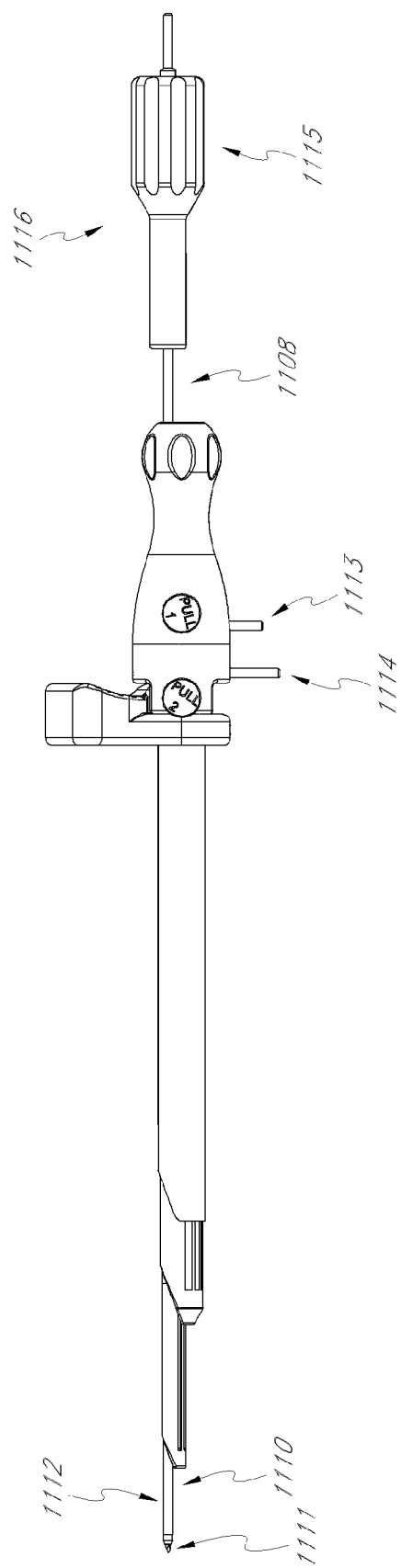
FIG. 20A is a plan view of a dilation introducer equipped with neuro-monitoring leads and a neuro-monitoring needle.
Figure 20B:
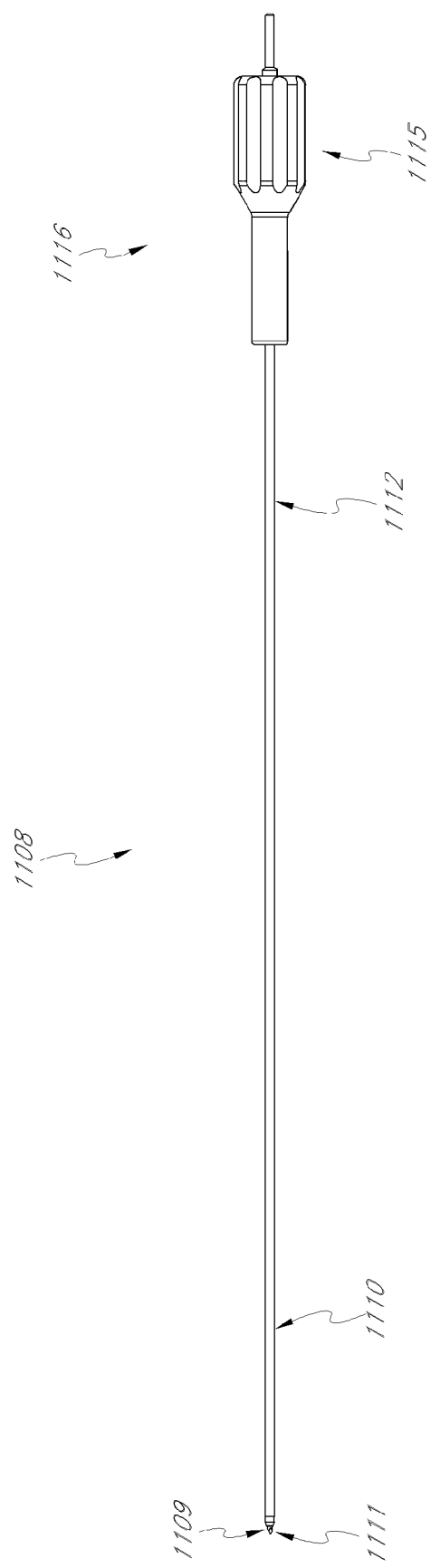
FIG. 20B is a plan view of the neuro-monitoring needle shown in FIG. 20A.
Figure 20D:
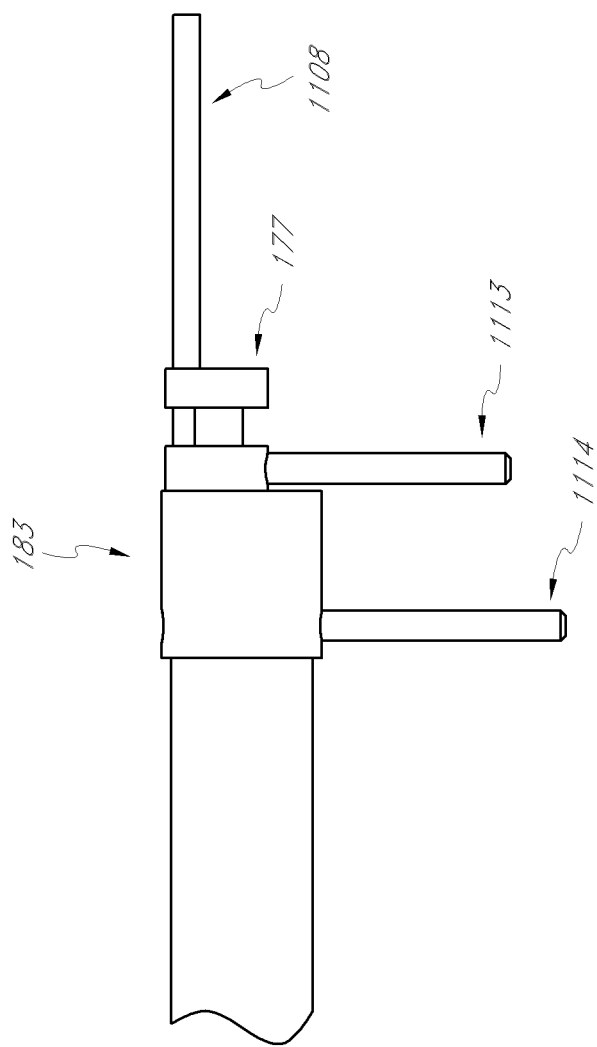
FIG. 20D is an enlarged detail view of the neuro-monitoring leads shown in FIG. 20A.

Referring to FIGS. 19A and 19B, a dilation introducer 1100 is shown in a locked assembled configuration. The dilation introducer 1100 includes a first dilator tube 140, a second dilator tube 145, a third dilator tube 160, and an access cannula 130. The first dilator tube has a distal portion 141 with a tapered tip 171, and a proximal portion 172 having a proximal head 173. In various embodiments, the first dilator tube 140 may be cannulated, for example to allow passage of a guide wire down the longitudinal axis 143 of the first dilator tube 140, or the first dilator tube may be without a lumen and uncannulated. The second dilator tube 145 has a distal tip 180 with a flattened edge 179, a proximal portion 177 with a collar 178, and a longitudinal lumen 148. The first dilator tube 140 may be removably received within the second dilator tube 145.

The third dilator tube 160 has a distal tip 184 with a flattened edge 185, a proximal portion 182 with a handle assembly 183, and a longitudinal lumen 164. The second dilator tube 145 may be removably received in the longitudinal lumen 164 of the third dilator tube 160 for slidable movement within the third dilator tube 160. The threaded portion 174 of the proximal head 173 of the first dilator tube engages with the interior threaded receiving portion 190 of the handle assembly 183 of the third dilator tube 160. With the proximal head of the first dilator tube affixed to the handle assembly 183, the first and third dilator tubes 140, 160 may be locked together for length and rotation. The second and third dilator tubes may be connected together in a locked configuration with a first latching button 186 disposed on the handle assembly 183 of the third dilator tube 160 and extending through a first aperture 1105 in the handle assembly 183 of the third dilator tube 160, so that the first latching button 186 may be moveable between a radially inward locking position (arrow 1101) and a radially outward unlocking position (arrow 1102).

The distal end 196 of the first latching button may be removably received in aperture 181 of the second dilator tube 145 so as to engage and lock the second and third dilators together in the locking position. Alternatively, the latching button may be received in a circumferentially oriented groove of the second dilator tube, which may or may not extend completely around the second dilator tube. The first latching button 186 may be pulled radially outwardly to release the second dilator tube 145, to allow the third dilator tube 160 to slide with respect to the second dilator tube 145.

The access cannula 130 has a distal portion 161, a proximal portion 193, a proximal grip 136, and longitudinal lumen 164. The third dilator tube 145 may be removably received within the access cannula 130 for slidable movement within the longitudinal lumen 131 of the access cannula 130. The third dilator tube 145 and the access cannula 130 also have a locked configuration in which the access cannula 130 may be not permitted to slidably telescope over the third dilator tube 145.

The proximal portion 193 of the access cannula 130 includes a proximal grip 136 with a larger diameter portion 198 and a smaller diameter portion 199. The smaller diameter portion 199 may be sized to fit under an overhanging lip 191 of the third dilator tube, when the longitudinal axes of the third dilator tube and access cannula may be aligned. There may be a circumferentially oriented channel 1107 in the exterior of the smaller diameter portion 919 for receiving a distal end 197 of a second latching button 187. The circumferentially oriented channel 1107 does not need to extend completely around the exterior of the smaller diameter portion 199.

The third dilator tube 145 and the access cannula 130 may be connected together in a locked configuration with the second latching button 187 disposed on the overhanging lip 191 of the handle assembly 183 of the third dilator tube 145. The second latching button extends through an aperture 1106 in the overhanging lip 191 of the handle assembly 183 and may be movable between a radially inward locking position (arrow 194) and a radially outward unlocking position (arrow 195). The distal end 197 of the second latching button 187 may be removably received in the channel 107 located in the smaller diameter portion 199 of the access cannula 130, in the locking position, to lock the third dilator tube 45 and the access cannula 130 in the locked assembled configuration. The second latching button 187 may be pulled radially outward to release the access cannula 130 to slide to the unlocked configuration. Furthermore, the second and third dilator tubes 140, 145 may be removed together as a unit from the access cannula 130. In other words, the first dilator tube 140 and second dilator tube 145 can be kept locked together and can be removed from the access cannula 130 by unlocking the second latching button 187 alone. An advantage of this embodiment is that the latching buttons 186, 187 may be both removable from the surgical field with the release of the third dilator tube from the access cannula 130.

The access cannula being free of protuberances, such as the latching buttons, is less likely to catch surgical sponges and sutures, for example, on the dilation introducer.

Dilation Introducer with Neuro-Monitoring

FIGS. 20A to 20D show another aspect of a dilation introducer, in which the first dilator tube may be replaced with a neuro-monitoring needle 1108. The neuro-monitoring needle 1108 includes a wire 1109 which may be enclosed by a needle cannula 1110, with the wire 1109 exposed at the distal tip 1111. The needle cannula 1110 may be surrounded by dielectric coating 1112 along its length for insulation. For example, the wire 1109 can comprise stainless steel and the dielectric coating 1112 can comprise parylene. As noted above, a knob 1115 may be located on the proximal portion 1116 of the neuro-monitoring needle 1108. A first neuro-monitoring lead 1113 may be attached to the proximal portion 177 of the second dilator tube 145. A second neuro-monitoring lead 1114 may be attached to the proximal portion 183 of the third dilator tube 160.

The neuro-monitoring needle 1108 can be made from several components. The wire 1108 portion can be stainless steel coated with dielectric coating 1112 of parylene. The distal tip 1111 of the wire 1109 can be exposed so that it can transmit current. The needle cannula 1110 which covers the wire 1109 can also comprise stainless steel coated with parylene. In some embodiments, this needle cannula could also be described as an exchange tube where once the wire is removed a K-wire could be placed down it and into the disc space. The wire 1109 can be attached to a handle at the proximal end ultimately protrude from the handle, serving as the electrode to attach a neuromonitoring system. In some embodiments, the proximal diameter can be parylene coated, while the rest of the wire 1109 can be uncoated to transmit the current.

The wire 1109 may comprise a conductive material, such as silver, copper, gold, aluminum, platinum, stainless steel, etc. A constant current may be applied to the wire 1109. The needle cannula 1110 may be insulated by dielectric coating 1112. Although the coating shown here is dielectric, any sufficiently insulative coating may be used. Alternatively, an insulative sleeve may encase the wire. This arrangement protects the conductive wire 1109 at all points except the most distal tip 1111. As the exposed tip of the wire 1109 is advanced through the tissue, it continues to be supplied with current. When the tip 1111 approaches a nerve, the nerve may be stimulated. The degree of stimulation to the nerve is related to the distance between the distal tip 1111 and the nerve. Stimulation of the nerve may be measured by, e.g., visually observing the patient's leg for movement, or by measuring muscle activity through electromyography (EMG) or various other known techniques.

Utilizing this configuration may provide the operator with added guidance as to the positioning of the first dilator tube to the surgical access point and through Kambin's triangle. With each movement, the operator may be alerted when the tip of the first dilator tube approaches or comes into contact with a nerve. The operator may use this technique alone or in conjunction with other positioning assistance techniques such as fluoroscopy and tactile feedback. The amount of current applied to the wire 1109 may be varied depending on the preferred sensitivity. Naturally, the greater the current supplied, the greater nerve stimulation will result at a given distance from the nerve. In various embodiments the current applied to the conductive wire 1109 may not be constant, but rather periodic or irregular. Alternatively, pulses of current may be provided only on demand from the operator.

Although not shown here, a similar configuration may be applied to the second and third dilator tubes, and to the access cannula. Each may include a conductive wire embedded within the tube, or it may be separately attached. In either configuration, a distal tip of conductive wire may be exposed and the wire may be provided with current. As the dilator tube or access cannula is advanced through the tissue and towards the access site, nerve stimulation may be monitored as described above. The current supplied to each of the first, second, and third dilator tubes and to the access cannula may be controlled independently, so that when nerve stimulation is observed, the operator may supply current separately to each wire to determine which wire or wires are nearest to the nerve. Alternatively, current may be supplied only to one wire at any given point in the procedure. For example, the current may be supplied to the wire associated with the dilator tube or access cannula that is being moved at that point in the operation.

In some embodiments, the second and third dilator tubes can comprise aluminum that has been anodized and then coated with parylene. Certain areas of the second and third dilator tubes can be masked from the anodization and parylene coating so that they can transmit the current. For example, the distal tips of the second and third dilator tubes can be exposed so as to conduct current therethrough. The exposed portions can be passivated to resist rusting, pitting, or corrosion. The exposed portions can be made by using a stainless steel pin pressed into the second and third dilator tubes. The pin can aid in locating the second and third dilator tubes on x-ray or fluoroscopy, and additionally can facilitate the transmission of current through the second and third dilator tubes to the area of contact. Electrode attachments for the second and third dilator tubes can be coated with parylene on the proximal larger diameter to prevent current from flowing into the user. The rest of the electrode can be uncoated, but passivated to resist rusting, pitting, or corrosion. The electrodes can attach such that the current is transmitted to the internal area of the second and third dilator tubes so that it can be transmitted distally through the exposed areas on the tips of the tubes. These tubes are attached to Radel handles, which being a polymer are also insulators. The third dilator tube can be made from stainless steel, coated with nylon or other polymer, such as Teflon, followed by a parylene coating. In embodiments in which the dilator tube comprises stainless steel, no additional x-ray marker is required.

Although the method as described above utilizes an embodiment of the dilation introducer as shown in FIGS. 3-7B, it will be understood that the procedure may be adapted for use with various other embodiments of the dilation introducer. For instance, the dilation introducer with alternative handle assembly, as shown in FIGS. 14A-19C, may be used with appropriate modifications to the method described above. For instance, as the proximal head 173 of the first dilator tube 140 may be screwed into the handle assembly 183 of the third dilator tube 160, the first dilator tube 140 must be unscrewed and removed prior to advancing the third dilator tube over the second dilator tube. Additionally, the latching buttons 186, 187 of the handle assembly 183 may be used to control the locking and unlocking of the dilator tubes relative to one another.

Alternatively, the dilation introducer equipped with neuro-monitoring, as shown in FIGS. 20A-D, may be substituted. The method performed may be then similar to that described above, except that in addition the method involves monitoring nerve stimulation to assist with placement and guidance of the dilator tubes and access cannula. As described above, the current supplied to the conductive wires may be varied and controlled in order to determine the optimal location for the dilation introducer and/or access cannula.

Implant

With respect to the implant 80 described above, the implant 80 can comprise any of a variety of types of interbody devices configured to be placed between vertebral bodies. The implant 80 can be formed from a metal (e.g., titanium) or a non-metal material such as plastics, PEEK™, polymers, and rubbers. Further, the implant components can be made of combinations of non-metal materials (e.g., PEEK™, polymers) and metals. The implant 80 can be configured with a fixed or substantially fixed height, length, and width as shown, for example, in the embodiment of FIG. 13. In other embodiments, the implant can be configured to be expandable along one or more directions. For example, in certain embodiments the height of the implant can be expanded once the device advanced through the access cannula and positioned between vertebral bodies (e.g., within the disc space within the annulus).

FIGS. 21-27 illustrate an implant 500 having an first, reduced profile configuration and a second, increased profile configuration. In general, the implant can include first body portion 502 (FIGS. 23 and 24) and a second portion 520 (FIGS. 25 and 26) which are shown together in FIG. 27. As will be described below, in one arrangement, the implant 500 can be used to maintain separation between adjacent vertebrae while preserving at least some degree of motion between two adjacent vertebrae. In one arrangement, portions of the intervertebral implant 500 can be configured to be inserted through the Kambin triangle in a first, reduced cross-sectional profile configuration, and, once a portion of the implant 500 is passed through the Kambin triangle, the implant 500 can be converted into the second, increased profile configuration in which the device can engage and maintain separation of the adjacent vertebra while still allowing least some degree of motion between two adjacent vertebrae.

With reference to FIGS. 21 to 24, the first body portion 502 can include a first member 504 and a second member 508. The first member 504 and the second member 508 can be pivotable around a first shaft 514 from the low profile configuration, shown in FIGS. 23 and 24, to the larger profile configuration, shown in FIGS. 21 and 22. As described herein, certain features of the implant facilitate delivery through a smaller access site, such as through Kambin's triangle, while still providing structural support across a larger surface area in the intervertebral space once enlarged. As mentioned earlier, access through Kambin's triangle can reduce trauma to the patient, particularly by avoiding removal of the facet joint. Kambin's triangle also provides a viable access site for patients who are not suitable candidates for the anterior approach to spinal surgery.

Figure 22:
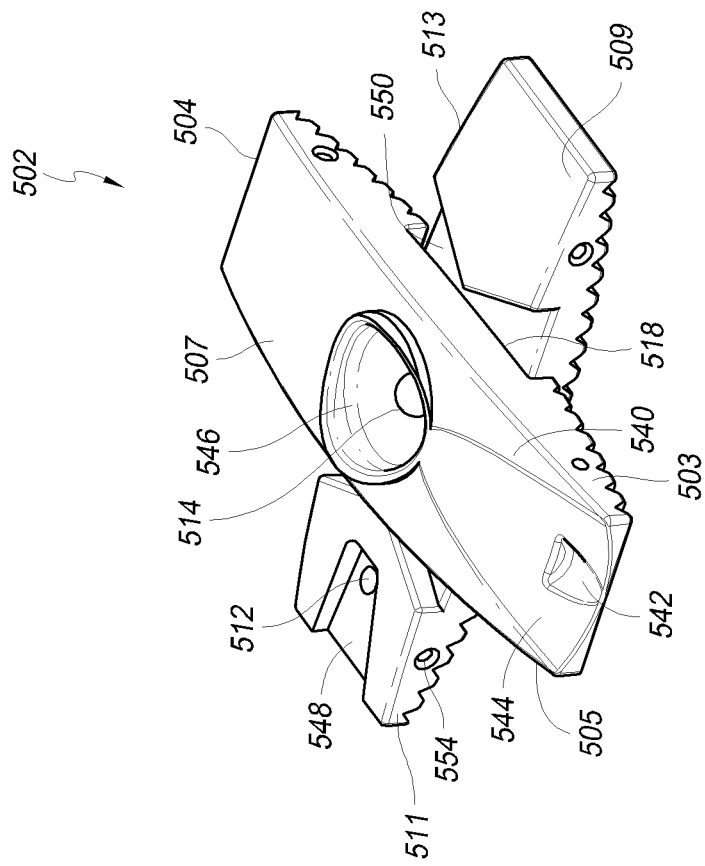
FIGS. 21-22 illustrate a first body portion of an implant in an open configuration.
Figure 21:
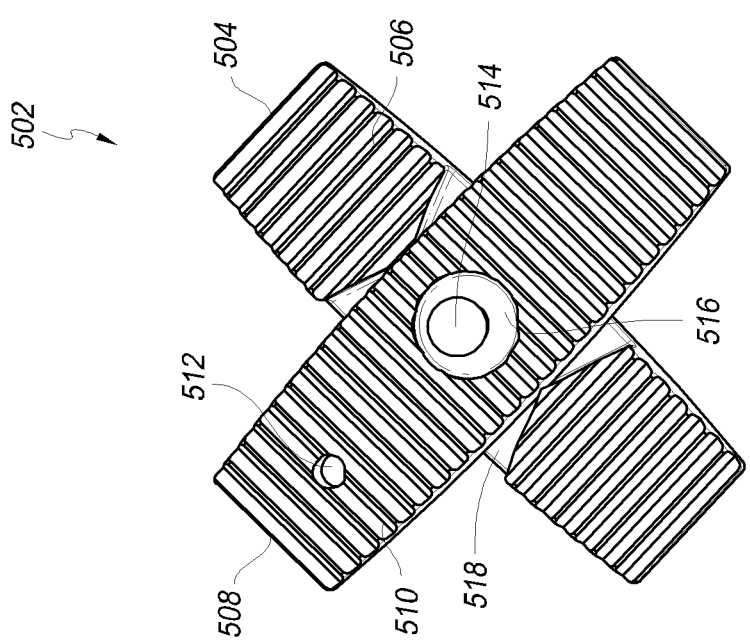
Figure 24:
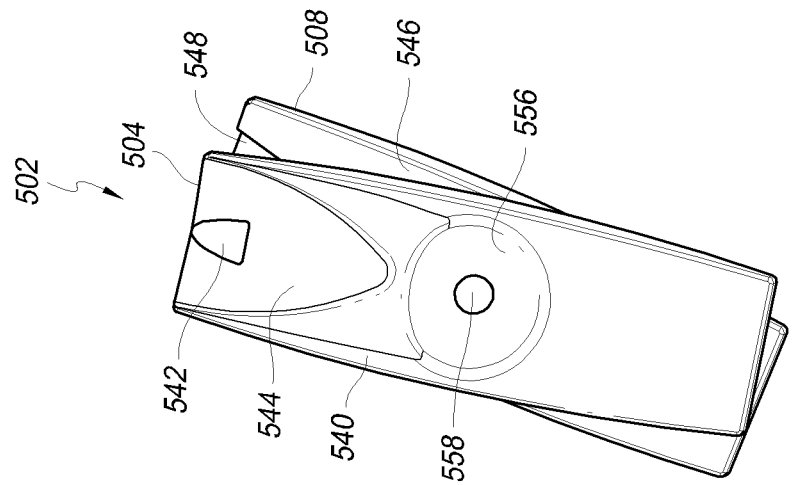
FIGS. 23-24 illustrate the first body portion in a closed configuration.

With reference to FIGS. 21 and 22, the first member 504 can include a first surface 506, a second surface 507, and side surfaces 503, 505. The second member 508 can include a first surface 510, a second surface 509, and side surfaces 511, 513. One or more surfaces of the first member 504 and the second member 508 can include surface modifications to facilitate tissue growth and/or help the implant engage the adjacent vertebrae. The surface modifications can include, but are not limited to, textured surfaces, ridges, grooves, apertures, and/or bioactive coatings.

The first body portion 502 can include one or more textured surfaces. The textured surfaces can include microscopic roughness or more easily visible protrusions. For example, one or more surfaces of the first body portion can include a ribbed surface. As shown in FIG. 21, the first surface 506 of the first member 504 can include a ribbed surface, and the first surface 510 of the second member 508 can include a ribbed surface.

The first body portion 502 can include one or more apertures to facilitate osseointegration within the intervertebral space. As shown in FIG. 22, the side surfaces 503, 505 of the first member 504 and the side surfaces 511, 513 of the second member 508 can include one or more apertures 554. More specifically, the first member 504 can include two apertures 554 on side surface 503 and two apertures 554 on side surface 505, and the second member 508 can include two apertures on side surface 511 and two apertures on side surface 513. The apertures can facilitate circulation and bone growth throughout the intervertebral space and through the implant. In such implementations, the apertures can thereby facilitate integration of the implant with the surrounding materials.

The first body portion 502 can be coated with one or more bioactive substances, such as antibiotics, chemotherapeutic substances, angiogenic growth factors, substances for accelerating the healing of the wound, growth hormones, anti-thrombogenic agents, bone growth accelerators or agents, and the like.

Figure 23:
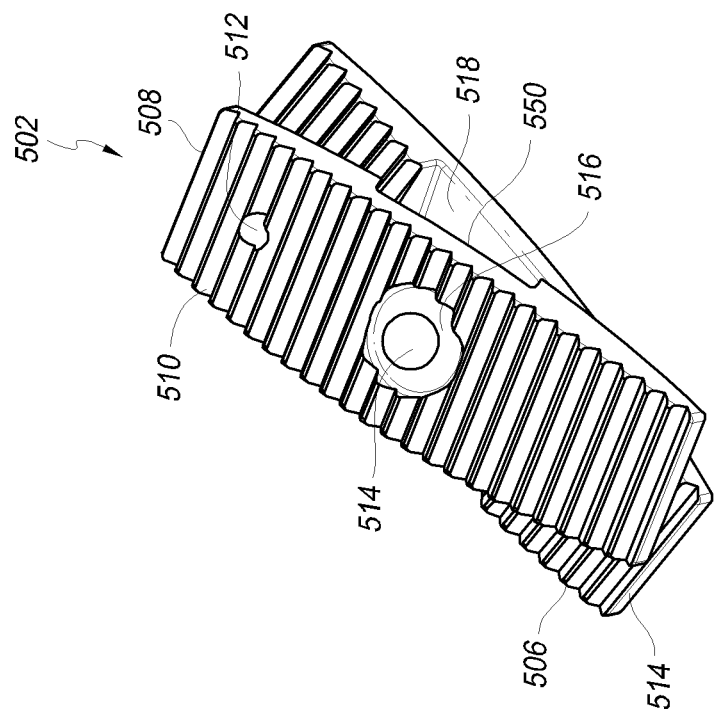

The first body portion 502 can include an open configuration, shown in FIGS. 21 and 22, and a closed or low profile configuration, shown in FIG. 23. In the open or enlarged profile configuration, the first member 504 can be perpendicular or substantially perpendicular to the second member 508. In the closed configuration, the first member 504 can be substantially parallel or parallel to the second member 508.

The closed configuration facilitates delivery of the first body portion 502 through a smaller access site, such as Kambin's triangle, while the open configuration has a greater surface area to provide greater structural integrity in the intervertebral space.

The first body portion 502 can include one or more motion limiting portions 518, 550. Motion limiting portions 518, 550 can limit the rotational movement of the first member 504 relative to the second member 508. The motion limiting portions 518, 550 can take on different configurations. For example, as shown in FIGS. 21 and 22, the motion limiting portions 518, 550 can permit limited clockwise and counterclockwise rotation. As another example, the motion limiting portions will only permit limited clockwise rotation, as shown by motion limiting portion 572 in FIG. 25.

The first member 504 can translate along a central axis of the first shaft. As shown in FIG. 23, when the first body portion 502 is in the closed configuration, the motion limiting portion 518 can be spaced apart from motion limiting portion 550. In the closed configuration, the first body portion 502 is suitable for delivery through a deployment tool. In contrast, as shown in FIG. 22, when the first body portion is in the open configuration, the motion limiting portion 518 can abut the motion limiting portion 550. Once in the intervertebral space, the first body portion 502 can transition from the closed configuration to the open configuration. The motion limiting portions 518, 550 can prevent the first body portion 502 from returning to the closed configuration.

The first body portion 502 can transition from a closed configuration to an open configuration via a user-actuated mechanism. As another example, the first body portion 502 can be spring-loaded. In the spring-loaded example, a tubular member, such as access cannula 30, can restrain the first body portion 502 to a closed configuration, but when the first body portion 502 is delivered from the tubular member, the first body portion 502 can transition to the open configuration. A deployment tool having forceps can also restrain the first body portion 502 to the closed configuration. Releasing the first body portion from the deployment tool can transition the first body portion 502 from the closed configuration to the open configuration.

The first body portion 502 can also include one or more depressions 542, 548 to facilitate interaction with a deployment tool.

The first body portion 502 can include a metal (e.g., titanium) or a non-metal material such as plastics, PEEK™, polymers, and rubbers. Further, the implant components can be made of combinations of non-metal materials (e.g., PEEK™, polymers) and metals.

The first body portion 502 can be configured with a height, length, and width suitable for delivery through the access cannula and positioning between vertebral bodies (e.g., within the disc space within the annulus). The first member 504 can have a uniform width, or the first member 504 can include a tapered width. Further, the first member 504 can include a uniform thickness, or the first member 504 can include a tapered thickness. The second member 508 can have dimensions identical to or substantially similar to the first member 504.

Figure 26:
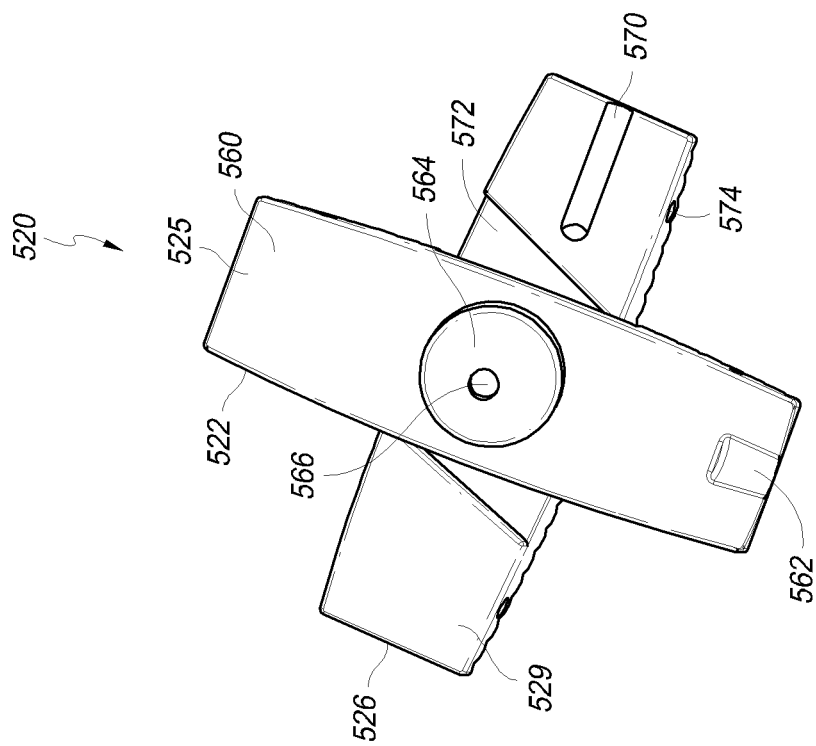
FIGS. 25-26 illustrate a second body portion of the implant in an open configuration.
Figure 25:
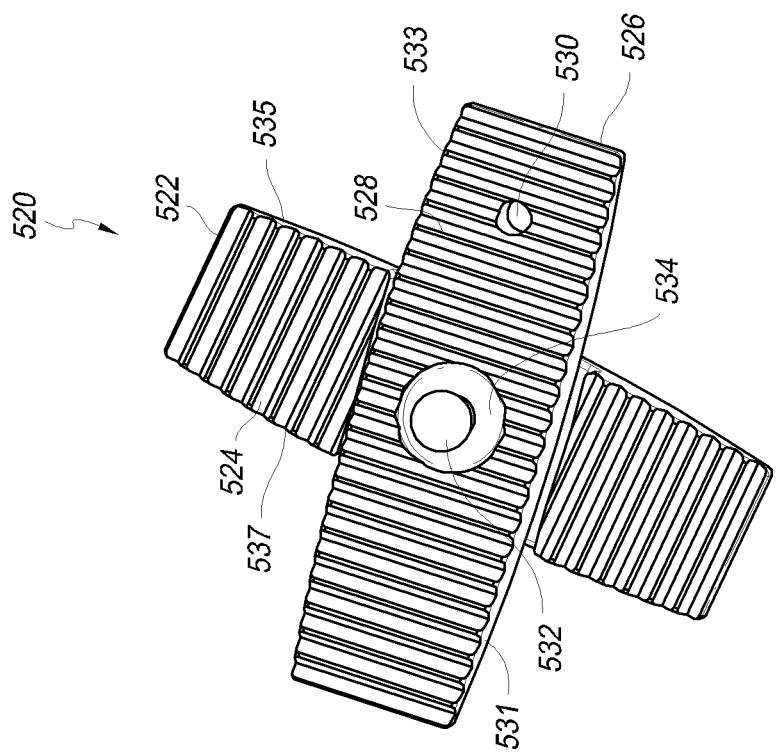
Figure 27:
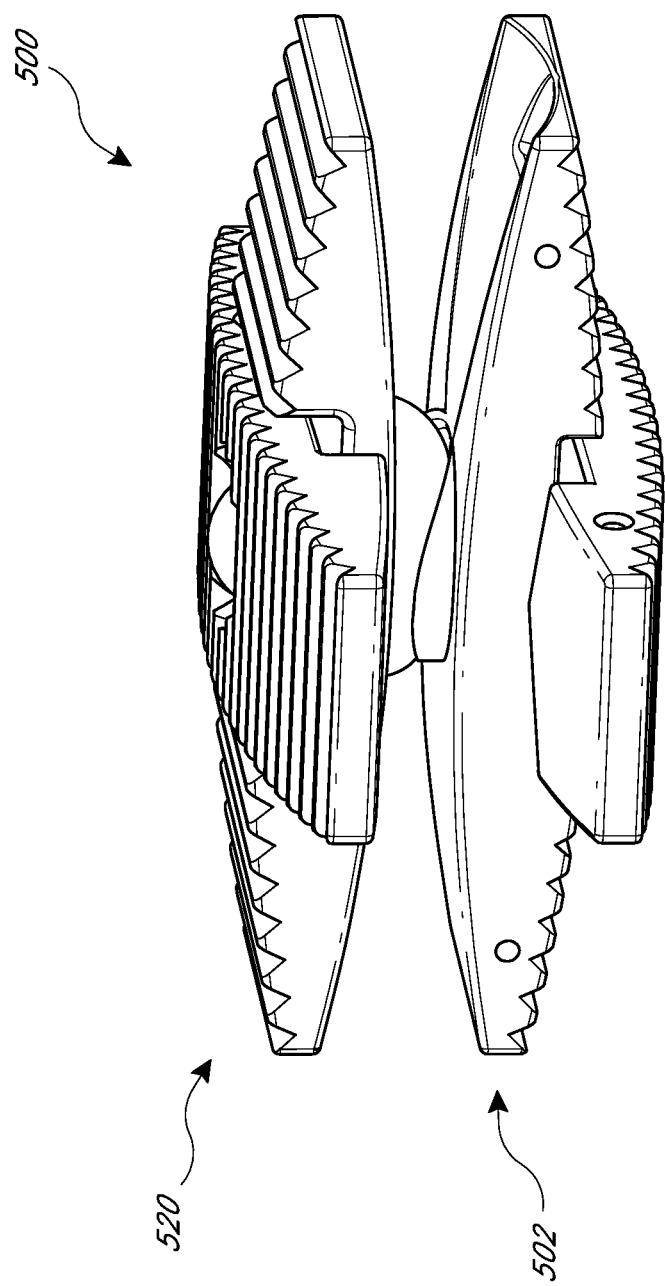
FIG. 27 illustrates an intervertebral implant including the first body portion and the second body portion illustrated in FIGS. 21-26.

As shown in FIG. 27, the implant 500 can include the first body portion 502 and the second body portion 520. The second portion 520 can be the same as or substantially similar to the first body portion 502 discussed in reference to FIG. 21. FIGS. 25-26 illustrate a second body portion 520. The second body portion 520 can include one or more of the first body portion 502 features discussed above. Generally, the second body portion 520 can include a first member 522 and a second member 526. The first member 522 can include a first surface 524, a second surface 525, and side surfaces 535, 537. The second member 526 can include a first surface 528, a second surface 529, and side surfaces 531, 533. The second body portion 520 can also include a second shaft 532. The first member 522 and the second member 526 can be pivotable around the second shaft 532.

The two-piece implant 500 facilitates delivery of the implant through a smaller access site. After the implant is assembled in the intervertebral space, the two-piece implant can fill a larger space between two vertebrae than would be possible with a single component system using a similarly sized access site or access cannula.

The first body portion 502 can include a first joint portion 546, and the second body portion 520 can include a second joint portion 564. The first joint portion 546 can removably connect to the second joint portion 564. In certain aspects, the first joint portion 546 and the second joint portion 564 can form a ball and socket joint. The ball and socket joint permits motion along multiple axes. The first joint portion 546 and the second joint portion 564 can also take on any other joint configuration, including, but not limited to, a hinge joint, pivot joint, or saddle joint depending on the desirable amount of movement. In some instances, it may be desirable to limit the number of axes along which the first member 504 is capable of moving relative to the second member 508.

As shown in FIG. 27, the first body portion 502 and the second body portion 520 can be positioned such that the textured surfaces of first and second body portions 502, 520 face outward. The outward facing, textured surfaces facilitate tissue growth between the implant and the adjacent vertebrae.

Method of Delivering an Implant

The first body and second portions 502, 520 of the implant 500 can be delivered through the Kambin triangle utilizing the techniques and devices described above with reference to FIGS. 1-20B. The first body portion 502 can be delivered using any type of deployment tool 600 capable of engaging the first body portion 502, including, but not limited to a deployment tool having a surgical forceps feature. The deployment tool 600 can deliver the first body portion 502 through a posterolateral approach. The posterolateral approach can include delivering the first body portion 502 through Kambin's triangle without removing a facet joint.

Figure 28:
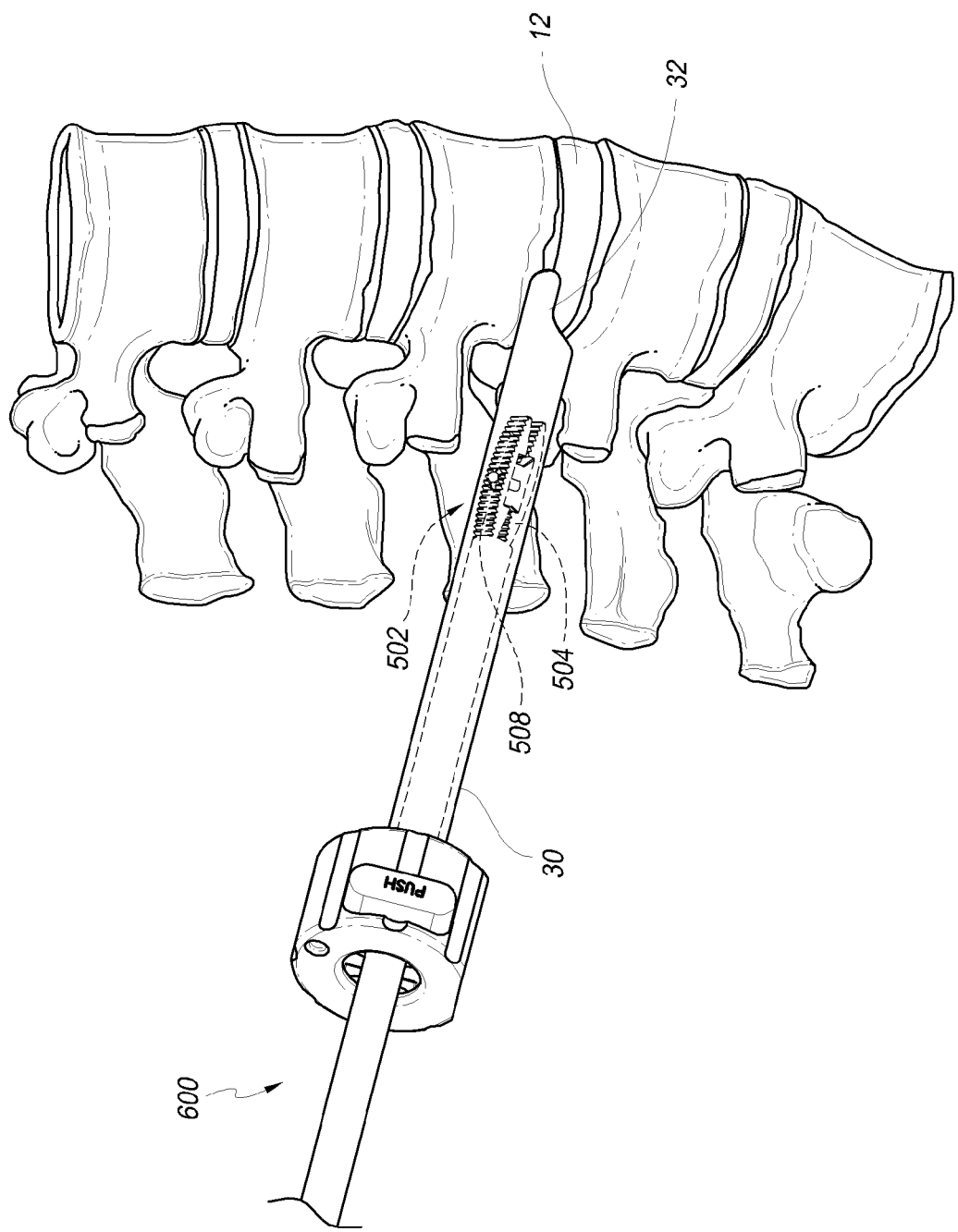
FIG. 28 illustrates a delivery of the first body portion through an access cannula.

As shown in FIG. 28, the deployment tool 600 can engage the first body portion 502 and deliver the first body portion 502 through the cannula 30 and into the intervertebral space. The cannula 30 can gain access to the intervertebral space using any of the methods and/or devices described above.

Once the first body portion 502 is in the intervertebral space, the implant can transition from the closed configuration to the open configuration. Deployment tool 600 can include an actuation mechanism configured to transition the first body portion 502 from the closed configuration to the open configuration. In another arrangement, the first body portion 502 can be spring-loaded to automatically transition to the open configuration when released from the deployment tool 600 or the cannula 30.

A filler can be injected into the intervertebral space. The filler can include any type of bone graft substance, bone cement, a carrier medium carrying bone morphogenetic proteins, or any other bone void fillers.

The deployment tool 600 can engage the second body portion 520 and deliver the second body portion 520 into the intervertebral space. Similar to the first body portion 502, the second body portion 520 can transition from the closed configuration to the open configuration using a user-actuated mechanism or a spring-loaded mechanism.

The deployment tool 600 can position the second body portion 520 relative to the first body portion 502. For example, the deployment tool 600 can connect the first joint portion 546 to the second joint portion 564, such that the second body portion 520 is capable of controlled movement relative to the first body portion 502. In some designs, the first joint portion 546 and the second joint portion 564 form a ball and socket joint.

Deployment Tool

Figure 29:
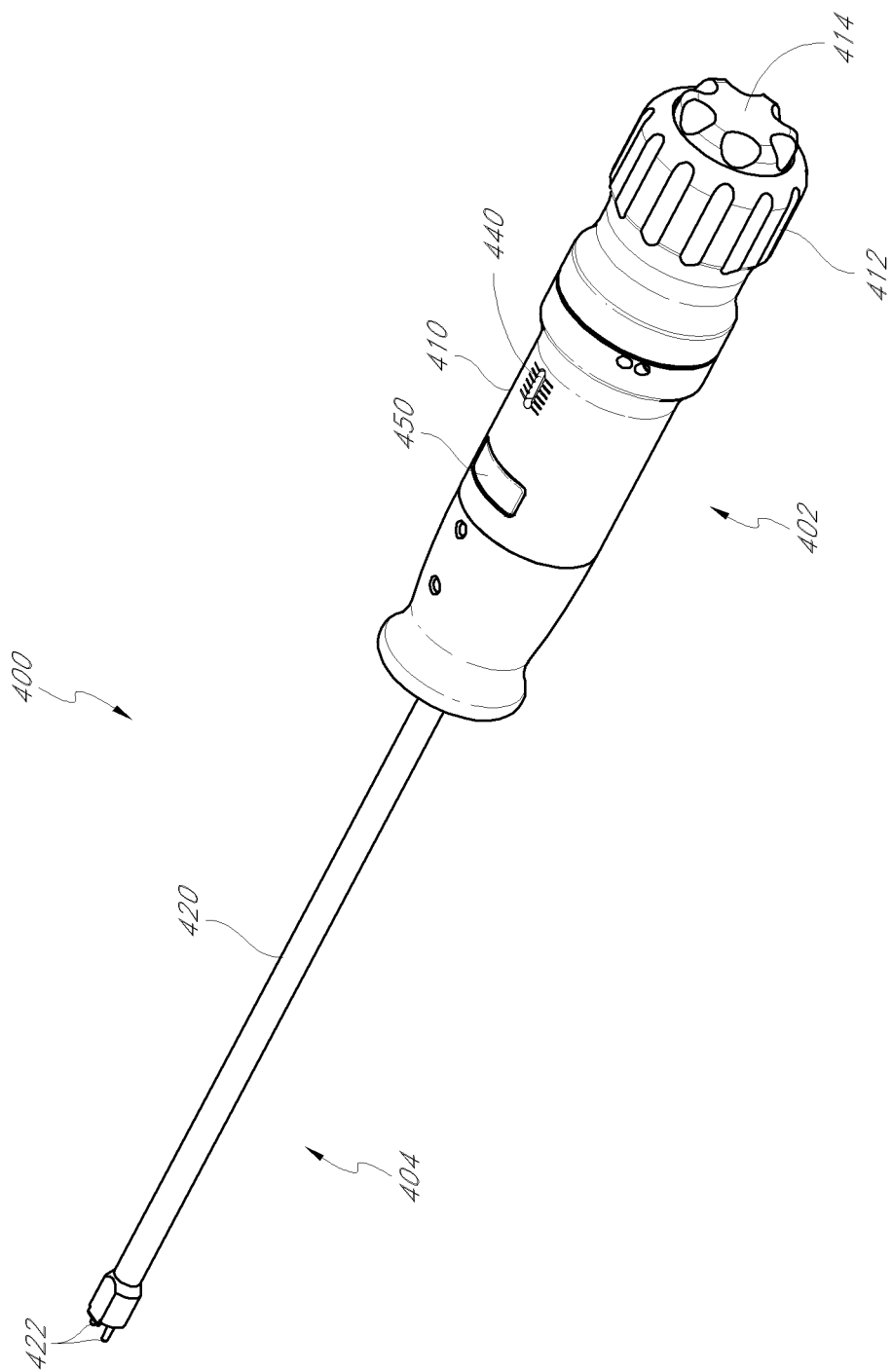
FIG. 29 is a perspective view of a deployment tool according to an embodiment.

Referring now to FIG. 29, there is illustrated a perspective view of a deployment tool 400 according to another embodiment. The tool 400 can comprise a handle section 402 and a distal engagement section 404. The handle portion 402 can be configured to be held by a user and can comprise various features to facilitate implantation and deployment of the implant.

According to an embodiment, the handle section 402 can comprise a fixed portion 410, and one or more rotatable portions, such as the rotatable deployment portion 412 and the rotatable tethering portion 414. In such an embodiment, the tethering portion 414 can be used to attach the implant to the tool 400 prior to insertion and deployment. The deployment portion 412 can be used to actuate the implant and rotate the actuator shaft thereof for expanding the implant. Then, after the implant is expanded and properly placed, the tethering portion 414 can again be used to untether or decouple the implant from the tool 400.

Further, the distal engagement section 404 can comprise a fixed portion 420, an anti-torque component 422, a tethering rod (element 424 shown in FIG. 30), and a shaft actuator rod (element 426 shown in FIG. 30) to facilitate engagement with and actuation of the implant 200. The anti-torque component 422 can be coupled to the fixed portion 420. As described above with reference to FIGS. 21A-B, in an embodiment, the implant 200 can comprise one or more anti-torque structures 250. The anti-torque component 422 can comprise one or more protrusions that engage the anti-torque structures 250 to prevent movement of the implant 200 when a rotational force is applied to the actuator shaft 210 via the tool 400. As illustrated, the anti-torque component 422 can comprise a pair of pins that extend from a distal end of the tool 400. However, it is contemplated that the implant 200 and tool 400 can be variously configured such that the anti-torque structures 250 and the anti-torque component 422 interconnect to prevent a torque being transferred to the implant 200. The generation of the rotational force will be explained in greater detail below with reference to FIG. 30, which is a side-cross sectional view of the tool 400 illustrating the interrelationship of the components of the handle section 402 and the distal engagement section 404.

For example, as illustrated in FIG. 30, the fixed portion 410 of the handle section 402 can be interconnected with the fixed portion 420 of the distal engagement section 404. The distal engagement section 404 can be configured with the deployment portion 412 being coupled with the shaft actuator rod 426 and the tethering portion 414 being coupled with the tethering rod 424. Although these portions can be coupled to each other respectively, they can move independently of each other and independently of the fixed portions. Thus, while holding the fixed portion 410 of the handle section 402, the deployment portion 412 and the tethering portion 414 can be moved to selectively expand or contract the implant or to attach the implant to the tool, respectively.

In the illustrated embodiment, these portions 412, 414 can be rotated to cause rotation of an actuator shaft 210 of an implant 200 engaged with the tool 400.

As shown in FIG. 30, the tether rod 424 can comprise a distal engagement member 430 being configured to engage a proximal end of the actuator shaft 210 of the implant 200 for rotating the actuator shaft 210 to thereby expand the implant from an unexpanded state to and expanded state. The tether rod 424 can be configured with the distal engagement member 430 being a threaded distal section of the rod 424 that can be threadably coupled to an interior threaded portion of the actuator shaft 210.

In some embodiments, the tool 400 can be prepared for a single-use and can be packaged with an implant preloaded onto the tool 400. This arrangement can facilitate the use of the implant and also provide a sterile implant and tool for an operation. Thus, the tool 400 can be disposable after use in deploying the implant.

Referring again to FIG. 29, an embodiment of the tool 400 can also comprise an expansion indicator gauge 440 and a reset button 450. The expansion indicator gauge 440 can be configured to provide a visual indication corresponding to the expansion of the implant 200. For example, the gauge 440 can illustrate an exact height of the implant 200 as it is expanded or the amount of expansion. As shown in FIG. 30, the tool 400 can comprise a centrally disposed slider element 452 that can be in threaded engagement with a thread component 454 coupled to the deployment portion 412.

In an embodiment, the slider element 452 and an internal cavity 456 of the tool can be configured such that the slider element 452 is provided only translational movement in the longitudinal direction of the tool 400. Accordingly, as the deployment portion 412 is rotated, the thread component 454 is also rotated. In such an embodiment, as the thread component 454 rotates and is in engagement with the slider component 452, the slider element 452 can be incrementally moved from an initial position within the cavity 456 in response to the rotation of the deployment portion 412. An indicator 458 can thus be longitudinally moved and viewed to allow the gauge 440 to visually indicate the expansion and/or height of the implant 200. In such an embodiment, the gauge 440 can comprises a transparent window through which the indicator 458 on the slider element 452 can be seen. In the illustrated embodiment, the indicator 458 can be a marking on an exterior surface of the slider element 452.

In embodiments where the tool 400 can be reused, the reset button 450 can be utilized to zero out the gauge 440 to a pre-expansion setting. In such an embodiment, the slider element 452 can be spring-loaded, as shown with the spring 460 in FIG. 30. The reset button 450 can disengage the slider element 452 and the thread component 454 to allow the slider element 452 to be forced back to the initial position.

Additional details and embodiments of an expandable implant can be found in U.S. Patent Application No 2008/0140207, filed Dec. 7, 2007 as U.S. patent application Ser. No. 11/952,900, the entirety of which is hereby incorporated by reference herein.

Bone Rasp

Another example of a surgical tool for use through the access cannula is a bone rasp. A rasp tool can be configured to be inserted through the access cannula 30 into the intervertebral disc space. The rasping tool can then be used to abrade or file the inferior surface of the superior vertebrae and/or the superior surface of the inferior vertebrae. The rasping tool can include an elongated body and a scraping component. A handle may be proximally attached to the elongated body.

The entire assembly can be dimensioned such that the rasping tool can slide longitudinally within the access cannula 30. In use, the rasp tool may be inserted through the access cannula until it reaches the intervertebral disc space. Using the handle, a physician may slide the elongate body and scraping component backward and forward relative to the access cannula 30. In certain embodiments, the elongate body may freely rotate within the access cannula 30, in order to permit the physician to rasp a surface at any desired angle. In other embodiments, the orientation of the elongate body may be fixed, such that rasping is only permitted along a predetermined angle relative to the access cannula 30.

In certain embodiments, the rasping tool may be expandable. For example, a rasp tool can be configured to define an unexpanded configuration. When the tool is initially inserted into the working sleeve, the tool can be positioned in the unexpanded configuration. After the tool is advanced into the intervertebral disc, the tool can be expanded to the expanded configuration.

The tool can include an elongated body and one or more scraping components. The scraping components can each include an outer surface that is configured to scrape or create friction against the disc. For example, the outer surfaces can be generally arcuate and provide an abrasive force when in contact with the interior portion of the disc. In particular, it is contemplated that once the tool is expanded, the scraping components can rasp or scrape against the vertebral end plates of the disc from within an interior cavity formed in the disc. In this manner, the tool can prepare the surfaces of the interior of the disc by removing any additional gelatinous nucleus material, as well as smoothing out the general contours of the interior surfaces of the disc. The rasping may thereby prepare the vertebral endplates for fit with the implant as well as to promote bony fusion between the vertebrae and the implant. Due to the preparation of the interior surfaces of the disc, the placement and deployment of the implant will tend to be more effective.

It is contemplated that the tool can comprise an expansion mechanism that allows the scraping components to move from the unexpanded to the expanded configuration. For example, the tool can be configured such that the scraping components expand from an outer dimension or height of approximately 9 mm to approximately 13 mm. In this regard, the expansion mechanism can be configured similarly to the expansion mechanisms of the implants disclosed herein, the disclosure for which is incorporated here and will not be repeated.

Further, it is contemplated that the scraping components can comprise one or more surface structures, such as spikes, blades, apertures, etc. that allow the scraping components to not only provide an abrasive force, but that also allowed the scraping components to remove material from the disc. In this regard, as in any of the implementations of the method, a cleaning tool can be used to remove loosened, scraped, or dislodged disc material. Accordingly, in various embodiments of the methods disclosed herein, and embodiment of the tool can be used to prepare the implant site (the interior cavity of the disc) to optimize the engagement of the implant with the surfaces of the interior of the disc (the vertebral end plates).

After the implant site has been prepared, the implant can be advanced through the access cannula and into the disc cavity. Once positioned, the implant can be expanded to its expanded configuration. For example, the implant can be expanded from approximately 9 mm to approximately 12.5 mm. Additionally, other materials or implants can then be installed prior to the removal of the access cannula and closure of the implant site.

The specific dimensions of any of the embodiment disclosed herein can be readily varied depending upon the intended application, as will be apparent to those of skill in the art in view of the disclosure herein. Moreover, although the present inventions have been described in terms of certain preferred embodiments, other embodiments of the inventions including variations in the number of parts, dimensions, configuration and materials will be apparent to those of skill in the art in view of the disclosure herein. In addition, all features discussed in connection with any one embodiment herein can be readily adapted for use in other embodiments herein to form various combinations and sub-combinations. The use of different terms or reference numerals for similar features in different embodiments does not imply differences other than those which may be expressly set forth. Accordingly, the present inventions are intended to be described solely by reference to the appended claims, and not limited to the preferred embodiments disclosed herein.

Three-Part Implant

Figure 31A:
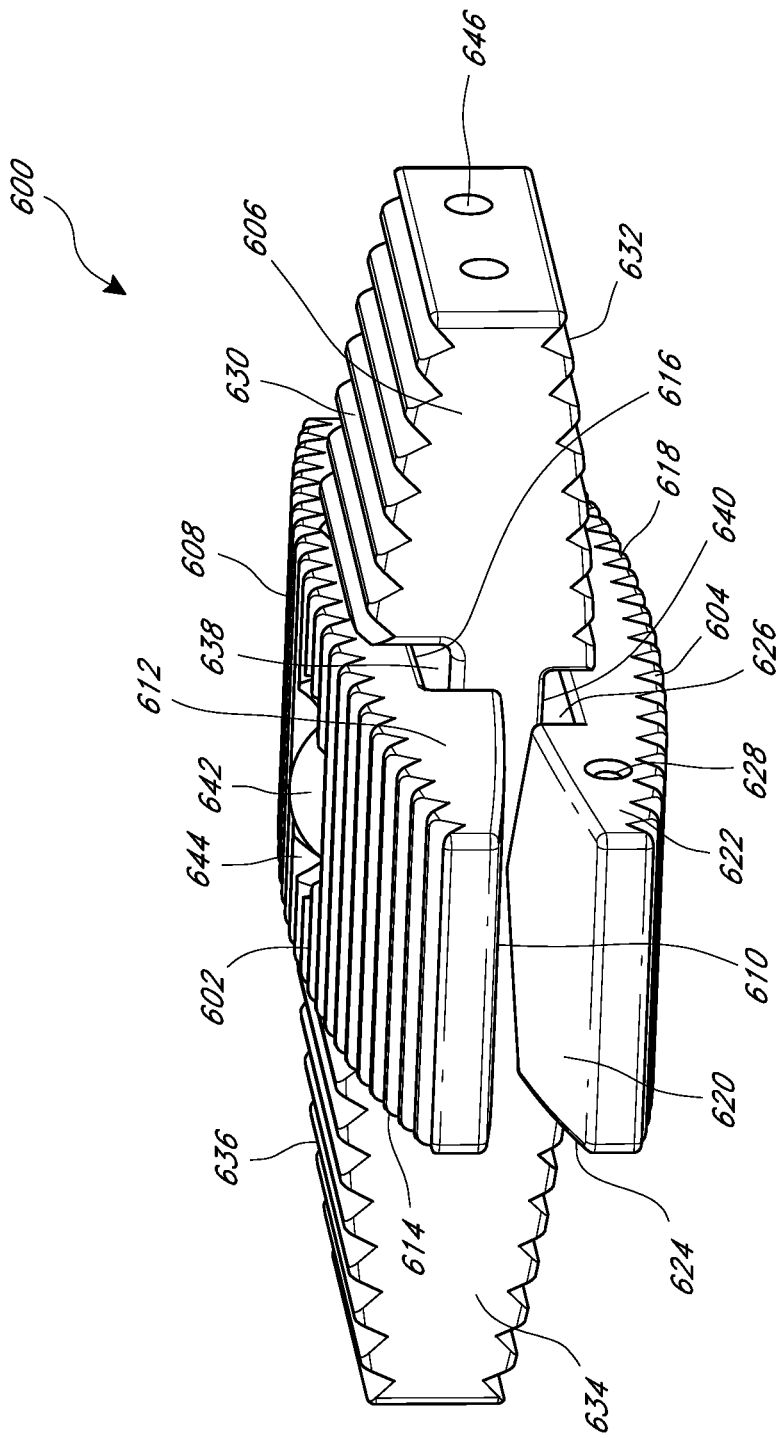
FIG. 31A illustrates a perspective view of a three-part implant.

FIG. 31A illustrates an implant 600 generally having an upper body portion 602, a lower body portion 604, and a central body portion 606. The upper and lower body portions 602, 604 can be configured to be inserted through the Kambin triangle in a first, reduced profile configuration and converted into a second, increased profile configuration within the vertebral space. For example, the upper and lower body portions 602, 604 can move to the second, increased profile configuration when the central body portion 606 is inserted between the upper and lower body portions 602, 604. As another example, the upper and lower body portions 602, 604 can be spring-loaded to move to the second, increased profile configuration when released from the deployment tool. In the increased profile configuration, the implant 600 can engage and maintain separation of the adjacent vertebra while still allowing least some degree of motion between two adjacent vertebrae.

As shown in FIG. 31A, once assembled, the upper and lower body portions 602, 604 can be generally parallel to each other. The central body portion 606 can be positioned between the upper and lower body portions 602, 604 and positioned generally perpendicular to the upper and lower body portions 602, 604. Although, in certain variants, the central body portion 606 can be positioned at another angle relative to the upper and lower body portions 602, 604, such as at about 30 degrees, about 45 degrees, or about 60 degrees.

The upper, lower, and central body portions 602, 604, 606 can include a metal (e.g., titanium) or a non-metal material such as rubbers, plastics, Teflon®, PEEK, or other polymers. Further, the implant components can be constructed from combinations of non-metal materials and metals. For example, the upper and lower body portions 602, 604 be constructed from titanium, while the central body portion 606 can be constructed from PEEK or Teflon®. The central body portion 606 can act as a shock absorber for the implant.

The upper and lower body portions 602, 604 can include one or more of the features of the first member and second members of the first and second body portions 502, 520 of implant 500. For example, the upper body portion 602 can include a first surface 608, a second surface 610, and side surfaces 612, 614. The first and second surfaces 608, 610 can be generally curved or generally flat. As shown in FIG. 31A, the first and second surfaces 608, 610 can be generally curved in opposite directions such that end portions of the upper body portion 602 have a thickness that is less than a thickness closer to the center of the upper body portion 602. In certain variants, the end portions of the upper body portion 602 have a thickness that is substantially the same as a thickness closer to the center of the upper body portion 602.

Similarly, the lower body portion 604 can include a first surface 618, a second surface 620, and side surfaces 622, 624. The first and second surfaces 618, 620 can be generally curved or generally flat. As shown in FIG. 31A, the first and second surfaces 618, 620 can be generally curved in opposite directions such that end portions of the lower body portion 604 have a thickness that is less than a thickness closer to the center of the lower body portion 604. In certain variants, end portions of the lower body portion 604 have a thickness that is substantially the same as a thickness closer to the center of the lower body portion 604.

The upper and lower body portions 602, 604 can be configured such that their respective second surfaces 610, 620 face each other, while the first surfaces 608, 618 face outward. In some arrangements, the upper and lower body portions 602, 604 can be directly or indirectly connected together, while still permitting movement between the reduced profile configuration and the increased profile configuration. For example, the implant 600 can include one or more linkages connecting the upper and lower body portions 602, 604. The linkages can connect the side surfaces of the upper and lower body portions 602, 604, connect the second surfaces 610, 620 of the upper and lower body portions 602, 604, and/or connect the ends of the upper and lower body portions 602, 604.

In some instances, the upper and lower body portions 602, 604 can be spring-loaded. In the spring-loaded example, a tubular member, such as access cannula 30, can restrain the upper and lower body portions 602, 604 to the reduced profile configuration, but when the upper and lower body portions 602, 604 are delivered from the tubular member, the upper and lower body portions 602, 604 can transition to the increased profile configuration. A deployment tool having forceps can also restrain the upper and lower body portions 602, 604 to the closed configuration. Releasing the first body portion from the deployment tool can transition the upper and lower body portions 602, 604 from the reduced profile configuration to the increased profile configuration. The upper and lower body portions 602, 604 can include one or more depressions, similar to depressions 542, 562 of implant 500 to facilitate interaction with a deployment tool.

Figure 31B:
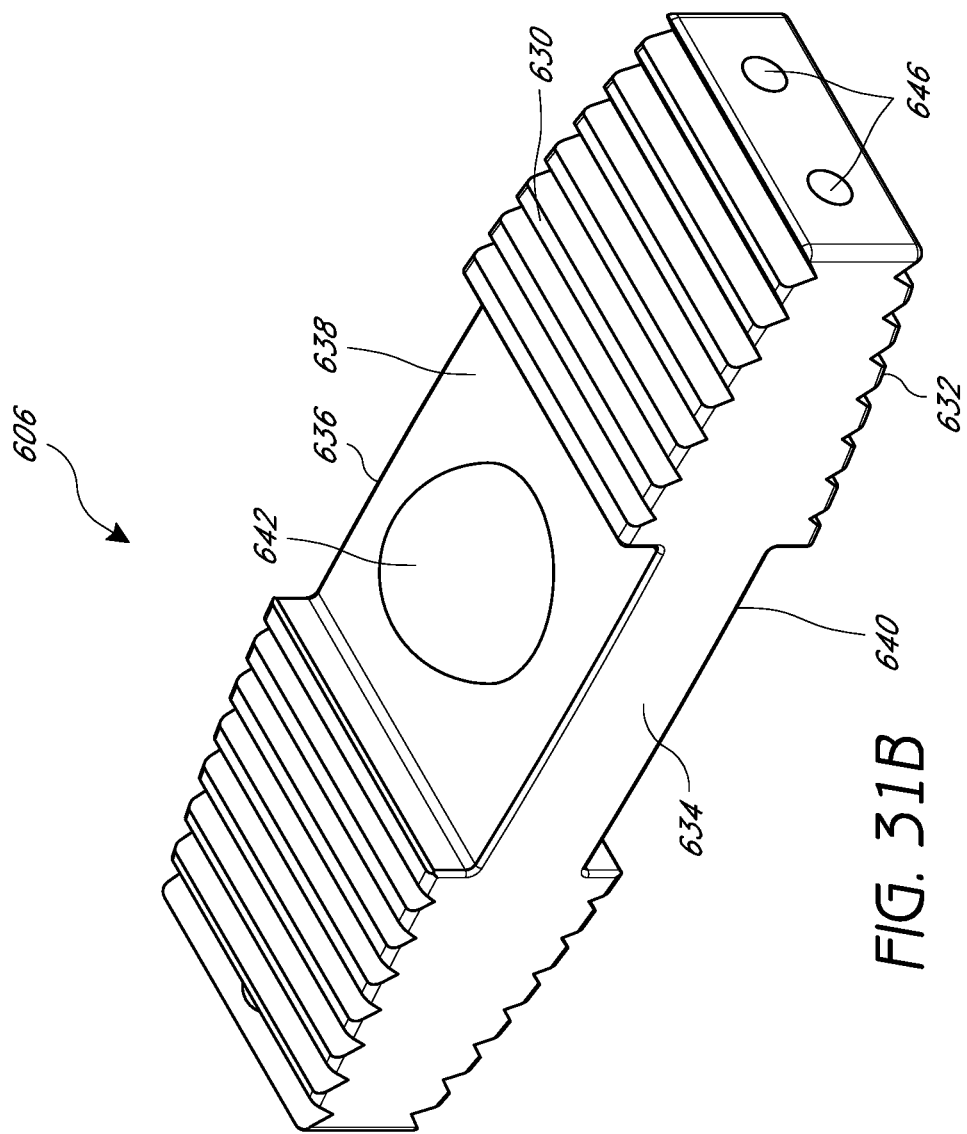
FIG. 31B illustrates a perspective view of a central body portion of the three-part implant shown in FIG. 31A.

As shown in FIG. 31B, the central body portion can include a first surface 630, a second surface 632, and side surfaces 634, 636. The first and second surfaces 630, 632 can be generally curved or generally flat. As shown in FIG. 31B, the first and second surfaces 630, 632 can be generally curved in opposite directions such that the end portions of the central body portion 606 have a thickness that is less than a thickness closer to the center of the central body portion 606. In certain variants, the end portions of the central body portion 606 can have a thickness that is substantially the same as a thickness closer to the center of the central body portion 606.

The upper and/or lower body portions 602, 604 can include motion limiting portions 616, 626 (e.g., notch, cutout, indentation, groove, or likewise). For example, the motion limiting portion 616 can be positioned along the second surface 610 of the upper body portion 602 and configured to interact with a corresponding motion limiting feature 638 on a first surface 630 of the central body portion 606. The motion limiting portion 616 can be centered along a length of the upper body portion 602.

The motion limiting portion 626 can be positioned along the second surface 620 of the lower body portion 604 and configured to interact with a corresponding motion limiting feature 640 on a second surface 632 of the central body portion 606. The motion limiting portion 626 can be centered along a length of the lower body portion 604.

The motion limiting features 638, 640 (e.g., notch, cutout, indentation, groove, or likewise) can be centered along a length of the central body portion 606. The section of the central body portion 606 having the motion limiting features 638, 640 can have a thickness that is less than a thickness closer to the end portions of the central body portion 606.

The motion limiting portions 616, 626 can limit rotational movement of the upper and/or lower body portions 602, 604 relative to the central body portion 606. In some instances, the motion limiting portions 616, 626 can permit limited clockwise and/or counter-clockwise rotation along a horizontal and/or vertical plane.

In some arrangements, the upper and/or lower body portions 602, 604 can include socket portions. The socket portions can take on different configurations. For example, as shown in FIG. 31A, the socket portion 644 can extend through the thickness of the upper body portions 602. As another example, the socket portions be shaped similarly to joint portion 546, shown in FIG. 22, and disposed along the second surfaces 610, 620 of the upper and lower body portions 602, 604.

The socket portions can be generally centered along a length of the upper and lower body portions 602, 604, for example, within the motion limiting portions 616, 626. The ball portion 642 can be generally centered along a length of the center body portion 606, for example, the ball portion can include a hemispherical portion disposed within each of the motion limiting features 638, 640. The socket portions can be configured to interact with ball portion 642 of the central body portion 606 to form a ball and socket joint. The ball and socket joint permits motion along multiple axes.

In some arrangements, the upper and lower body portions 602, 604 can include ball portions disposed along the second surfaces 610, 620 of the upper and lower body portions 602, 604, while the central body portion 606 can include socket portions configured to interact with the ball portions.

Although FIG. 31A illustrates a ball and socket joint, other joint configurations can be used, including, but not limited to, a hinge joint, pivot joint, or saddle joint depending on the desirable amount of movement.

One or more surfaces of the upper, lower, and/or central body portions 602, 604, 606 can include surface modifications to facilitate tissue growth and/or help the implant engage the adjacent vertebrae. The surface modifications can include, but are not limited to, textured surfaces, ridges, grooves, apertures, and/or bioactive coatings. As shown in FIG. 31A, the first surfaces 608, 618 can include ribbed features. Further, the first and second surfaces 630, 632 of the central body portion 606 can include ribbed features.

The upper, lower, and/or central body portions 602, 604, 606 can include one or more apertures to facilitate osseointegration within the intervertebral space. For example, the side surfaces 612, 614, 622, 624, 632, 634 can include one or more apertures 628. The apertures 628 can facilitate circulation and bone growth throughout the intervertebral space and through the implant, thereby integrating the implant with the surrounding materials.

The upper, lower, and/or central body portions 602, 604, 606 can be coated with one or more bioactive substances, such as antibiotics, chemotherapeutic substances, angiogenic growth factors, substances for accelerating the healing of the wound, growth hormones, anti-thrombogenic agents, bone growth accelerators or agents, and the like.

As discussed above, the upper and lower body portions 602, 604 can be configured to transition to the increased profile configuration when the central body portion 606 is inserted between the upper and lower body portions 602, 604. After the upper and lower body portions 602, 604 are delivered through the Kambin triangle utilizing the techniques and devices described above, a deployment tool can engage the central body portion 606 and deliver the central body portion 606 through the cannula and into the intervertebral space. As shown in FIG. 31A, the central body portion 606 can include one or more openings 646 configured to interact with the deployment tool. For example, the central body portion 606 can include two openings 646 at an end of the central body portion 606. As another example, the central body portion can include one or more depressions, similar to depressions 542, 562 of implant 500 to facilitate grasping using a grasper tool.

In some instances, the central body portion 606 can be inserted between the upper and lower body portions 602, 604 by moving the central body portion 606 along an axis generally perpendicular to the longitudinal axes of the upper and lower body portions 602, 604. The central body portion 606 can be moved through an opening formed by motion limiting portions 616, 626 until the socket portions of the upper and lower body portions 602, 604 interact with the ball portion 642 of the central body portion 606.

In other instances, the central body portion 606 can be inserted between the upper and lower body portions 602, 604 by moving the central body portion 606 along an axis that is generally parallel with the longitudinal axes of the upper and lower body portions 602, 604. The central body portion 606 can inserted into a space between end portions of the upper and lower body portions 602, 604 and moved inward until the socket portions of the upper and lower body portions 602, 604 interact with the ball portion 642 of the central body portion 606. As the central body portion 606 is moved inward, the longitudinal axis of the central body portion 606 can be generally perpendicular to the longitudinal axes of the upper and lower body portions 602, 604. In certain variants, as the central body portion 606 is moved inward, the longitudinal axis of the central body portion 606 can be generally parallel to the longitudinal axes of the upper and lower body portions 602, 604. Once the ball portion 642 of the central body portion 606 interacts with the joint portions of the upper and lower body portions, the central body portion 606 can be rotated until the central body portion 606 is generally perpendicular to the upper and lower body portions 602, 604, or any other desired angle.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Certain Embodiments

1. An intervertebral implant comprising:
a first body portion comprising a first member, a second member, and a first joint portion;
a first shaft, the first member and the second member pivotable around the shaft;
a second body portion comprising a first member, a second member, and a second joint portion; and
a second shaft, the first member of the second body portion and the second member of the second body portion pivotable around the shaft,
wherein the first joint portion removably connects to the second joint portion.

2. The implant of Embodiment 1, wherein the first and second body portions include one or more apertures.

3. The implant of Embodiment 1, wherein the first and second body portions include one or more textured surfaces.

4. The implant of Embodiment 3, wherein the one or more textured surfaces includes a ribbed surface.

5. The implant of Embodiment 1, wherein the first and second body portions include a bioactive coating.

6. The implant of Embodiment 1, wherein the first joint portion and the second joint portion form a ball and socket joint.

7. The implant of Embodiment 1, wherein the first and second body portions include one or more depressions configured for interaction with a deployment tool.

8. An intervertebral implant comprising:
a body portion including a first member and a second member, the first body portion including an open configuration and a closed configuration;
a shaft, the first member of the first body portion and the second member pivotable around the shaft from the closed configuration to the open configuration,
wherein the body portion includes a motion limiting portion to limit rotational movement of first member relative to the second member when the body portion is in the open configuration.

9. The implant of Embodiment 8, wherein the first member is configured to translate along a central axis of the shaft.

10. The implant of Embodiment 8, wherein one or more surfaces of the body portion include a textured surface.

11. The implant of Embodiment 10, wherein the textured surface is a ribbed surface.

12. The implant of Embodiment 8, further comprising one or more apertures.

13. The implant of Embodiment 8, further comprising a bioactive coating.

14. The implant of Embodiment 8, wherein the body portion includes one or more depressions configured for interaction with a deployment tool.

15. The implant of Embodiment 8, wherein the body portion includes a spring-loaded mechanism capable of transitioning the body portion from the closed configuration to the open configuration.

16. A method of performing orthopedic surgery comprising:
engaging a first body portion with a deployment tool;
delivering the first body portion into an intervertebral space; and
transitioning the first body portion from a closed configuration to an open configuration.

17. The method of Embodiment 16, wherein delivering the first body portion further comprises delivering the first body portion through a posterolateral approach.

18. The method of Embodiment 17, wherein delivering the first body portion through the posterolateral approach further comprises delivering the first body portion through a Kambin's triangle.

19. The method of Embodiment 16, further comprising:
engaging a second body portion with the deployment tool;

delivering the second body portion into the intervertebral space;

and transitioning the second body portion from a closed configuration to an open configuration.

20. The method of Embodiment 19, further comprising connecting a first joint portion of the first body portion to a second joint portion of the second body portion.

21. The steps, features, elements, acts, compositions, modules, components, examples, arrangements, and structures described or depicted herein, individually or in any combination or sub-combination thereof.

What is claimed is:

1. A spinal implant comprising:
    an upper body portion comprising a first upper surface and a second surface, the second surface of the upper body portion comprising a socket portion;
    a lower body portion comprising a first surface and a second surface, the second surface of the lower body portion comprising a socket portion; and
    a central body portion between the upper body portion and the lower body portion, the central body portion comprising a first surface and a second surface, each of the first and second surfaces of the central body portion comprising a ball portion, the ball portions of the central body portion being configured to interface with corresponding socket portions of the upper and lower body portions,
    wherein the spinal implant is configured to transition from a reduced profile configuration to an increased profile configuration by inserting the central body portion between the upper and lower body portions, and
    wherein the central body portion is generally perpendicular to the upper and lower body portions when the spinal implant is in the increased profile configuration.

2. The spinal implant of claim 1, wherein in the reduced profile configuration, the upper and lower body portions form an opening through which the central body portion can be inserted.

3. The spinal implant of claim 1, wherein the first surfaces of the upper and lower body portions are generally curved.

4. The spinal implant of claim 2, wherein the second surfaces of the upper and lower body portions are generally curved in a direction opposite the first surfaces of the upper and lower body portions.

5. The spinal implant of claim 1, wherein the first and second surfaces of the central body portion are generally curved in opposite directions.

6. The spinal implant of claim 1, wherein the upper and lower body portions comprise metal, and wherein the central body portion comprises a non-metal material.

7. The spinal implant of claim 1, wherein the socket portions extend through an entire thickness of their respective upper and lower body portions.

8. The spinal implant of claim 1, wherein the central body portion extends out with respect to opposed sides of each of the upper and lower body portions.

9. A spinal implant comprising: an upper body portion comprising a first upper surface and a second surface, the second surface of the upper body portion comprising a notch; a lower body portion comprising a first surface and a second surface, the second surface of the lower body portion comprising a notch; and
    a one piece central body portion between the upper body portion and the lower body portion, the central body portion comprising an upper surface and a lower surface, each of the upper and lower surfaces of the central body portion comprising a notch, the notches of the central body portion being configured to interface with corresponding notches of the upper and lower body portions,
    wherein the spinal implant is configured to transition from a reduced profile configuration to an increased profile configuration by inserting the central body portion between the upper and lower body portions, and
    wherein the central body portion is generally perpendicular to the upper and lower body portions when the spinal implant is in the increased profile configuration.

10. The spinal implant of claim 9, wherein in the reduced profile configuration, the upper and lower body portions form an opening through which the central body portion can be inserted.

11. The spinal implant of claim 9, wherein the first surfaces of the upper and lower body portions are generally curved.

12. The spinal implant of claim 11, wherein the second surfaces of the upper and lower body portions are generally curved in a direction opposite the first surfaces of the upper and lower body portions.

13. The spinal implant of claim 9, wherein the upper and lower surfaces of the central body portion are generally curved in opposite directions.

14. The spinal implant of claim 9, wherein each of the notches of the upper and lower body portions comprises a socket portion, and wherein each of the notches of the central body portion comprises a ball portion, the ball portions configured to interface with the socket portions of the upper and lower body portions.

15. The spinal implant of claim 14, wherein the socket portions extend through an entire thickness of their respective upper and lower body portions.

16. The spinal implant of claim 9, wherein the upper and lower body portions comprise metal, and wherein the central body portion comprises a non-metal material.

* * * * *